(12) United States Patent
Smith et al.

(10) Patent No.: US 11,981,027 B2
(45) Date of Patent: May 14, 2024

(54) TUNABLE ACTUATOR JOINT MODULES HAVING ENERGY RECOVERING QUASI-PASSIVE ELASTIC ACTUATORS WITH INTERNAL VALVE ARRANGEMENTS

(71) Applicant: Sarcos Corp., Salt Lake City, UT (US)

(72) Inventors: Fraser M. Smith, Salt Lake City, UT (US); Marc X. Olivier, Salt Lake City, UT (US); Brian J. Maclean, Salt Lake City, UT (US); Michael Myers, Holladay, UT (US)

(73) Assignee: Sarcos Corp., Salt Lake City, UT (US)

( * ) Notice: Subject to any disclaimer, the term of this patent is extended or adjusted under 35 U.S.C. 154(b) by 632 days.

(21) Appl. No.: 17/093,487

(22) Filed: Nov. 9, 2020

(65) Prior Publication Data

US 2021/0069892 A1 Mar. 11, 2021

Related U.S. Application Data

(62) Division of application No. 15/810,119, filed on Nov. 12, 2017, now Pat. No. 10,828,767.

(Continued)

(51) Int. Cl.
*B25J 9/00* (2006.01)
*A61F 2/64* (2006.01)
(Continued)

(52) U.S. Cl.
CPC .............. *B25J 9/0006* (2013.01); *A61F 2/64* (2013.01); *A61F 2/68* (2013.01); *A61F 2/70* (2013.01);
(Continued)

(58) Field of Classification Search
CPC ........ B25J 9/0006; B25J 9/148; B25J 13/085; B25J 19/007; A61F 2/64; A61F 2/68;
(Continued)

(56) References Cited

U.S. PATENT DOCUMENTS 1,880,138 A 9/1932 Franz
2,850,189 A 9/1958 Leroy
(Continued)

FOREIGN PATENT DOCUMENTS

CN 101214653 A 7/2008
CN 101823517 A 9/2010
(Continued)

OTHER PUBLICATIONS

International Search Report for International Application No. PCT/US2021/062051 dated Mar. 16, 2022, 29 pages.
(Continued)

*Primary Examiner* — Bruce E Snow

(57) ABSTRACT

A robotic system for a robotic limb configured to recover energy for minimizing power consumption of the robotic system, comprising a first support member, a second support member, and a quasi-passive elastic actuator rotatably coupling the first and second support members to define a joint of the robotic system rotatable about an axis of rotation defining a degree of freedom. The quasi-passive elastic actuator can comprise a first vane device and a second vane device, the first vane device and second vane device being rotatable relative to each other within the housing and defining, at least in part, a compression chamber and an expansion chamber. The system can further comprise a valve assembly, the valve assembly comprising a valve device disposed through an opening of the first vane device along the axis of rotation, and a shunt circuit facilitating fluid flow between the compression and expansion chambers through the valve assembly. The valve assembly is operable to (Continued)

position the valve device in an open position to open the shunt circuit to place the quasi-passive elastic actuator in an inelastic state, and to position the valve device in a closed position to close the shunt circuit to place the quasi-passive elastic actuator in an elastic state.

22 Claims, 58 Drawing Sheets

Related U.S. Application Data

(60) Provisional application No. 62/421,175, filed on Nov. 11, 2016.

(51) Int. Cl.
  *A61F 2/68* (2006.01)
  *A61F 2/70* (2006.01)
  *B25J 9/14* (2006.01)
  *B25J 13/08* (2006.01)
  *F15B 15/12* (2006.01)
  *A61F 2/50* (2006.01)
  *B25J 19/00* (2006.01)
  *F15B 11/072* (2006.01)
  *F15B 15/20* (2006.01)

(52) U.S. Cl.
  CPC .............. *B25J 9/148* (2013.01); *B25J 13/085* (2013.01); *A61F 2002/5003* (2013.01); *A61F 2002/5072* (2013.01); *B25J 19/007* (2013.01); *F15B 11/072* (2013.01); *F15B 15/12* (2013.01); *F15B 15/204* (2013.01); *F15B 2211/3058* (2013.01); *F15B 2211/7058* (2013.01)

(58) Field of Classification Search
  CPC ................. A61F 2/70; A61F 2002/5003; A61F 2002/5072; F15B 15/12
  See application file for complete search history.

(56) References Cited

U.S. PATENT DOCUMENTS

| | | |
|---|---|---|
| 2,981,198 A | 4/1961 | Nettel |
| 3,171,549 A | 3/1965 | Orloff |
| 3,280,991 A | 10/1966 | Melton et al. |
| 3,306,646 A | 2/1967 | Flora, Jr. |
| 3,358,678 A | 12/1967 | Kulstar |
| 3,449,008 A | 6/1969 | Colechia |
| 3,449,769 A | 6/1969 | Mizen |
| 3,535,711 A | 10/1970 | Fick |
| 3,759,563 A | 9/1973 | Kitamura |
| 3,858,468 A | 1/1975 | Pasbrig |
| 4,046,262 A | 9/1977 | Vykukal et al. |
| 4,179,233 A | 12/1979 | Bromell et al. |
| 4,200,596 A | 4/1980 | Iiyama et al. |
| 4,251,791 A | 2/1981 | Yanagisawa et al. |
| 4,367,891 A | 1/1983 | Wauer et al. |
| 4,398,110 A | 8/1983 | Flinchbaugh et al. |
| 4,483,407 A | 11/1984 | Iwamoto et al. |
| 4,561,686 A | 12/1985 | Atchley |
| 4,567,417 A | 1/1986 | Francois et al. |
| 4,575,297 A | 3/1986 | Richter |
| 4,591,944 A | 5/1986 | Gravel |
| 4,598,601 A | 7/1986 | Molaug |
| 4,603,896 A | 8/1986 | Vasseur et al. |
| 4,661,032 A | 4/1987 | Arai |
| 4,666,357 A | 5/1987 | Babbi |
| 4,723,353 A | 2/1988 | Monforte |
| 4,762,455 A | 8/1988 | Coughlan et al. |
| 4,768,143 A | 8/1988 | Lane et al. |
| 4,821,594 A | 4/1989 | Rosheim et al. |
| 4,834,443 A | 5/1989 | Crowder et al. |
| 4,853,874 A | 8/1989 | Iwamoto et al. |
| 4,883,400 A | 11/1989 | Kuban et al. |
| 4,884,720 A | 12/1989 | Whigham et al. |
| 4,915,437 A | 4/1990 | Cherry |
| 4,921,292 A | 5/1990 | Harwell et al. |
| 4,997,095 A | 3/1991 | Jones et al. |
| 5,004,391 A | 4/1991 | Burdea |
| 5,038,089 A | 8/1991 | Szakaly |
| 5,072,361 A | 12/1991 | Davis et al. |
| 5,080,682 A | 1/1992 | Schectman |
| 5,101,472 A | 3/1992 | Repperger |
| 5,105,367 A | 4/1992 | Tsuchihashi et al. |
| 5,117,814 A | 6/1992 | Luttrell et al. |
| 5,144,943 A | 9/1992 | Luttrell et al. |
| 5,172,951 A | 12/1992 | Jacobsen et al. |
| 5,230,147 A | 7/1993 | Asaoka et al. |
| 5,239,246 A | 8/1993 | Kim |
| 5,246,216 A | 9/1993 | Oberst |
| 5,280,981 A | 1/1994 | Schulz |
| 5,282,460 A | 2/1994 | Boldt |
| 5,328,224 A | 7/1994 | Jacobsen et al. |
| 5,336,982 A | 8/1994 | Backes |
| 5,389,849 A | 2/1995 | Asano et al. |
| 5,399,951 A | 3/1995 | Lavallee et al. |
| 5,402,690 A | 4/1995 | Sekiguchi et al. |
| 5,516,249 A | 5/1996 | Brimhall |
| 5,577,417 A | 11/1996 | Fournier |
| 5,577,902 A | 11/1996 | Todo et al. |
| 5,588,688 A | 12/1996 | Jacobsen et al. |
| 5,664,636 A | 9/1997 | Ikuma et al. |
| 5,704,945 A * | 1/1998 | Wagner ..................... A61F 2/64 623/44 |
| 5,762,390 A | 6/1998 | Gosselin et al. |
| 5,784,542 A | 7/1998 | Ohm et al. |
| 5,785,505 A | 7/1998 | Price |
| 5,797,615 A | 8/1998 | Murray |
| 5,845,540 A | 12/1998 | Rosheim |
| 5,865,770 A | 2/1999 | Schectman |
| 5,898,599 A | 4/1999 | Massie et al. |
| 5,912,658 A | 6/1999 | Bergamasco et al. |
| 5,949,686 A | 9/1999 | Yoshinada et al. |
| 5,957,981 A * | 9/1999 | Gramnas ............... A61F 2/6607 623/47 |
| 5,961,476 A | 10/1999 | Betto et al. |
| 5,967,580 A | 10/1999 | Rosheim |
| 5,994,864 A | 11/1999 | Inoue et al. |
| 6,016,385 A | 1/2000 | Yee et al. |
| 6,170,162 B1 | 1/2001 | Jacobsen et al. |
| 6,202,013 B1 | 3/2001 | Anderson et al. |
| 6,272,924 B1 | 8/2001 | Jansen |
| 6,301,526 B1 | 10/2001 | Kim et al. |
| 6,338,605 B1 | 1/2002 | Halverson et al. |
| 6,340,065 B1 | 1/2002 | Harris |
| 6,360,166 B1 | 3/2002 | Alster |
| 6,394,731 B1 | 5/2002 | Konosu et al. |
| 6,425,865 B1 | 7/2002 | Salcudean et al. |
| 6,430,473 B1 | 8/2002 | Lee et al. |
| 6,435,794 B1 | 8/2002 | Springer |
| 6,507,163 B1 | 1/2003 | Allen |
| 6,508,058 B1 | 1/2003 | Seaverson |
| 6,554,342 B1 | 4/2003 | Burnett |
| 6,641,371 B2 | 11/2003 | Graziani et al. |
| 6,659,703 B1 | 12/2003 | Kirkley |
| 6,659,939 B2 | 12/2003 | Moll et al. |
| 6,663,154 B2 | 12/2003 | Pancheri |
| 6,714,839 B2 | 3/2004 | Salisbury, Jr. et al. |
| 6,740,125 B2 * | 5/2004 | Mosler ..................... F16F 9/53 623/24 |
| 6,855,170 B2 * | 2/2005 | Gramnas .................. A61F 2/68 623/49 |
| 6,920,374 B2 | 7/2005 | Takenaka et al. |
| 7,168,748 B2 | 1/2007 | Townsend et al. |
| 7,319,919 B2 | 1/2008 | Takenaka et al. |
| 7,337,040 B2 | 2/2008 | Takenaka et al. |
| 7,379,789 B2 | 5/2008 | Takenaka et al. |
| 7,396,057 B2 | 7/2008 | Ye et al. |
| 7,405,531 B2 | 7/2008 | Khatib et al. |
| 7,409,882 B2 | 8/2008 | Massimo et al. |

(56) References Cited

U.S. PATENT DOCUMENTS

| | | |
|---|---|---|
| 7,410,338 B2 | 8/2008 | Schiele et al. |
| 7,509,905 B2 | 3/2009 | Jacobsen et al. |
| 7,628,766 B1 | 12/2009 | Kazerooni et al. |
| 7,783,384 B2 | 8/2010 | Kraft |
| 7,862,522 B1 | 1/2011 | Barclay et al. |
| 7,862,524 B2 | 1/2011 | Carignan et al. |
| 7,883,546 B2 | 2/2011 | Kazerooni et al. |
| 7,947,004 B2 | 5/2011 | Kazerooni et al. |
| 7,965,006 B2 | 6/2011 | Kang et al. |
| 8,024,071 B2 | 9/2011 | Komatsu et al. |
| 8,051,764 B2 | 11/2011 | Jacobsen et al. |
| 8,100,451 B2 | 1/2012 | Okuda et al. |
| 8,112,179 B2 | 2/2012 | Nakajima |
| 8,132,835 B2 | 3/2012 | Ban et al. |
| 8,151,401 B2 | 4/2012 | Cheyne |
| 8,182,010 B2 | 5/2012 | Lee et al. |
| 8,204,626 B2 | 6/2012 | Yoshiike et al. |
| 8,245,728 B2 | 8/2012 | Jacobsen et al. |
| 8,295,975 B2 | 10/2012 | Arimatsu et al. |
| 8,336,420 B2 | 12/2012 | Carter et al. |
| 8,375,982 B2 | 2/2013 | Gray, Jr. |
| 8,435,309 B2 | 5/2013 | Gilbert et al. |
| 8,452,447 B2 | 5/2013 | Nixon |
| 8,473,101 B2 | 6/2013 | Summer |
| 8,511,192 B2 | 8/2013 | Hirtt et al. |
| 8,516,918 B2 | 8/2013 | Jacobsen et al. |
| 8,529,582 B2 | 9/2013 | Devengenzo et al. |
| 8,534,728 B1 | 9/2013 | Bosscher et al. |
| 8,560,118 B2 | 10/2013 | Greer et al. |
| 8,640,723 B2 | 2/2014 | Jacobsen et al. |
| 8,667,643 B2 | 3/2014 | Simonelli et al. |
| 8,672,378 B2 | 3/2014 | Yamasaki et al. |
| 8,747,486 B2 | 6/2014 | Kawasaki et al. |
| 8,794,262 B2 | 8/2014 | Jacobsen et al. |
| 8,821,338 B2 | 9/2014 | Thorson |
| 8,849,457 B2 | 9/2014 | Jacobsen et al. |
| 8,870,967 B2 | 10/2014 | Herr et al. |
| 8,881,616 B2 | 11/2014 | Dize et al. |
| 8,888,864 B2 * | 11/2014 | Iversen ............... A61F 2/6607 623/48 |
| 8,892,258 B2 | 11/2014 | Jacobsen et al. |
| 8,920,517 B2 * | 12/2014 | Smith ............... A61F 2/70 623/24 |
| 8,942,846 B2 | 1/2015 | Jacobsen et al. |
| 8,977,388 B2 | 3/2015 | Jacobsen et al. |
| 8,977,398 B2 | 3/2015 | Jacobsen et al. |
| 9,079,305 B2 | 7/2015 | Williamson et al. |
| 9,205,560 B1 | 12/2015 | Edsinger et al. |
| 9,295,604 B2 | 3/2016 | Zoss et al. |
| 9,314,921 B2 | 4/2016 | Jacobsen et al. |
| 9,329,587 B2 | 5/2016 | Fudaba et al. |
| 9,333,097 B2 | 5/2016 | Herr et al. |
| 9,346,165 B1 | 5/2016 | Metzger et al. |
| 9,526,636 B2 | 12/2016 | Bedard et al. |
| 9,533,411 B2 | 1/2017 | Jacobsen et al. |
| 9,616,580 B2 | 4/2017 | Smith et al. |
| 9,618,937 B1 | 4/2017 | Blankespoor et al. |
| 9,643,323 B2 | 5/2017 | Nagatsuka et al. |
| 9,727,076 B2 | 8/2017 | Smith et al. |
| 9,789,603 B2 | 10/2017 | Jacobsen et al. |
| 9,895,812 B2 | 2/2018 | Gonzalez et al. |
| 9,926,025 B1 | 3/2018 | Blankespoor et al. |
| 10,028,844 B2 * | 7/2018 | Cheng ............... A61F 2/68 |
| 10,071,485 B2 | 9/2018 | Schiele et al. |
| 10,216,177 B2 | 2/2019 | Gildert et al. |
| 10,300,969 B1 | 5/2019 | Blackespoor et al. |
| 10,406,676 B2 | 9/2019 | Smith et al. |
| 10,512,583 B2 | 12/2019 | Smith |
| 10,518,404 B2 | 12/2019 | Barnes |
| 10,533,542 B2 | 1/2020 | Smith et al. |
| 10,561,564 B2 | 2/2020 | LaChappelle et al. |
| 10,566,914 B2 | 2/2020 | Fujita et al. |
| 10,609,896 B2 | 4/2020 | Kraaij et al. |
| 10,709,633 B2 | 7/2020 | Kazerooni et al. |
| 10,765,537 B2 | 9/2020 | Smith et al. |
| 10,828,767 B2 | 11/2020 | Smith et al. |
| 11,148,279 B1 | 10/2021 | Mooney et al. |
| 11,241,801 B2 | 2/2022 | Smith et al. |
| 2001/0033146 A1 | 10/2001 | Kato et al. |
| 2001/0043847 A1 | 11/2001 | Kramer |
| 2002/0075233 A1 | 6/2002 | White et al. |
| 2002/0094919 A1 | 7/2002 | Rennex et al. |
| 2003/0005896 A1 | 1/2003 | Jacobsen et al. |
| 2003/0060808 A1 | 3/2003 | Wilk |
| 2003/0146720 A1 | 8/2003 | Riwan et al. |
| 2003/0152452 A1 | 8/2003 | Hodgson |
| 2003/0223844 A1 | 12/2003 | Schiele et al. |
| 2004/0004362 A1 | 1/2004 | Love |
| 2004/0037681 A1 | 2/2004 | Marcotte |
| 2004/0102723 A1 | 5/2004 | Horst |
| 2004/0106881 A1 | 6/2004 | McBean et al. |
| 2004/0116836 A1 | 6/2004 | Kawai et al. |
| 2004/0246769 A1 | 12/2004 | Ido |
| 2004/0250644 A1 | 12/2004 | Gosselin et al. |
| 2005/0059908 A1 | 3/2005 | Bogert |
| 2005/0099386 A1 | 5/2005 | Kukita |
| 2005/0159850 A1 | 7/2005 | Melman |
| 2005/0166413 A1 | 8/2005 | Crampton |
| 2005/0193451 A1 | 9/2005 | Quistgaard et al. |
| 2005/0251110 A1 | 11/2005 | Nixon |
| 2006/0052732 A1 | 3/2006 | Shimada et al. |
| 2006/0064047 A1 | 3/2006 | Shimada et al. |
| 2006/0069449 A1 | 3/2006 | Bisbee, III et al. |
| 2006/0130594 A1 | 6/2006 | Ikeuchi |
| 2006/0149419 A1 | 7/2006 | Ogawa et al. |
| 2006/0184275 A1 | 8/2006 | Hosokawa et al. |
| 2006/0197049 A1 | 9/2006 | Hamada et al. |
| 2006/0245897 A1 | 11/2006 | Hariki et al. |
| 2006/0249315 A1 | 11/2006 | Herr et al. |
| 2007/0054777 A1 | 3/2007 | Kawai et al. |
| 2007/0056592 A1 | 3/2007 | Angold et al. |
| 2007/0105070 A1 | 5/2007 | Trawick |
| 2007/0123997 A1 | 5/2007 | Herr et al. |
| 2007/0129653 A1 | 6/2007 | Sugar et al. |
| 2008/0009771 A1 | 1/2008 | Perry et al. |
| 2008/0023974 A1 | 1/2008 | Park et al. |
| 2008/0156363 A1 | 7/2008 | Ikeuchi et al. |
| 2008/0269027 A1 | 10/2008 | Chen |
| 2008/0271942 A1 | 11/2008 | Yamashita et al. |
| 2008/0281468 A1 | 11/2008 | Jacobsen et al. |
| 2009/0036815 A1 | 2/2009 | Ido |
| 2009/0038258 A1 | 2/2009 | Pivac et al. |
| 2009/0039579 A1 | 2/2009 | Clifford et al. |
| 2009/0199883 A1 | 8/2009 | Hiki |
| 2009/0210093 A1 | 8/2009 | Jacobsen et al. |
| 2009/0294238 A1 | 12/2009 | Gilmore |
| 2010/0050947 A1 | 3/2010 | Kortekaas |
| 2010/0089855 A1 | 4/2010 | Kjolseth |
| 2010/0094185 A1 | 4/2010 | Amundson et al. |
| 2010/0152630 A1 | 6/2010 | Matsuoka et al. |
| 2010/0198402 A1 | 8/2010 | Greer et al. |
| 2010/0234996 A1 | 9/2010 | Schreiber et al. |
| 2010/0241242 A1 | 9/2010 | Herr et al. |
| 2010/0295497 A1 | 11/2010 | Takamatsu |
| 2011/0010012 A1 | 1/2011 | Murayama et al. |
| 2011/0015786 A1 | 1/2011 | Kawai |
| 2011/0040216 A1 | 2/2011 | Herr et al. |
| 2011/0046781 A1 | 2/2011 | Summer |
| 2011/0066088 A1 | 3/2011 | Little et al. |
| 2011/0071677 A1 | 3/2011 | Stillman |
| 2011/0214524 A1 | 9/2011 | Jacobsen et al. |
| 2011/0219899 A1 | 9/2011 | Dize et al. |
| 2011/0264230 A1 | 10/2011 | Herr et al. |
| 2012/0000891 A1 | 1/2012 | Nakanishi et al. |
| 2012/0060322 A1 | 3/2012 | Simonelli et al. |
| 2012/0065902 A1 | 3/2012 | Nakajima |
| 2012/0073930 A1 | 3/2012 | Lansberry et al. |
| 2012/0137667 A1 | 6/2012 | Jacobsen et al. |
| 2012/0179075 A1 | 7/2012 | Perry et al. |
| 2012/0191245 A1 | 7/2012 | Fudaba et al. |
| 2012/0216671 A1 | 8/2012 | Gammon |
| 2012/0237319 A1 | 9/2012 | Jacobsen et al. |
| 2012/0259429 A1 | 10/2012 | Han et al. |
| 2012/0277901 A1 | 11/2012 | Jacobsen et al. |

(56) References Cited

U.S. PATENT DOCUMENTS

| | | |
|---|---|---|
| 2012/0277911 A1 | 11/2012 | Jacobsen et al. |
| 2012/0277915 A1 | 11/2012 | Jacobsen et al. |
| 2012/0328395 A1 | 12/2012 | Jacobsen et al. |
| 2013/0011220 A1 | 1/2013 | Jacobsen et al. |
| 2013/0013108 A1 | 1/2013 | Jacobsen et al. |
| 2013/0023803 A1 | 1/2013 | Hsu et al. |
| 2013/0033050 A1 | 2/2013 | Matsuoka et al. |
| 2013/0057001 A1 | 3/2013 | Tsai |
| 2013/0090580 A1 | 4/2013 | Hong et al. |
| 2013/0106127 A1 | 5/2013 | Lipson et al. |
| 2013/0106128 A1 | 5/2013 | Yamasaki et al. |
| 2013/0192406 A1 | 8/2013 | Godowski |
| 2013/0226048 A1 | 8/2013 | Unluhisarcikili et al. |
| 2013/0253385 A1 | 9/2013 | Goffer et al. |
| 2013/0296746 A1 | 11/2013 | Herr et al. |
| 2013/0302129 A1 | 11/2013 | Smith et al. |
| 2013/0306430 A1 | 11/2013 | Laffranchi et al. |
| 2013/0331744 A1 | 12/2013 | Kamon |
| 2013/0333368 A1 | 12/2013 | Durfee et al. |
| 2014/0067124 A1 | 3/2014 | Williamson et al. |
| 2014/0088728 A1 | 3/2014 | Herr |
| 2014/0100492 A1 | 4/2014 | Nagasaka |
| 2014/0190289 A1 | 7/2014 | Zhu |
| 2014/0195052 A1 | 7/2014 | Tsusaka et al. |
| 2015/0073595 A1 | 3/2015 | Fudaba et al. |
| 2015/0073596 A1 | 3/2015 | Fudaba et al. |
| 2015/0173929 A1 | 6/2015 | Kazerooni et al. |
| 2015/0209214 A1 | 7/2015 | Herr et al. |
| 2015/0217457 A1 | 8/2015 | Lipson et al. |
| 2015/0272749 A1 | 10/2015 | Amend, Jr. et al. |
| 2015/0278263 A1 | 10/2015 | Bowles et al. |
| 2015/0289995 A1 | 10/2015 | Wilkinson et al. |
| 2015/0321340 A1 | 11/2015 | Smith |
| 2015/0321342 A1 | 11/2015 | Smith et al. |
| 2016/0003268 A1 | 1/2016 | Shevchenko et al. |
| 2016/0114482 A1 | 4/2016 | Lessing et al. |
| 2016/0153508 A1 | 6/2016 | Battlogg |
| 2016/0279788 A1 | 9/2016 | Kanaoka et al. |
| 2016/0331556 A1 | 11/2016 | Wijesundara et al. |
| 2016/0331572 A1 | 11/2016 | Popovic et al. |
| 2016/0332302 A1 | 11/2016 | Bingham et al. |
| 2016/0332305 A1 | 11/2016 | Gonzalez et al. |
| 2016/0332312 A1 | 11/2016 | Song et al. |
| 2017/0050310 A1 | 2/2017 | Kanaoka |
| 2017/0119132 A1 | 5/2017 | Pruess et al. |
| 2017/0326737 A1 | 11/2017 | Martin et al. |
| 2018/0126548 A1 | 5/2018 | Sugito et al. |
| 2018/0133905 A1 | 5/2018 | Smith et al. |
| 2018/0133906 A1 | 5/2018 | Smith et al. |
| 2018/0193172 A1 | 7/2018 | Smith et al. |
| 2018/0193999 A1 | 7/2018 | Jacobsen et al. |
| 2018/0194000 A1 | 7/2018 | Smith et al. |
| 2018/0221237 A1 | 8/2018 | Swift et al. |
| 2018/0290309 A1 | 10/2018 | Becker et al. |
| 2018/0298976 A1 | 10/2018 | Battlogg |
| 2019/0022853 A1 | 1/2019 | Kim et al. |
| 2019/0105777 A1 | 4/2019 | Dalley et al. |
| 2019/0138423 A1 | 5/2019 | Agerstam et al. |
| 2019/0176320 A1 | 6/2019 | Smith et al. |
| 2019/0184576 A1 | 6/2019 | Smith et al. |
| 2020/0001450 A1 | 1/2020 | Smith et al. |
| 2020/0164523 A1 | 5/2020 | Hallock et al. |
| 2020/0281803 A1 | 9/2020 | Teng et al. |
| 2020/0312109 A1 | 10/2020 | Shionozaki |
| 2020/0346009 A1 | 11/2020 | Murray et al. |
| 2020/0368094 A1 | 11/2020 | Yoshimi et al. |
| 2020/0405417 A1 | 12/2020 | Shelton, IV et al. |
| 2021/0039269 A1 | 2/2021 | Son |
| 2021/0059780 A1 | 3/2021 | Sutherland et al. |
| 2021/0369536 A1 | 12/2021 | Mooney et al. |
| 2021/0378903 A1 | 12/2021 | Mooney et al. |
| 2023/0023083 A1 | 1/2023 | Shelton, IV et al. |

FOREIGN PATENT DOCUMENTS

| | | |
|---|---|---|
| CN | 101486191 B | 11/2012 |
| CN | 103610524 A | 3/2014 |
| CN | 203495949 U | 3/2014 |
| CN | 103802907 A | 5/2014 |
| CN | 203752160 U | 8/2014 |
| CN | 104843484 A | 8/2015 |
| CN | 105411813 A | 3/2016 |
| CN | 205250544 U | 5/2016 |
| CN | 105818143 A | 8/2016 |
| CN | 105856190 A | 8/2016 |
| CN | 107471203 A | 12/2017 |
| CN | 108081303 A | 5/2018 |
| CN | 111267992 A | 6/2020 |
| CN | 111616914 A | 9/2020 |
| DE | 102004029513 B3 | 9/2005 |
| DE | 102010029088 A1 | 11/2011 |
| DE | 202013009698 U1 | 11/2013 |
| DE | 102016201540 A1 | 8/2017 |
| DE | 202018104980 U1 | 9/2018 |
| EP | 0039578 A1 | 11/1981 |
| EP | 0616275 A3 | 9/1998 |
| EP | 1037264 A2 | 9/2000 |
| EP | 1258324 A2 | 11/2002 |
| EP | 1442846 A1 | 8/2004 |
| EP | 1721593 A1 | 11/2006 |
| EP | 2198810 A1 | 6/2010 |
| EP | 2548543 B1 | 1/2015 |
| EP | 2942162 A2 | 11/2015 |
| EP | 2168548 B1 | 10/2016 |
| FR | 2651220 A1 | 3/1991 |
| GB | 686237 A | 1/1953 |
| GB | 2278041 A | 11/1994 |
| JP | S34-015764 | 10/1959 |
| JP | S36-005228 | 5/1961 |
| JP | S44-000603 | 1/1969 |
| JP | S50-009803 | 1/1975 |
| JP | S50-006043 | 3/1975 |
| JP | S52-013252 A | 2/1977 |
| JP | S52-134985 A | 11/1977 |
| JP | S56-114688 A | 9/1981 |
| JP | S56-140510 A | 11/1981 |
| JP | S58-113586 A | 7/1983 |
| JP | S58-45724 B2 | 10/1983 |
| JP | S60-177883 U | 11/1985 |
| JP | S62-193784 A | 8/1987 |
| JP | S62-200600 A | 9/1987 |
| JP | H01-295772 A | 11/1989 |
| JP | H02-51083 U | 4/1990 |
| JP | H03-85398 U | 8/1991 |
| JP | H04-44296 U | 4/1992 |
| JP | H05-004177 A | 1/1993 |
| JP | H05-023989 A | 2/1993 |
| JP | H06-213266 A | 8/1994 |
| JP | H06-315879 A | 11/1994 |
| JP | H07-001366 A | 1/1995 |
| JP | H07-5129 Y2 | 2/1995 |
| JP | H07-060679 A | 3/1995 |
| JP | H07-112377 A | 5/1995 |
| JP | H07-031291 U | 6/1995 |
| JP | H07-246578 A | 9/1995 |
| JP | H08-126984 A | 5/1996 |
| JP | H09-11176 A | 1/1997 |
| JP | H09-190207 A | 7/1997 |
| JP | H1156931 | 3/1999 |
| JP | H11-130279 A | 5/1999 |
| JP | 2002-161547 A | 6/2002 |
| JP | 2003-089084 A | 3/2003 |
| JP | 2003-103480 A | 4/2003 |
| JP | 2003-146575 A | 5/2003 |
| JP | 2003-194104 A | 7/2003 |
| JP | 2004-041279 A | 2/2004 |
| JP | 2004-105261 A | 4/2004 |
| JP | 2004-195576 A | 7/2004 |
| JP | 2005-118938 A | 5/2005 |
| JP | 2005-237504 A | 9/2005 |
| JP | 2005-334999 A | 12/2005 |
| JP | 2006-007337 A | 1/2006 |

(56) References Cited

FOREIGN PATENT DOCUMENTS

| | | |
|---|---|---|
| JP | 2006-016916 A | 1/2006 |
| JP | 2006-028953 A | 2/2006 |
| JP | 2006-051558 A | 2/2006 |
| JP | 2006-167223 A | 6/2006 |
| JP | 3909770 B2 | 4/2007 |
| JP | 2007-130234 A | 5/2007 |
| JP | 2007-252514 A | 10/2007 |
| JP | 2007-307216 A | 11/2007 |
| JP | 2008-143449 A | 6/2008 |
| JP | 2009-023828 A | 2/2009 |
| JP | 2009-167673 A | 7/2009 |
| JP | 2009-178253 A | 8/2009 |
| JP | 2009-219650 A | 10/2009 |
| JP | 2009-240488 A | 10/2009 |
| JP | 2009-268839 A | 11/2009 |
| JP | 2010-098130 A | 4/2010 |
| JP | 2010-110381 A | 5/2010 |
| JP | 2010-110465 A | 5/2010 |
| JP | 2010-142351 A | 7/2010 |
| JP | 2010-263761 A | 11/2010 |
| JP | 2011-073127 A | 4/2011 |
| JP | 2011-156171 A | 8/2011 |
| JP | 2011-193899 A | 10/2011 |
| JP | 2011-230260 A | 11/2011 |
| JP | 2012-501739 A | 1/2012 |
| JP | 2012-125279 A | 7/2012 |
| JP | 2012-176476 A | 9/2012 |
| JP | 2012-183291 A | 9/2012 |
| JP | 2013-022091 A | 2/2013 |
| JP | 2013-090693 A | 5/2013 |
| JP | 2013-123786 A | 6/2013 |
| JP | 2013-142445 A | 7/2013 |
| JP | 5267730 | 8/2013 |
| JP | 2013-176429 A | 9/2013 |
| JP | 2013-208293 A | 10/2013 |
| JP | 2013-220496 A | 10/2013 |
| JP | 2013-248699 A | 12/2013 |
| JP | 2014-054273 A | 3/2014 |
| JP | 2014-073199 A | 4/2014 |
| JP | 2014-073222 A | 4/2014 |
| JP | 2014-200853 A | 10/2014 |
| JP | 2015-112649 A | 6/2015 |
| JP | 2015-208814 A | 11/2015 |
| JP | 2015-212010 A | 11/2015 |
| JP | 2015-214019 A | 12/2015 |
| JP | 2016-539017 A | 12/2016 |
| JP | 2018-167375 | 11/2018 |
| JP | 2020-037164 A | 3/2020 |
| JP | 6748374 B2 | 9/2020 |
| KR | 2005-0037754 A | 4/2005 |
| KR | 2007-0057209 A | 6/2007 |
| KR | 2010-0112670 | 10/2010 |
| KR | 2012-0105194 A | 9/2012 |
| KR | 10-1219795 | 1/2013 |
| KR | 2013-0001409 A | 1/2013 |
| KR | 2013-0045777 A | 5/2013 |
| KR | 2018-0128731 A | 12/2018 |
| KR | 2019-0108386 A | 9/2019 |
| SE | 515372 C2 | 7/2001 |
| WO | WO 94/29605 | 12/1994 |
| WO | WO 2003/002309 A1 | 1/2003 |
| WO | WO 2003/081762 A1 | 10/2003 |
| WO | WO 2007/144629 A2 | 12/2007 |
| WO | WO 2009/040908 A1 | 4/2009 |
| WO | WO 2009/143377 A2 | 11/2009 |
| WO | WO 2010/025409 A1 | 3/2010 |
| WO | WO 2010/027968 A2 | 3/2010 |
| WO | WO 2012/042471 A1 | 4/2012 |
| WO | WO 2016/049622 A1 | 3/2016 |
| WO | WO 2017/148499 A1 | 9/2017 |
| WO | WO 2017/159504 A1 | 9/2017 |
| WO | WO 2018/118004 A1 | 6/2018 |
| WO | WO 2018/211869 A1 | 11/2018 |
| WO | WO 2018/215705 A1 | 11/2018 |
| WO | WO 2019/060791 A1 | 3/2019 |
| WO | WO 2020/175949 A1 | 9/2020 |

OTHER PUBLICATIONS

International Search Report for International Application No. PCT/US2021/062052 dated Apr. 7, 2022, 19 pages.

International Search Report for International Application No. PCT/US2021/062053 dated Mar. 17, 2022, 16 pages.

International Search Report for International Application No. PCT/US2021/062055 dated Mar. 30, 2022, 15 pages.

International Search Report for International Application No. PCT/US2021/062056 dated Apr. 4, 2022, 16 pages.

Extended European Search Report dated Feb. 22, 2022 in EP Application No. 21184013.7 filed May 6, 2015, 9 pages.

Invitation to Pay Additional Fees for International Application No. PCT/US2022/044922 dated Jan. 31, 2023, 23 pages.

International Search Report for International Application No. PCT/US2022/044924 dated Feb. 6, 2023, 16 pages.

Aghili et al., Sensing the torque in a robot's joints, www.memagazine.org/backissues/september98/features/torque/torque.html, 1998, pp. 1-9, The American Society of Mechanical Engineers.

Aliens (Movie), Starring Sigourney Weaver, Directed by James Cameron, Written by James Cameron, David Giler, Walter Hill, Dan O'Bannon, and Ronald Shuset, Released 1985 by Twentieth Century Fox, Scenes at Playtime 88:26:31-00:26:59 & 00:27:40-00:28:05 & 02:08:25-02:10:39 Non-Patent Literature documentation; Aliens(1986)—IMDb; downloaded Sep. 27, 2014; 4 pages; http://www.imdb.com/title/tt1009060S/.

Amikabir University of Technology, Manipulator Dynamics (Power Point), Computer Engineering and Information Technology Department, to the best of applicant's knowledge article was available before the application filing date, 44 pages.

Barras, Stabilization of a Biped Robot with its arms—A Practical Approach, http://biorob.epfl.ch/files/content/sites/biorob/filed/users/170220/public/Report.pdf; May 2010, 33 pages, EPFL Biorobotics Laboratory (BioRob), Switzerland.

Bauman, Utah Firm Markets on Big Gorilla of an Arm, Deseret News; Jan. 27, 1993, 2 pages, Deseret News Publishing Company, Salt Lake City, Utah.

Claeyssen et al., Magnetostrictive actuators compared to piezoelectric actuators, Proceedings of SPIE—The International Society for Optical Engineering 4763, Mar. 2003, 6 pages.

Digital World Tokyo, Giant Robot Grabbing Hands Grab All They Can, www.digitalworldtokyo.com/index.php/digital_tokyo/articles/giant_robot_grabbing_hands_grab_all_they_can/, Jul. 17, 2007, 3 pages.

Elliott et al., The Biomechanics and Energetics of Human Running using an Elastic Knee Exoskeleton, Jun. 2013, 7 pages, IEEE International Conference on Rehabilitation Robotics, Seattle, Washington.

Elliott et al., Design of a Clutch-Spring Knee Exoskeleton for Running, Journal of Medical Devices, Sep. 2014, 11 pages, vol. 8, The American Society of Mechanical Engineers, New York City, New York.

Endo et al., A quasi-passive model of human leg function in level-ground walking, 2006 IEEE/RSJ International Conference on Intelligent Robots and Systems, Oct. 9-15, 2006, pp. 4935-4939, Institute of Electrical and Electronics Engineers, Piscataway, New Jersey.

Gauthier et al., Magnetic Shape Memory Alloy and Actuator Design, Conference: 5th International Workshop on Microfactories (IWMF'06), Oct. 2006, 5 pages, Besançon, France.

Grabowski et al., Exoskeletons for Running and Hopping Augmentation, Journal of Applied Physiology, http://bomech.media.mit.edu/portfolio_page/load-bearing-exoskeleton-for-augmentation-of-human-numming/, 2009, 4 pages, vol. 107, No. 3, American Physiological Society, United States.

Hauser et al., JammJoint: A Variable Stiffness Device Based on Granular Jamming for Wearable Joint Support, IEEE Robotics and

(56) References Cited

OTHER PUBLICATIONS

Automation Letters, Apr. 2017, 7 pages, vol. 2, Issue 2, Institute of Electrical and Electronics Engineers, Piscataway, New Jersey.

Huber et al., The selection of mechanical actuators based on performance indices, Oct. 8, 1997, pp. 2185-2205, vol. 453 Issue 1965, The Royal Society, London.

Hunter et al., Fast Reversible NiTi Fibers For Use in Microrobotics, Proceedings. IEEE Micro Electro Mechanical Systems, Jan. 30-Feb. 2, 1991, pp. 166-170, Institute of Electrical and Electronics Engineers, Piscataway, New Jersey.

Industrial Magnetics, Inc., PowerLift® Magnets; www.magnetics.com/product.asp?ProductID=1; as accessed Nov. 6, 2012, 2 pages; Boyne City, Michigan.

Jacobsen et al., Design of the Utah/M.I.T. Dextrous Hand, IEEE International Conference on Robotics and Automation, 1986, pp. 1520-1532, Institute of Electrical and Electronics Engineers, Piscataway, New Jersey.

Jacobsen et al., Development of the Utah Artificial Arm, IEEE Transactions on Biomedical Engineering, Apr. 1982, pp. 249-269, vol. BME-29, No. 4, Institute of Electrical and Electronics Engineers, Piscataway, New Jersey.

Jacobsen et al., Research Robots for Application in A1, Teleoperation and Entertainment, Proceedings of the International Fluid Power Exposition and Technical Conference, Mar. 24-24, 1992, pp. 1-19, Chicago, Illinois.

Jacobsen et al., Research Robots for Applications in Artificial Intelligence, Teleoperation and Entertainment; The International Journal of Robotics Research; Apr.-May 2004, pp. 319-330, vol. 23, No. 4-5, SAGE Publications, Thousand Oaks, California.

Jacobsen, Science, Robotics, and Superheroes, Presented at Department of Science University of Utah Science at Breakfast, Mar. 17, 2010, 16 pages.

Jafari et al., A Novel Actuator with Adjustable Stiffness (AwAS), Oct. 18-22, 2010, 6 pages, IEEE/RSJ International Conference on Intelligent Robots and Systems, Taiwan.

Jansen et al., Exoskeleton for Soldier Enhancement Systems Feasibility Study, Sep. 2000, 44 pages, Oak Ridge National Laboratory, Oak Ridge, Tennessee.

Kazerooni, Berkeley Lower Extremity Exoskeleton (BLEEX), to the best of applicant's knowledge article was available before the application filing date, 3 pages, University of California, Berkeley, Berkeley, California.

Kim, Development of a small 6-axis force/moment sensor for robot's fingers, Measurement Science and Technology, Sep. 30, 2004, 2 pages, Issue 11, Institute of Physics and IOP Publishing Limited.

Kim et al., A Force Reflected Exoskeleton-Type Masterarm for Human-Robot Interaction, IEEE Transactions on Systems, Man and Cybertentics—Part A: Systems and Humans, Mar. 2005, pp. 198-212, vol. 35, No. 2, Institute of Electrical and Electronics Engineers, Piscataway, New Jersey.

Kulick, An Unpowered Exoskeleton Springs Into Action: Researchers Increase Walking Efficiency, http://www.cmu.edu/me/news/archive/2015/collins-clutch.html, Apr. 1, 2015, 2 pages, Carnegie Mellon University Mechanical Engineering, Pittsburgh, Pennsylvania.

Laliberte et al., Underactuation in Space Robotic Hands, Proceeding of the 6th International Symposium on Artificial Intelligence and Robotics & Automation in Space, Jun. 18-22, 2001, 8 pages, Canadian Space Agency, Canada.

Magnetic Base, www.ask.com/wiki/magnetic_base; page last updated Sep. 12, 2012, 2 pages, retrieved from www.ask.com/wiki/magnetic_base.

Miao et al., Mechanical Design of Hybrid Leg Exoskeleton to Augment Load-Carrying for Walking, International Journal of Advanced Robotic Systems, Mar. 28, 2013, 11 pages, vol. 10, Intech open science open minds, Europe.

Mirfakhrai et al., Polymer artificial muscles, materialstoday, Apr. 2007, pp. 30-38, vol. 10 No. 4, Elsevier, Netherlands.

Mombaur et al., HEiKA-EXO: Optimization-based development and control of an exoskeleton for medical applications, http://typo.iwr.uni-heidelberg.de/groups/orb/research/heika-exo/, Optimization in Robotics & Biomechanics, Oct. 20, 2014, 3 pages, Germany.

Moosavian et al., Dynamics Modeling and Tip-Over Stability of Suspended Wheeled Mobile Robots with Multiple Arms, 2007 IEEE/RSJ International Conference on Intelligent Robots and Systems, Oct. 29-Nov. 2, 2007; pp. 1210-1215, Institute of Electrical and Electronics Engineers, Piscataway, New Jersey.

Newport Corporation, Heavy-Duty Magnetic Base, 300 lb (1334 N) Holding Force, ¼-20 Thread, http://search.newport.com/?q=* &x2= sku&g2=200, as accessed Apr. 23, 2011, 1 page, Irvine, CA.

Oak Ridge National Laboratory, Foot Force-Torque Sensor Novel Sensor for Measuring Forces and Torques at the Foot, www.oral.gov, to the best of applicant's knowledge article was available before the application filing date, 1 page, Oak Ridge National Laboratory, Oak Ridge, Tennessee.

Omega, Load Cell Designs, www.omega.com/literature/transactions/volume3/load3.html, Nov. 1, 2005, 3 pages.

Ostling, Wearable Robots, Technology Review, Jul./Aug. 2004, pp. 70-73, Elizabeth Bramson-Boudreau, Cambridge, Massachusetts.

Pan, Improved Design of a Three-degree of Freedom Hip Exoskeleton Based on Biomimetic Parallel Structure, Jul. 2011, 132 pages, University of Ontario Institute of Technology, Canada.

Pelrine et al., Electrostriction of polymer dielectrics with compliant electrodes as a means of actuation, Sensors and Actuators A: Physical, Jan. 1998, pp. 77-85, vol. 64 Issue 1, Elsevier, Netherlands.

Pelrine et al., High-field deformation of elastomeric dielectrics for actuators, Materials Science and Engineering, Nov. 28, 2000, pp. 89-100, vol. 11 Issue 2, Elsevier, Netherlands.

Pelrine et al., Dielectric Elastomer Artificial Muscle Actuators: Toward Biomimetic Motion, Proceedings of SPIE—The International Society for Optical Engineering, Jul. 2002, pp. 126-137, vol. 4695, SPIE, Bellingham, WA.

Pin, Wearable Robotics Presented to New Horizons in Science Briefing, Oct. 2003, 34 pages, Knoxville, Tennessee.

Pratt et al., The RoboKnee: An Exoskeleton for Enhancing Strength and Endurance During Walking, International Conference on Robotics & Automation, Apr. 2004, 6 pages, IEEE, New Orleans, LA.

Robotics Research Group, Degrees of Freedom, www.robotics.utexas.edu/rre/learn_more/low_ed/dof/, Oct. 25, 2006, 2 pages, University of Texas.

Rouse et al., Clutchable Series-Elastic Actuator: Design of a Robotic Knee Prosthesis for Minimum Energy Consumption, 2013 IEEE 13th International Conference on Rehabilitation Robotics (ICORR), Jun. 24-26, 2013, 6 pages, Institute of Electrical and Electronics Engineers, Piscataway, New Jersey.

Schuler et al., Dextrous Robot Arm, In Proceedings of the $8^{th}$ ESA Workshop on Advanced Space Technologies for Robotic and Automation 'ASTRA 2004' ESTEC, Nov. 2-4, 2004, 8 pages, Noordwijk, The Netherlands.

Searchmap Blog, Scientists Develop Mechanical Spring-Loaded Leg Brace to Improve Walking, http://www.searchmap.eu/blog/scientists-develop-mechanical-spring-loaded-leg-brace-to-improve-walking/, Apr. 1, 2015, 5 pages, Searchmap Blog.

Seppala, These exoskeleton heels could help stroke victims walk again, https://www.engadget.com/2015/04/02/feet-exoskeletons/, Apr. 2, 2015, Engadget, San Francisco, California.

Shamaei et al., Estimation of Quasi-Stiffness of the Human Knee in the Stance Phase of Walking, Mar. 22, 2013, 10 pages, vol. 8 Issue 3, PLOS One, San Francisco, California.

Siddharth et al., Design and Analysis of a 1-DOF Walking Mechanism, http://siddharthswaminathan.in/files/WalkingMechanism.pdf, Nov. 2012, 7 pages, India.

Smith et al., Integrated thin-film piezoelectric traveling wave ultrasonic motors, Sensors and Actuators A: Physical, Dec. 2012, pp. 305-311, vol. 188, Elsevier, Netherlands.

Song et al., Kinematics Analysis and Implementation of a Motion-Following Task for a Humanoid Slave Robot Controlled by an Exoskeleton Master Robot, International Journal of Control, Automation and Systems, Dec. 2007, pp. 681-690, vol. 5, No. 6, Korean Institute of Electrical Engineers, South Korea.

(56) References Cited

OTHER PUBLICATIONS

Suitx, Phoenix Medical Exoskeleton, https://www.suitx.com/phoenix-medical-exoskeleton, 3 pages, to the best of the applicant's knowledge article was available before the application filing date, US Bionics, Inc., Berkeley, California.

Suleiman, Engineering an affordable exoskeleton, Phys.org, https://phys.org/news/2014-06-exoskeleton.html, Jun. 12, 2014, 5 pages, Science X Network.

Tmsuk, Rescue Robot "T-53" release Control Technologies to Control the Synchronous Operation of the Arm, http://robot.watch.impress.co.jp/cda/news/2007/07/18/564.html, as accessed Sep. 1, 2011 5 pages, Robot Watch website.

Ueda et al., Large Effective-Strain Piezoelectric Actuators Using Nested Cellular Architecture With Exponential Strain Amplification Mechanisms, IEEE/ASME Transactions on Mechatronics, Oct. 2010, pp. 770-782, vol. 15 Issue 5, Institute of Electrical and Electronics Engineers, Piscataway, New Jersey.

Vanderborght et al., Variable impedance actuators: A review, Robotics and Autonomous Systems, Dec. 2013, 14 pages, vol. 61, Issue 12, Elsevier, Netherlands.

Walsh, Biomimetic Design of an Under-Actuated Leg Exoskeleton For Load-Carrying Augmentation, Massachusetts Institute of Technology, Feb. 2006, 97 pages, Massachusetts.

Walsh et al., A Quasi-Passive Leg Exoskeleton for Load-Carrying Augmentation, International Journal of Humanoid Robotics, Mar. 8, 2007, 20 pages, vol. 4, No. 3, World Scientific Publishing Company.

Wang et al., A highly-underactuated robotic hand with force and joint angle sensors, 2011 IEEE/RSJ International Conference on Intelligent Robots and Systems, Sep. 25-30, 2011, 6 pages, Institute of Electrical and Electronics Engineers, Piscataway, New Jersey.

Yeates, Utah-built robot safeguards the workplace, http://www.ksl.com?nid=148&sid=17654421&autostart=y; Oct. 13, 2011, 3 pages, KSL Broadcasting, Salt Lake City, Utah.

Yip et al., High-Performance Robotic Muscles from Conductive Nylon Sewing Thread, 2015 IEEE International Conference on Robotics and Automation (ICRA), May 26-30, 2015, 6 pages, Seattle, Washington.

Zubrycki et al., Novel haptic glove-based interface using jamming principle, Proceedings of the $10^{th}$ International Workshop on Robot Motion and Control, Jul. 6-8, 2015, 6 pages, IEEE, Poland.

David et al., Study of an External Passive Shock-absorbing Mechanism for Walking Robots, $8^{th}$ IEEE International Conference on Humanoid Robots, Dec. 1-3, 2008, pp. 435-440, Institute of Electrical and Electronics Engineers, Piscataway, New Jersey.

Kaslin et al., Towards a Passive Adaptive Planar Foot with Ground Orientation and Contact Force Sensing for Legged Robots, IEEE International Conference on Intelligent Robots and Systems, Oct. 1-5, 2018, pp. 2707-2714, Institute of Electrical and Electronics Engineers, Piscataway, New Jersey.

Liu et al., Cat-inspired Mechanical Design of Self-Adaptive Toes for a Legged Robot, IEEE International Conference on Intelligent Robots and Systems, Oct. 9-14, 2016, pp. 2425-2430, Institute of Electrical and Electronics Engineers, Piscataway, New Jersey.

Liu et al., Concept and Design of a Lightweight Biped Robot for Walking on Rough Terrain, IEEE International Conference on Robotics and Biomimetics, 2017, 6 pages, Institute of Electrical and Electronics Engineers, Piscataway, New Jersey.

\* cited by examiner

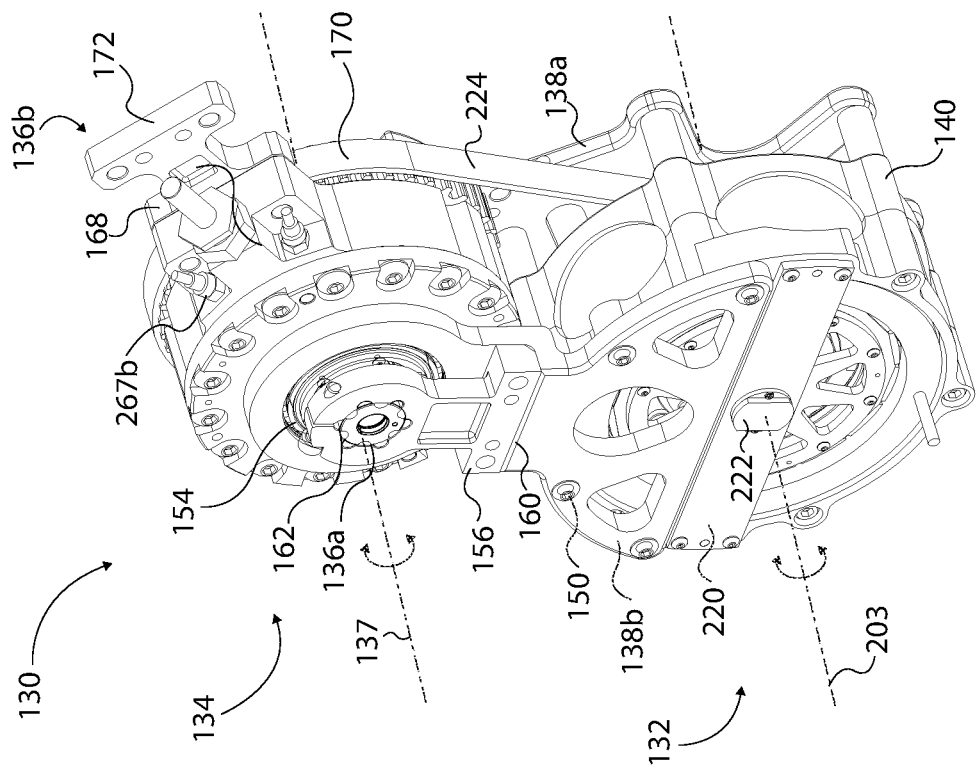
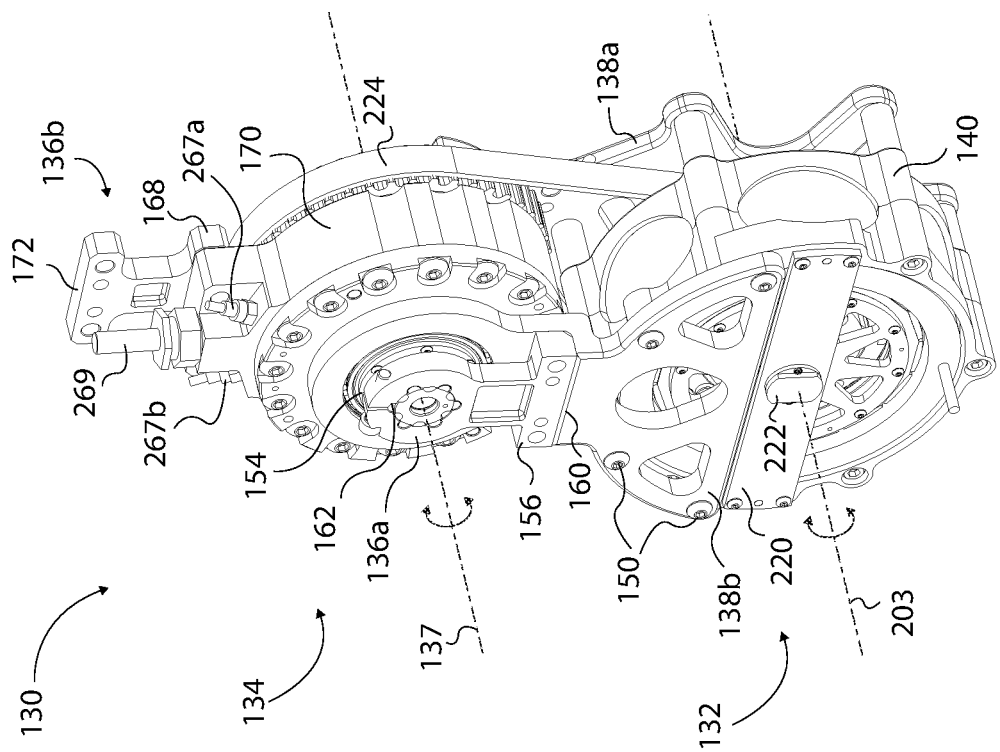

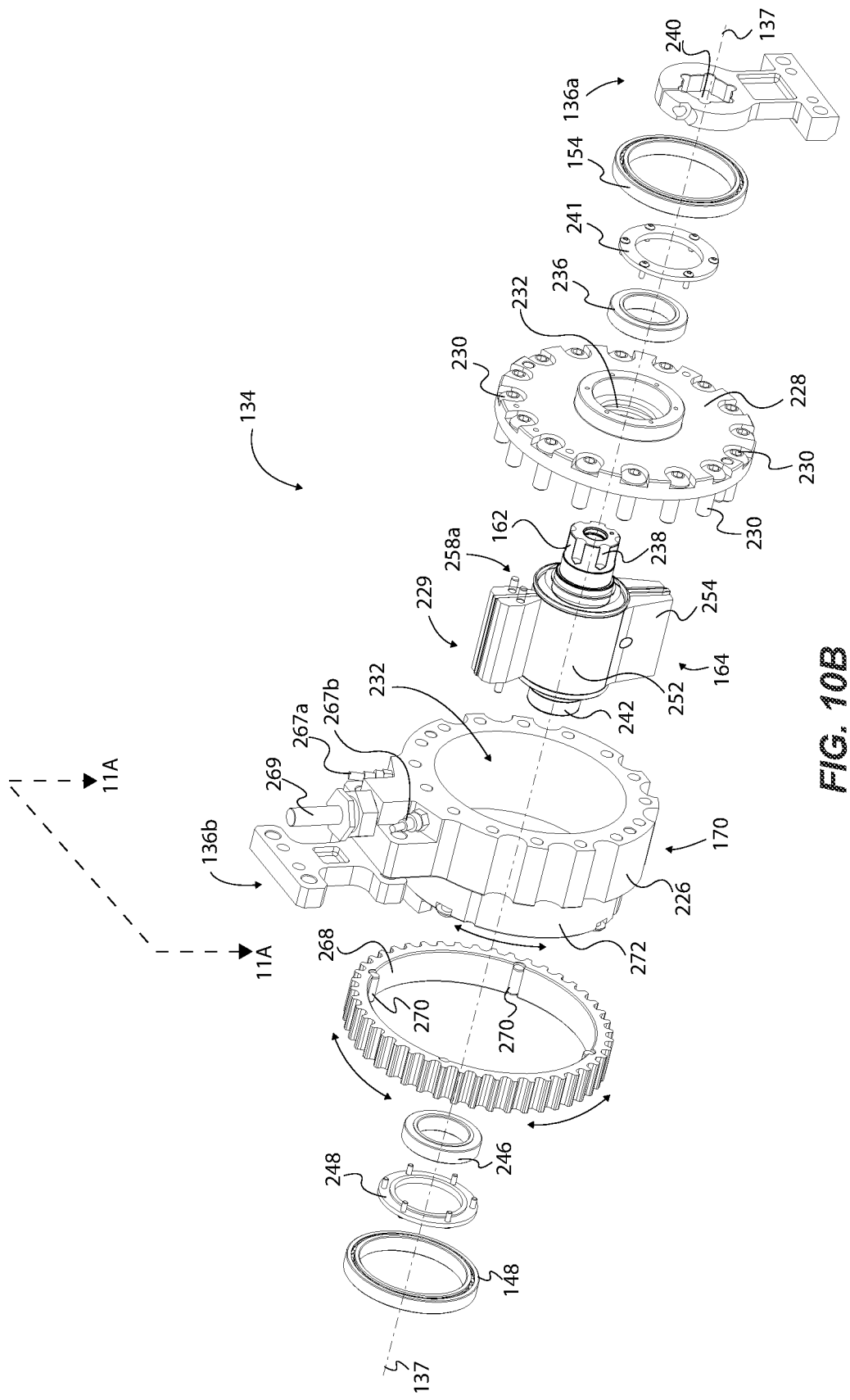

TUNABLE ACTUATOR JOINT MODULES HAVING ENERGY RECOVERING QUASI-PASSIVE ELASTIC ACTUATORS WITH INTERNAL VALVE ARRANGEMENTS

RELATED APPLICATIONS

This is a divisional application of U.S. application Ser. No. 15/810,119, filed Nov. 12, 2017, entitled "Tunable Actuator Joint Modules Having Energy Recovering Quasi-Passive Elastic Actuators with Internal Valve Arrangements" which claims the benefit of U.S. Provisional Application Ser. No. 62/421,175, filed Nov. 11, 2016, and entitled, "Tunable Energy Recovering Quasi-Passive Actuators" each of which is incorporated by reference in its entirety herein.

BACKGROUND

A wide variety of exoskeleton, humanoid, robotic arms, and other robots and robotic systems exist, many of which seek the most efficient operation possible. One fundamental technical problem that continues to be a focus is how such systems, such as where energetic autonomy is concerned, can minimize power consumption while still providing acceptable levels of force output. Indeed, power remains an inevitable challenge in the world of robotics. Designers of such systems typically attempt to optimize operation based on the intended use or application. In many cases, either power or efficiency is sacrificed, at least to some extent. For instance, some robotic systems employ high-output power systems that can meet the force output demands of the robotic system, putting this ahead of any efficiency considerations. On the other hand, some robotic systems employ more efficient power systems in an attempt to improve efficiency, with force output being a secondary consideration. High output force or power systems, while capable of performing various tasks, can be costly. Moreover, such systems often are tethered to a power source as portable power remains limited in its capabilities. Efficient, yet low force output systems can lack practicality, inasmuch as many robotic systems are designed to assist humans in work related or other tasks that require a certain level of force in order to perform the task(s). Overall, the power issue has been a challenging obstacle with various efforts being made to maximize output while minimizing power consumption. Even small advances in this ratio of power to output energy consumption area can be highly beneficial. While much research and development is ongoing to improve power sources, another way robotic systems can improve the power to energy output ratio is through the structural build of the robotic system, namely the way various components are configured, how these are controlled, and if the systems can take advantage of naturally occurring phenomenon, such as gravity.

BRIEF SUMMARY OF THE INVENTION

An initial summary of the disclosed technology is provided here. Specific technology examples are described in further detail below. This initial summary is intended to set forth examples and aid readers in understanding the technology more quickly, but is not intended to identify key features or essential features of the technology nor is it intended to limit the scope of the claimed subject matter.

The present disclosure sets forth a quasi-passive elastic actuator operable within a robotic system, comprising a housing comprising an output member operable to couple to a first support member of a robotic system; a first vane device supported by the housing and comprising an input member operable to couple to a second support member of the robotic system; a second vane device coupled to the housing and interfaced with the first vane device, the first vane device and second vane device being rotatable relative to each other within the housing and defining, at least in part, a compression chamber and an expansion chamber; and a valve assembly operable to switch the quasi-passive elastic actuator between an elastic state and an inelastic state, and comprising a valve device disposed through an opening of the first vane device along an axis of rotation of the first vane device, the valve assembly defining, at least in part, a shunt circuit that facilitates fluid flow between the compression and expansion chambers through the valve assembly.

The present disclosure further sets forth a robotic system for a robotic limb configured to recover energy for minimizing power consumption of the robotic system, comprising a first support member; a second support member; and a quasi-passive elastic actuator rotatably coupling the first and second support members to define a joint of the robotic system rotatable about an axis of rotation defining a degree of freedom, the quasi-passive elastic actuator comprising a housing coupled to the first support member; a first vane device supported by the housing and coupled to the second support member; a second vane device coupled to the housing and interfaced with the first vane device, the first vane device and second vane device being rotatable relative to each other within the housing and defining, at least in part, a compression chamber and an expansion chamber; a valve assembly located and operable at the joint of the robotic system, the valve assembly comprising a valve device disposed through an opening of the first vane device along the axis of rotation; and a shunt circuit facilitating fluid flow between the compression and expansion chambers through the valve assembly, wherein the valve assembly is operable to position the valve device in an open position to open the shunt circuit to permit fluid flow between the compression and expansion chambers, thereby placing the quasi-passive elastic actuator in an inelastic state, and wherein the valve assembly is operable to position the valve device in a closed position to close the shunt circuit to restrict fluid flow between the compression and expansion chambers, thereby placing the quasi-passive elastic actuator in an elastic state, the quasi-passive elastic actuator being operable in the elastic state to store and release energy and to apply an augmented torque to rotate the first support member relative to the second support member.

The present disclosure also sets forth a method of facilitating switching of a quasi-passive elastic actuator of a tunable actuator joint module of a robotic system between an inelastic state and an elastic state, the method comprising configuring a quasi-passive elastic actuator to be operable with a primary actuator of the tunable actuator joint module to selectively apply an augmented torque to assist the primary actuator in rotation of a joint of the tunable actuator joint module about an axis of rotation; configuring an elastic component of the quasi-passive actuator to comprise a first vane device and second vane device rotatable relative to each other within a housing, the first vane device and second vane device defining, at least in part, a compression chamber and an expansion chamber; supporting a valve assembly about the axis of rotation of the joint through the first vane device; and configuring a shunt circuit to facilitate fluid flow between the compression and expansion chambers through the valve assembly.

BRIEF DESCRIPTION OF THE DRAWINGS

Features and advantages of the invention will be apparent from the detailed description which follows, taken in conjunction with the accompanying drawings, which together illustrate, by way of example, features of the invention; and, wherein:

FIG. 6A is an isometric view of a tunable actuator joint module operable with the robotic assemblies of FIG. 1 or 4A, in accordance with an example of the present disclosure;

FIG. 6B is an isometric view of the tunable actuator joint module of FIG. 6A in an actuated position;

FIG. 10B is a partially exploded front view of the quasi-passive elastic actuator of the tunable actuator joint module of FIG. 6A;

Reference will now be made to the exemplary embodiments illustrated, and specific language will be used herein to describe the same. It will nevertheless be understood that no limitation of the scope of the invention is thereby intended.

DETAILED DESCRIPTION

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

Figure 1:
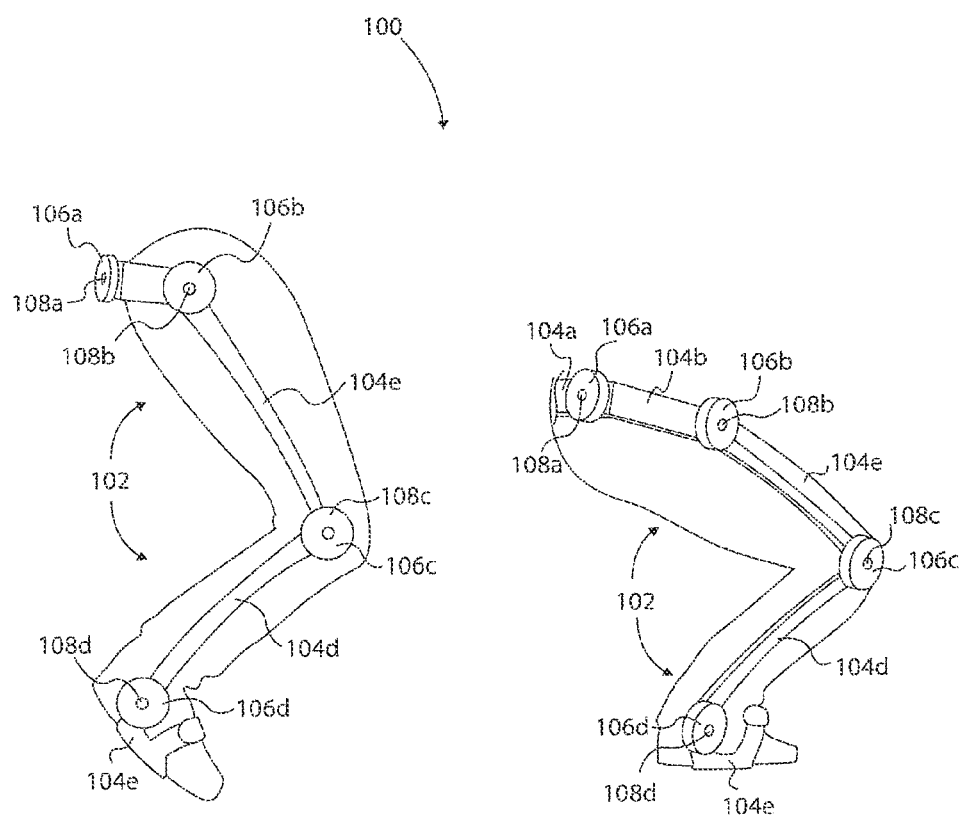
FIG. 1 illustrates two positions of a robotic assembly in the form of a lower portion of an exoskeleton having at least one tunable actuator joint module in accordance with an example of the present disclosure.

One example of a robotic assembly 100 is generically illustrated in FIG. 1. The robotic assembly 100 is shown in the form of an exoskeleton, and particularly a lower exoskeleton wearable by a user about the lower body. However, this is not intended to be limiting in any way as the concepts discussed herein can be applicable to and incorporated into or implemented with various types of robotic devices, such as exoskeletons (both upper and lower exoskeletons), humanoid robots or robotic devices, teleoperated robots or robotic devices, robotic arms, unmanned ground robots or robotic devices, master/slave robots or robotic devices (including those operable with or within a virtual environment), and any other types as will be apparent to those skilled in the art.

Figure 4A:
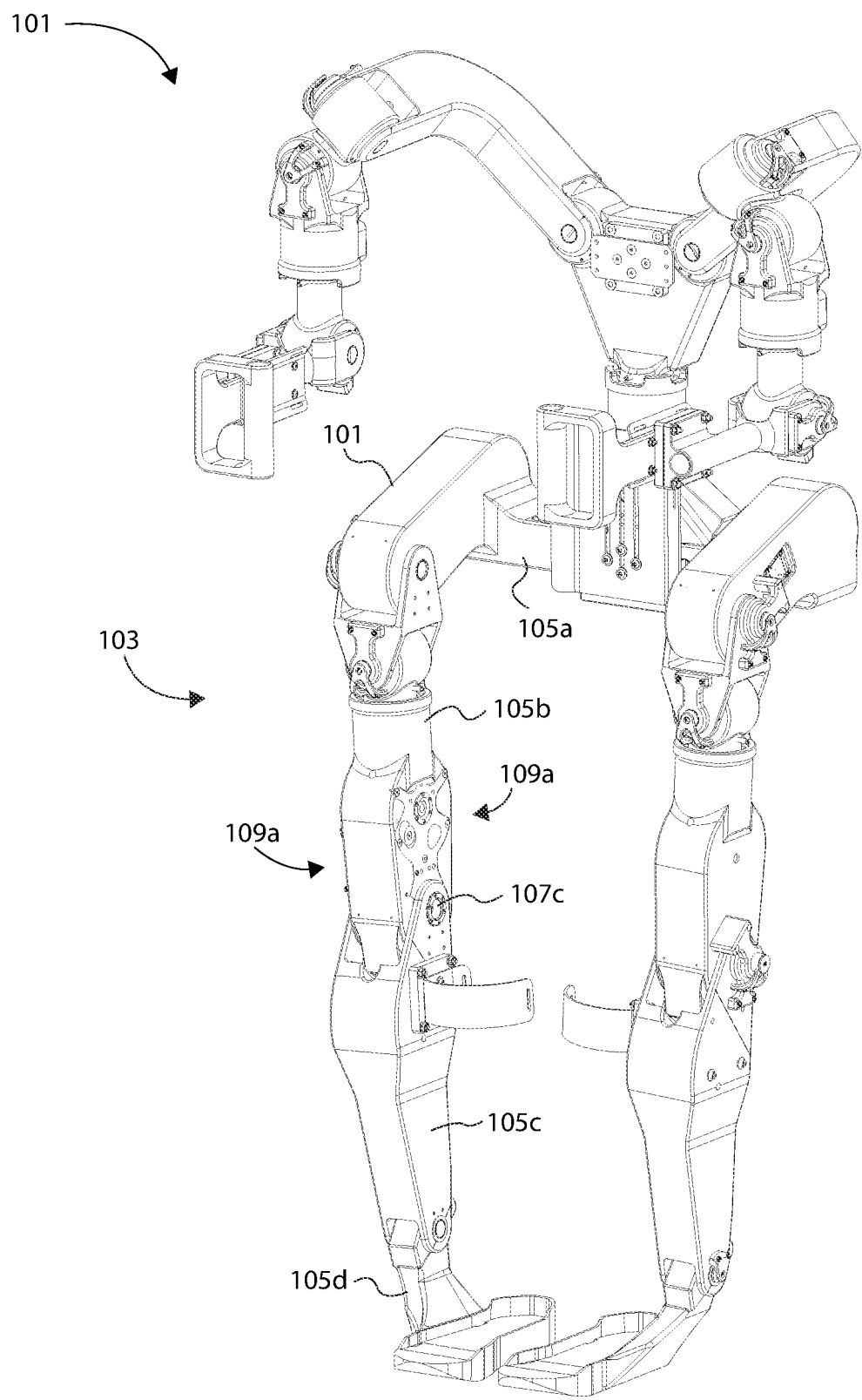
FIG. 4A is an isometric view of a robotic assembly, namely a wearable robotic exoskeleton, having at least one tunable actuator joint module in accordance with an example of the present disclosure.

In the example of the robotic assembly 100, the exoskeleton as disclosed herein can be configured as a full-body exoskeleton (i.e., similar to the exoskeleton having both a lower body portion and upper body portion, see FIG. 4A), or as only a lower body exoskeleton (i.e., some or all of the lower body portion), or as only an upper body exoskeleton (i.e., some or all of the upper body portion).

The robotic assembly 100 can comprise a plurality of tunable actuator joint modules having a quasi-passive elastic actuator. The upper extremity quasi-passive elastic actuators can have a different function from the lower extremity quasi-passive elastic actuators, or they can function similarly. For example, the lower extremity quasi-passive elastic actuators can provide an energy recovery mechanism during a portion of cyclic motions such as walking or running, and an ability to swing freely during other parts of the cycle or for other activities. Upper extremity quasi-passive elastic actuators can provide passive gravity compensation when the arms are raised to support armor and/or weapon masses. In both cases, the quasi-passive elastic actuators function to reduce the demand on the power supply, and on the primary actuators that may be used to do work in parallel with the quasi-passive elastic actuators. It is noted that, in example robotic systems, such as those described herein, the types of quasi-passive actuators used within the different joints and corresponding tunable actuator joint modules can be the same or different. Using the example of the robotic assembly 100, different quasi-passive elastic actuators can be used between the upper and lower extremities of the robotic system 100, or between the various tunable actuator joint modules within the upper extremity (the same being the case with the lower extremity), or between various tunable actuator joint modules within the same limb.

The example elastic actuators described herein can be referred to as quasi-passive elastic actuators as they are operable in active and inactive states or modes of operation (as compared to being entirely passive elastic actuators that are always either storing energy or releasing energy during all rotational movements of a joint, or other movements of a mechanical system). In examples described herein, passive and inactive modes or states of operation can be selectable or controllable and even dynamically selectable or controllable (e.g., selectable in real-time), as well as repeatedly switched from one state or mode to another state or mode, during operation of the robotic system. Depending upon the configuration of the tunable actuator joint module, example quasi-passive elastic actuators can comprise a first active state (sometimes referred to herein as an "elastic state") in which the quasi-passive elastic actuator can be actuated to store and release energy during various rotations of a joint of the robotic system, a second passive state (sometimes referred to herein as an "inelastic state") in which the quasi-passive elastic actuator can be made inactive, such that energy is neither stored nor released during various rotations of the joint, and in some cases a third semi-active or partially active state (sometimes referred to herein as a "semi-elastic state") in which the quasi-passive elastic actuator can be partially actuated to store and release energy during various rotations of the joint. In some example robotic systems, the quasi-passive elastic actuator can be switchable between the different modes or states of operation as needed or desired depending on, for example, needed or desired tasks and corresponding rotation movements, various torque or load requirements of the one or more joints of the robotic system, or needed or desired braking forces.

In some examples, the robotic assembly 100 can comprise left and right exoskeleton limbs (note that only the right exoskeleton limb 102 is shown in FIG. 1). The exoskeleton limb 102 can comprise a plurality of support members 104a-d (e.g., the rigid, structural supports that extend between the joints within the limb of the exoskeleton, or that link the joints together, much like the bones in the human body extending between the joints). The support members 104a-d can be coupled together for relative movement about a plurality of joints, such as tunable actuator joint modules 106a-d, defining a plurality of degrees of freedom about respective axes of rotation 108a-d. The rotational degrees of freedom about the axes of rotation 108a-d can correspond to one or more degrees of freedom of the human leg. For example, the rotational degrees of freedom about the axes 108a-d can correspond, respectively, to hip abduction/adduction, hip flexion/extension, knee flexion/extension, and ankle flexion/extension, respectively. Similarly, although not shown, degrees of freedom about respective axes of rotation within an upper body exoskeleton can correspond to one or more degrees of freedom of a human arm. For example, the degrees of freedom about the axes of rotation can correspond to shoulder abduction/adduction, shoulder flexion/extension, shoulder medial/lateral rotation, elbow flexion/extension, wrist pronation/supination, and wrist flexion/extension. A degree of freedom corresponding to wrist abduction/adduction can also be included, as desired.

A human user or operator may use or interact with the exoskeleton robotic assembly 100 (or 101 of FIG. 4A) by interfacing with the robotic assembly 100. This can be accomplished in a variety of ways as is known in the art. For example, an operator may interface with the robotic assembly 100 by placing his or her foot into a foot portion of the assembly, where the foot of the operator can be in contact with a corresponding force sensor. Portions of the human operator can also be in contact with other force sensors of the exoskeleton robotic assembly 100 located at various locations of the robotic assembly 100. For example, a hip portion of the robotic assembly 100 can have one or more force sensors configured to interact with the operator's hip. The operator can be coupled to the robotic assembly 100 by a waist strap or other appropriate coupling device. The operator can be further coupled to the robotic assembly 100 by a foot strap or other securing mechanism. In one aspect, various force sensors can be located about a hip, knee or ankle portion of the robotic assembly 100, corresponding to respective parts of the operator. While reference is made to sensors disposed at specific locations on or about the robotic assembly 100, it should be understood that position or force sensors, or both, can be strategically placed at numerous locations on or about the robotic assembly 100 in order to facilitate proper operation of the robotic assembly 100.

As a general overview, tunable actuator joint modules 106a-d can be associated with various degrees of freedom of the exoskeleton to provide forces or torques to the support members in the respective degrees of freedom. Unlike traditional exoskeleton systems and devices, the robotic assembly 100 can be configured, such that each tunable actuator joint module is configured to recover energy, which can reduce complexity and power consumption of the robotic assembly 100. For example, the tunable actuator joint module 106c, which defines a degree of freedom corresponding to a degree of freedom of knee flexion/extension, can be configured to recover energy during a first gait movement and then release such energy during a second gait movement to apply an augmented torque to assist a primary actuator providing a primary torque in rotation of the joint about the degree of freedom (and in parallel with the torque applied by the primary actuator of the tunable actuator joint module 106c, as discussed below). The tunable actuator joint module 106c can be selectively controlled, such that the quasi-passive elastic actuator can be engaged (i.e., caused to enter an operating state or condition in which the elastic actuator is operable and enabled to store and release energy (an elastic or semi-elastic state)) and disengaged from operation (i.e., caused to enter an operating state or condition or configuration where it neither stores nor releases energy (an inelastic state)) during joint rotation, or where any previously stored energy can be dissipated or released. In the inelastic state, the joint "freely swings" with negligible resistance to rotate the joint as the operator walks or runs, for instance. By operating in parallel with the primary actuator (e.g., a primary motor operable to actuate the joint), the quasi-passive elastic actuator can provide or apply an augmented torque in parallel with the torque provided by the primary actuator (i.e., a torque that is added to the torque generated by the primary actuator), or a braking force.

The quasi-passive elastic actuator can comprise a compact internal valve, such as a two-way valve, that can be controlled and operated to change the modes of the quasi-passive actuator, namely to switch between an elastic state (where the actuator acts as a spring for transient energy storage and recovery), a semi-elastic state (where the actuator acts as a spring partially compressed), and an inelastic state (where the actuator employs a shunting function that allows the actuator to move freely (i.e., not to store or release energy) (except for friction and movement of fluid through the valve). Moreover, the tunable actuator joint module 106c can be "tuned" to comprise a desired stiffness, as further discussed below. Thus, the magnitude of stiffness for a given joint is adjustable for mission specific payloads and terrain-specific gaits while the active valve controls exactly when that stiffness is engaged for energy recovery during the support phase and when it is disengaged during the free swinging phase.

The result is effectively a quasi-passive elastic mechanism that, in one advantage, is selectively operable to recover energy (e.g., energy lost during some gait motions) to reduce or minimize power consumption required to actuate the joint. Therefore, when combining a plurality of tunable actuator joint modules within a robotic assembly, such as the lower body exoskeleton shown in FIG. 1, for example, a significant amount of energy can be recovered and utilized during movement (via hip, knee, and ankle joints), which can reduce weight, size, complexity, and overall power consumption of the exoskeleton. A quasi-passive actuator for energy recovery can comprise an elastic component, for example, either a mechanical or pneumatic or hydraulic element, that is capable of storing and releasing energy to the joint, and, optionally, an active switch or clutch capable of engaging and disengaging the elastic component from the primary torque source powering the joint. Implicit in this energy recovery approach is the defining of the magnitude of elastic stiffness, as well as when to engage and disengage the elastic actuator during each gait cycle. These values can be optimized by searching for a stiffness, position offset, and temporal window that minimizes the average of the square of joint torques during the gait cycle. This numerical optimization, in essence, results in minimum average power consumption of a given primary joint torque actuator for a given gait or maneuver. The practical implementation of this approach for energy recovery and reduction of joint actuation torque thus leads to defining that angular stiffness which best works for the majority of time that the robotic assembly is to be used, e.g., walking vs. running, and establishing gait recognition algorithms that can be used to precisely engage and disengage the elastic actuator(s) over a broad range of activities.

The above general overview is explained in more detail below.

Figure 2A:
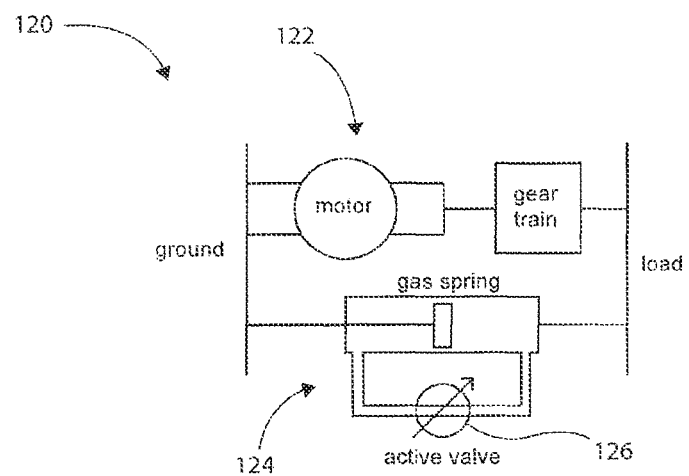
FIG. 2A is a schematic illustration of a tunable actuator joint module in accordance with an example of the present disclosure.
Figure 2B:
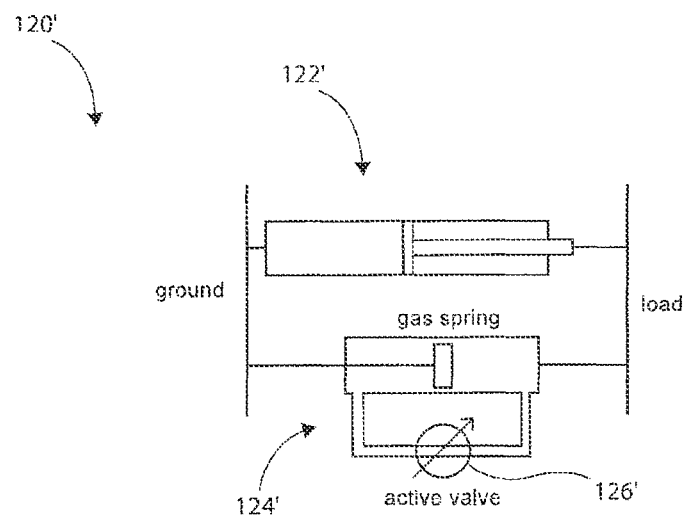
FIG. 2B is a schematic illustration of a tunable actuator joint module in accordance with an example of the present disclosure.

FIGS. 2A and 2B each schematically illustrate tunable actuator joint modules in accordance with two examples of the present disclosure. FIG. 2A shows a tunable actuator joint module 120 having a primary actuator 122 operable to provide a primary torque to the tunable actuator joint module 120. In one example, the primary actuator can comprise a geared motor (e.g., a primary actuator having an electric motor operable with a transmission, such as a planetary type of transmission (or any other type of transmission as will be appreciated by those skilled in the art), the primary actuator 122 operating in parallel with a quasi-passive elastic actuator 124 (e.g., a rotary or linear pneumatic (air or other gas) actuator, as will be discussed below), both operable to apply a torque, and in some states a torque in parallel, to a load (e.g., a torque to rotate a joint, or the support members rotatable about one another defining a joint, of a robotic assembly, as in FIGS. 1 and 4A).

The quasi-passive elastic actuator 124 can comprise a valve assembly 126, which can be configured as any of the valve assemblies described below as pertaining to FIGS. 14A-23. The valve assembly 126 can facilitate or can comprise at least part of a control system for the tunable actuator joint module 120, such that it is controllable to selectively facilitate the application of the augmented torque via the quasi-passive fluid actuator 124 in parallel with the torque applied by the geared motor 122.

In examples described herein, "selective" can mean that the tunable actuator joint module can be controlled in real-time at select times and for select durations as needed or desired, such as to vary a magnitude and timing of a braking force, vary a magnitude and timing of compression of the elastic component of the quasi-passive actuator and the storing and releasing of energy therein, or vary a magnitude and timing of a primary torque generated by the primary actuator depending upon different operating conditions, operating states, different demands of the robotic system, or as desired by the operator. Selective control can mean that the quasi-passive elastic actuator can be operated in conjunction with the primary actuator all or some of the time or for a desired duration of time. In addition, "selective" can mean that one or more operating parameters or the output performance of the valve assembly can be controlled and varied in real-time as needed or desired. Operating parameters or output performance can include, but is/are not limited to, a magnitude of the augmented torque to be applied, a magnitude of the braking force generated, the stiffness or elasticity of the elastic actuator, the zero or null point of actuation of the elastic actuator, and others.

In examples where the quasi-passive actuator is caused to enter a semi-elastic state or mode of operation, the quasi-passive elastic actuator can be actuated to partially compress the elastic or spring component of the quasi-passive elastic actuator to store, and be enabled to release, an amount of energy or enabled to generate a magnitude of a braking force that is less than what would otherwise be achieved if the quasi-passive elastic actuator were in a fully elastic state. Stated another way, semi-elastic describes that state in which there is a less than 1:1 transfer of energy or forces, due to rotation of the joint, to the quasi-passive elastic actuator coupled between the input and output members (e.g., because the valve assembly is partially open). "Semi-elastic," as used herein, is not intended to refer to the inherent elastic property (i.e., the elasticity) of the elastic component of the quasi-passive elastic actuator, but merely to a degree of compression of the elastic component.

FIG. 2B is similar to FIG. 2A, except that in this example of a tunable actuator joint module 120', the primary actuator 122' comprises a hydraulic actuator incorporated as a powered actuator to operate in parallel with the quasi-passive fluid actuator 124' of the tunable actuator joint module 120'.

Figure 3A:
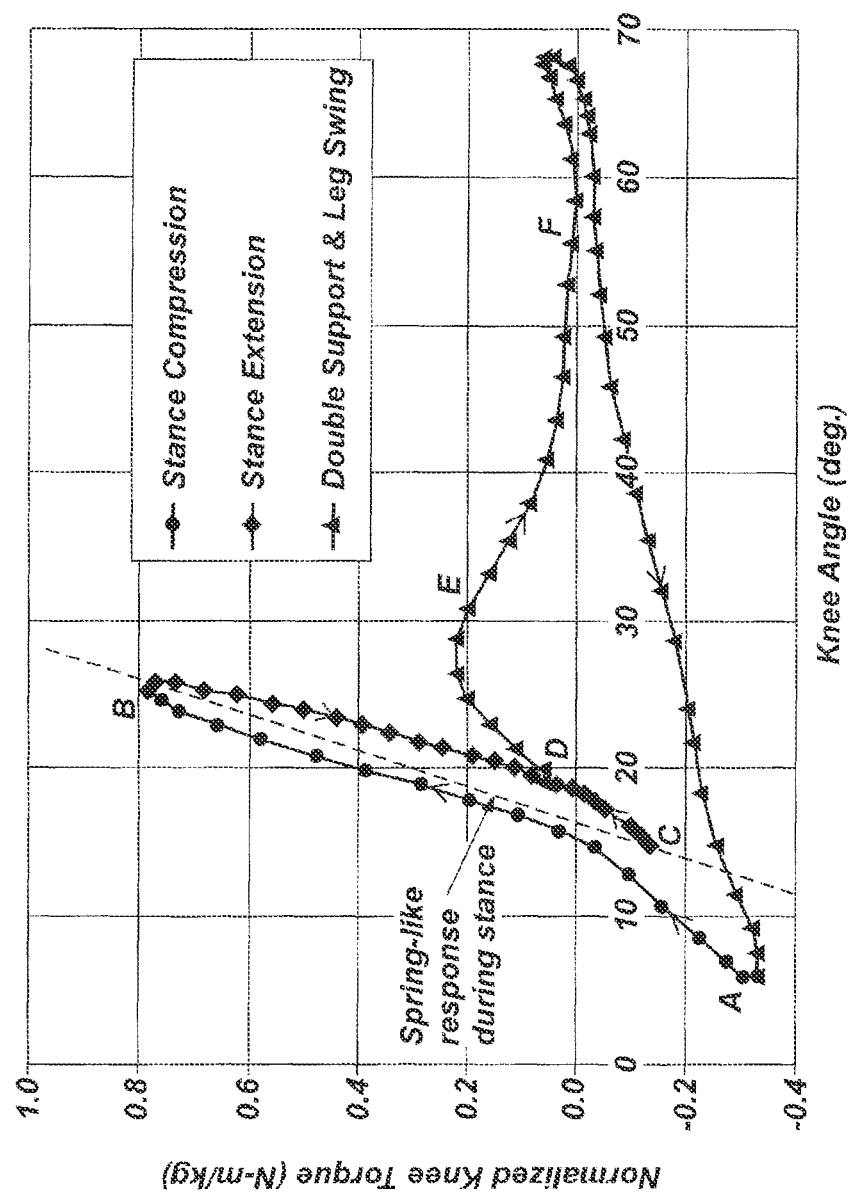
FIG. 3A is a graph illustrating human weight normalized knee joint torque vs. knee joint angle of a human gait cycle.

FIG. 3A is a graph showing joint torque vs. joint position as these occur during an example gait of a human, the graph showing the torque (N-m/kg) occurring in the joint relative to or as corresponding to the angle of rotation of the joint. This particular graph is illustrative of an example torque/angular rotation relationship of a human knee (without wearing an exoskeleton), while walking approximately 3 mph on a flat surface. A first gait movement from point A to point B illustrates stance compression following heel strike, a second gait movement from point B to C illustrates stance extension, with the stance phase being completed at point D. A third gait movement between points D, E, F, and A illustrates "double support and leg swing." Therefore, the "stance phase" is from heel strike (point A) to toe-roll/terminal stance (points A to D), where the torque-joint profile has a quasi-elastic behavior (walking and running are similar regarding this quasi-elastic stiffness). During this phase, the knee also acts as a shock absorber. The "swing phase" is from toe-off to heel strike (points E to A), and during this phase the knee exhibits a quasi-ballistic (passive dynamics) response with some damping during the final extension that occurs before heel strike (thus, the knee acts as a controlled damper or shock absorber).

This characteristic of the human gait is not unique to the knee joint, nor limited to the walking gait, and forms the basis for the tunable actuator joint modules discussed herein. Indeed, when reviewing the joint torque vs. position plots of simulated cyclical exoskeleton activities, such as walking, running, and step climbing, there are periods of time during these specific gait motions where elastic energy recovery can be exploited to reduce the requirement for motor torque to run the joint. Thus, the tunable actuator joint modules described herein can be configured to exploit the features of the natural motion of the hip, knee, and ankle, for instance, to minimize demands on powered actuators (e.g., electric-geared motors) to reduce overall power consumption within the robotics assembly. The tunable actuator joint modules discussed herein can also be incorporated into shoulder and elbow joints, for instance, but these may be more task-specific than as with the lower body joints, as further discussed below. However, the tunable actuator joint modules of lower joints (e.g., hip, knee, ankle) can also be configured to operate based on a specific task (e.g., lifting a load, sitting and standing, and others), rather than just a cyclical operation (e.g., walking or running).

Figure 3B:
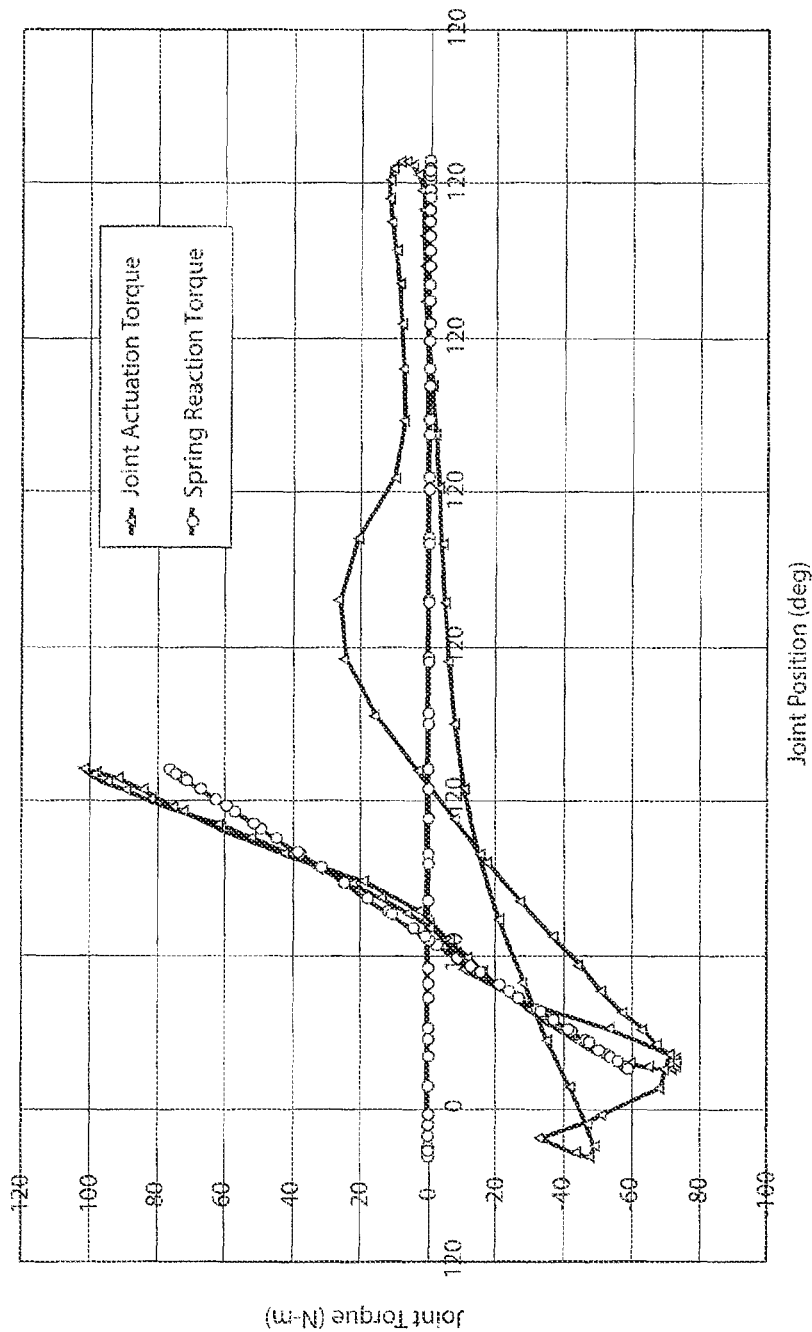
FIG. 3B is a graph illustrating the torque required to accomplish a joint trajectory and a portion of a gait where an elastic response can be created by a tunable actuator joint module in accordance with an example.

FIG. 3B is a graph showing an exoskeleton knee joint torque (N-m) vs. position (deg.) for walking at 3.5 mph with a 50 lb. payload. The plotted "triangular" labeled line ("joint actuation torque") represents the required overall torque to accomplish the prescribed joint trajectory, while the plotted "circular" labeled lines ("spring reaction torque") represents the part of the gait where an elastic response can by created by a quasi-passive elastic actuator of a tunable actuator joint module. Thus, this spring reaction torque can be exploited to reduce power consumption to actuate a joint, as further detailed below.

Figure 3C:
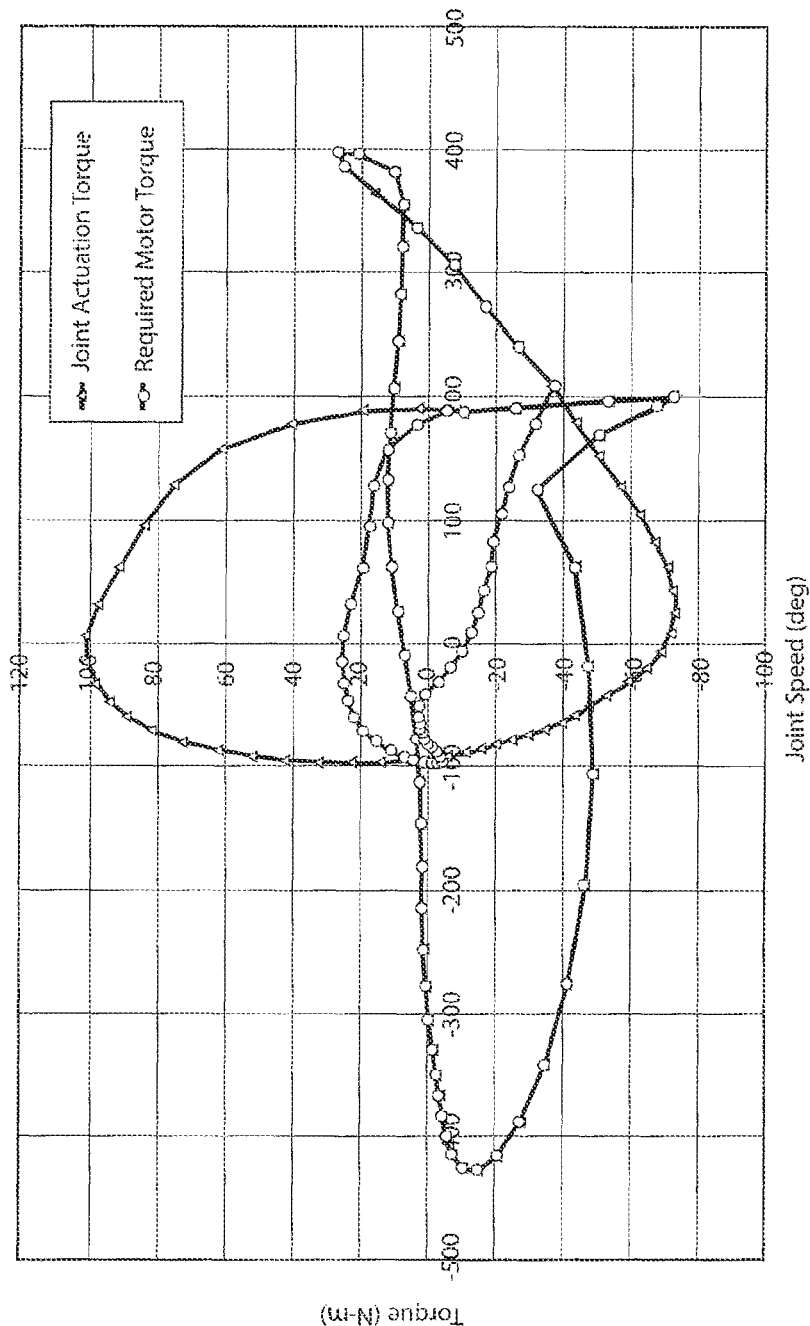
FIG. 3C is a graph illustrating performance of a tunable actuator joint module in accordance with an example.

FIG. 3C is a graph illustrating performance of an exoskeleton having a tunable actuator joint module with a quasi-passive elastic actuator operating in parallel with a primary actuator, the joint module having a joint stiffness of 7 N-m/degree, associated with the human knee joint, in one example. More specifically, the graph shows joint torque (N-m) vs. joint speed (deg./sec) for walking at 3.5 mph with a 50 lb. payload. The plotted "triangular" labeled line ("joint actuation torque") represents the required overall torque to accomplish the prescribed joint trajectory (e.g., the torque required to rotate a knee), while the plotted "circular" labeled lines ("spring reaction torque") represents the part of the gait where an elastic response can be created by engaging and disengaging the quasi-passive elastic actuator in a timely manner, as exemplified herein.

As illustrated by this "circular" labeled line, the resulting peak torque is substantially reduced (approximately 25 N-m) vs. the normalized torque requirement (approximately 100 N-m) of the "triangular" labeled line. That is, normally (i.e., without incorporating a tunable actuator joint module having an elastic actuator) the torque requirement is peaked at approximately 100 N-m; however, when incorporating a tunable actuator joint module having an elastic actuator as disclosed herein, the resulting peak torque can be only approximately 20 N-m, thus significantly reducing power requirements for the same gait cycle and operating conditions. This is because the tunable actuator joint module stores energy during a first gait movement (via the quasi-passive elastic actuator), and then releases that energy during a second gait movement to apply an augmented torque that can be applied in parallel with a torque applied by a primary actuator (e.g., a geared motor) of the tunable actuator joint module. Of course, other factors play a role in these results, such as weight, payload, etc. In any event, these graphs illustrate that much less on-board power is required by the powered motor to appropriately actuate a joint when used in conjunction with a selectively controllable quasi-passive elastic actuator, as further exemplified below. The use of a parallel elastic actuator effectively reduces the requirement for motor torque as the elastic actuator is engaged and disengaged in a timely manner, such as during specific phases of a gait cycle. Similar plots or graphs can be shown for hip joints, ankle joints, shoulder joints, and elbow joints. In some cases, the elastic actuator can be engaged full-time for the gaits of these joints.

For the sake of clarity, FIGS. 4A-5B and FIGS. 12A-12F pertain to a first example of a tunable actuator joint module (comprising a quasi-passive elastic actuator in the form of a rotary pneumatic actuator having a rotary pneumatic spring as the elastic component, the quasi-passive actuator being operable in an elastic state, a semi-elastic state, and an inelastic state). FIGS. 6A-11B pertain to a second example of a tunable actuator joint module (comprising a quasi-passive elastic actuator in the form of a rotary pneumatic actuator having a rotary pneumatic spring as the elastic component, the quasi-passive actuator being operable in an elastic state, a semi-elastic state, and an inelastic state). FIGS. 13A and 13B pertain to a third example of a tunable actuator joint module (comprising a quasi-passive elastic actuator in the form of a rotary pneumatic actuator having a rotary pneumatic spring as the elastic component, the quasi-passive actuator being operable in an elastic state, a semi-elastic state, and an inelastic state). FIGS. 14A-15C pertain to an example of a first vane or vane device and second vane or vane device operable with each of said first, second, and third example tunable actuator joint modules, as well as the case with the example first vane device of FIGS. 16A and 16B. FIGS. 17A-17E pertain to one example of a valve assembly operable with the first vane device of FIGS. 16A and 16B. Similarly, FIGS. 18A-18D pertain to another example of a valve assembly operable with the first vane device of FIGS. 16A and 16B. Finally, FIGS. 19A-23 pertain to various additional example valve assemblies operable with respective first vane devices, as described with corresponding examples below. The following discussion will cross-reference relevant Figures accordingly.

Figure 4B:
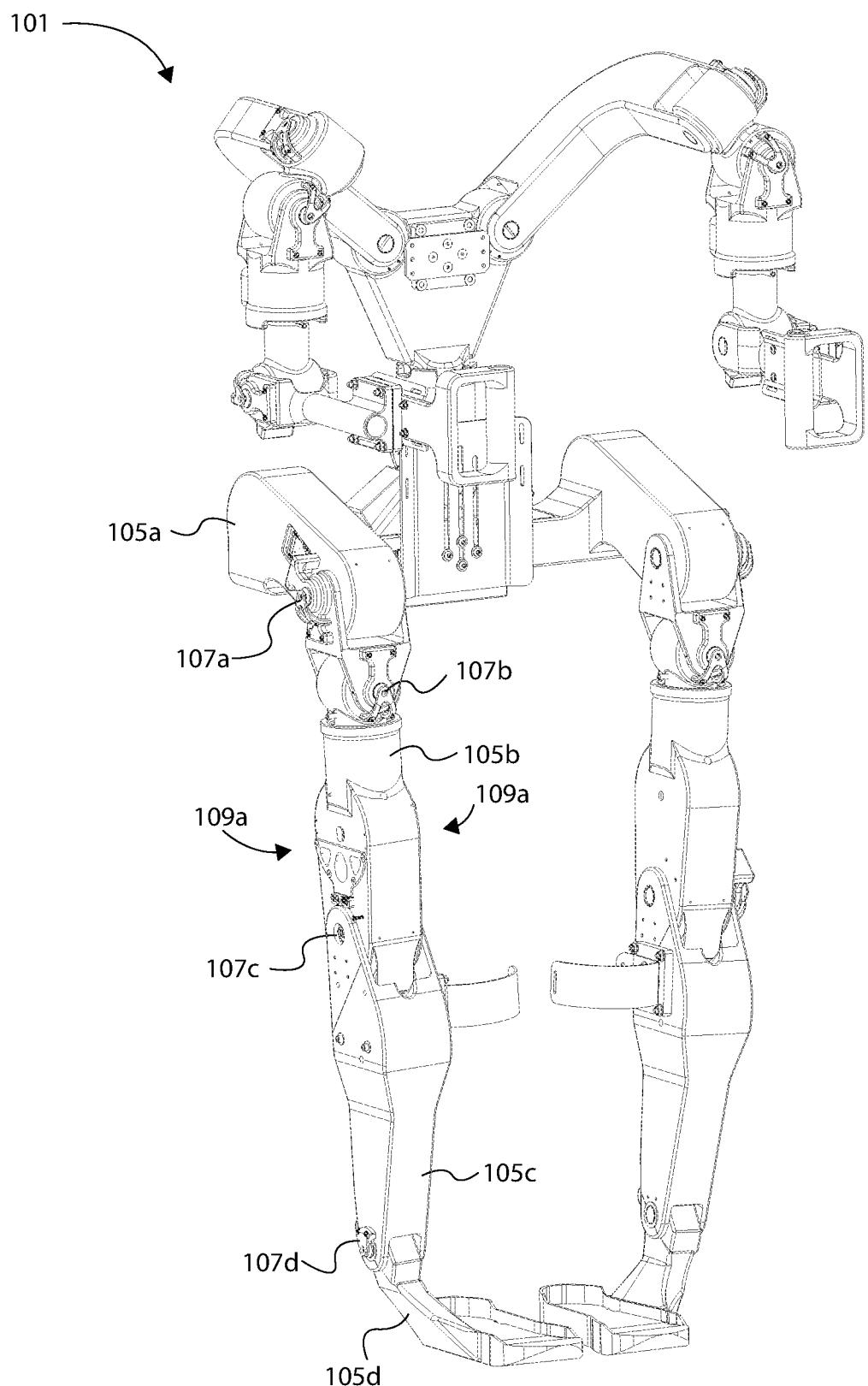
FIG. 4B is an isometric view of the robotic assembly of FIG. 4A.

FIGS. 4A and 4B show isometric views of an exemplary robotic assembly 101 in the form of an exoskeleton wearable or usable by a human operator. The robotic assembly 101 could alternatively be a humanoid robot, or other robotic assembly as discussed above. As shown, the robotic assembly 101 can be configured as a full-body exoskeleton (i.e., an exoskeleton having both a lower body portion and an upper body portion). However, this is not intended to be limiting as the exoskeleton can comprise only a lower body exoskeleton (i.e., some or all of the lower body portion), or only an upper body exoskeleton (i.e., some or all of the upper body portion).

The robotic assembly 101 can comprise left and right exoskeleton limbs. The right exoskeleton limb 103 can comprise a plurality of lower body support members 105a-d. The support members 105a-c can be coupled together for relative movement about a plurality of respective joints 107a-c defining a plurality of degrees of freedom about respective axes of rotation. The right knee joint 107c can comprise a tunable actuator joint module 109a having a quasi-passive elastic actuator, as described herein. It will be appreciated, although not detailed herein, that the hip joint 107a can also comprise a tunable actuator joint module having a quasi-passive elastic actuator, as described herein. The ankle joint 107d can also comprise a tunable actuator joint module, such as described below regarding FIGS. 20A-20F. The left exoskeleton limb can be similarly configured, as shown.

Figure 5A:
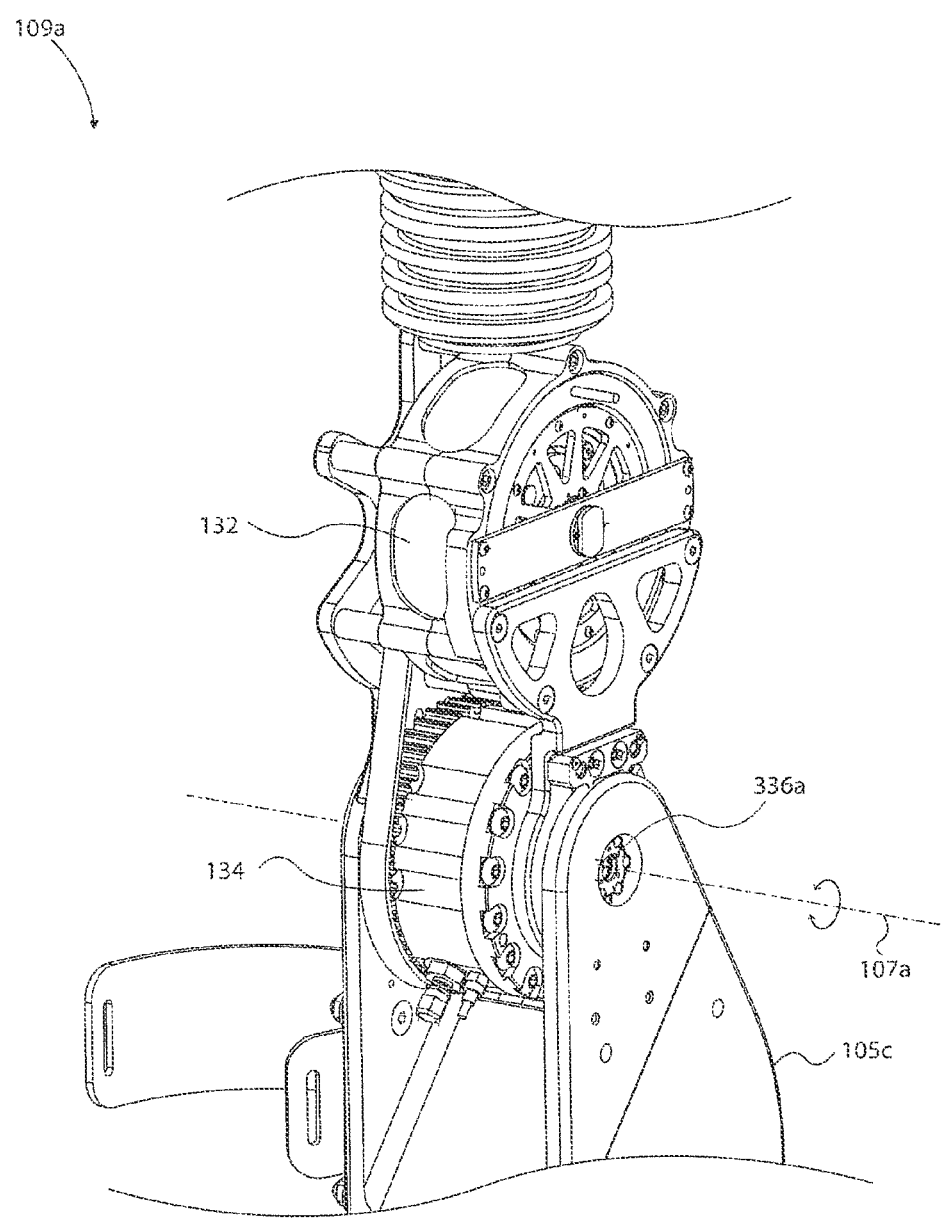
FIG. 5A is a partial isometric view a tunable actuator joint module for a knee joint of the robotic assembly of FIG. 4A in accordance with an example of the present disclosure.
Figure 5B:
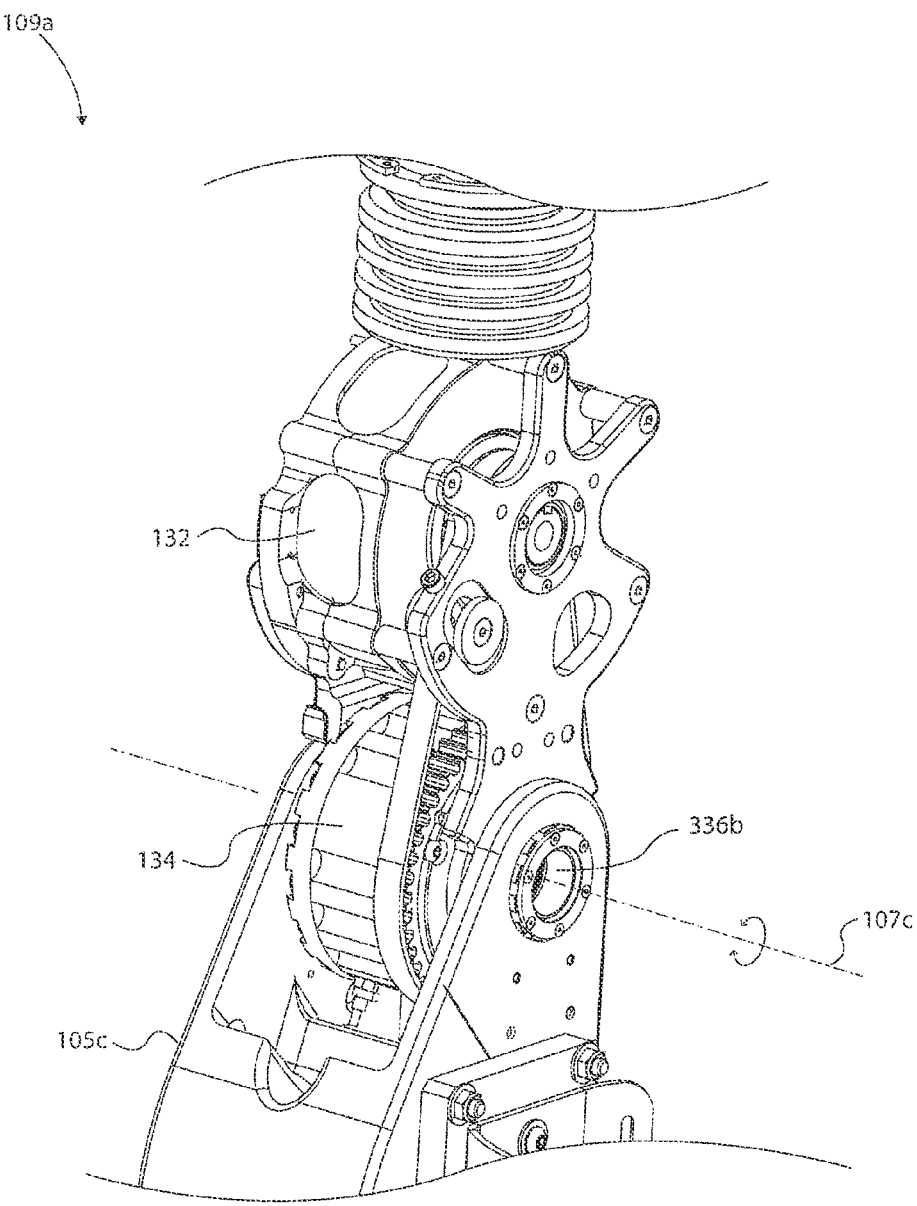
FIG. 5B is a partial isometric view of the tunable actuator joint module of FIG. 5A from another perspective.
Figure 6D:
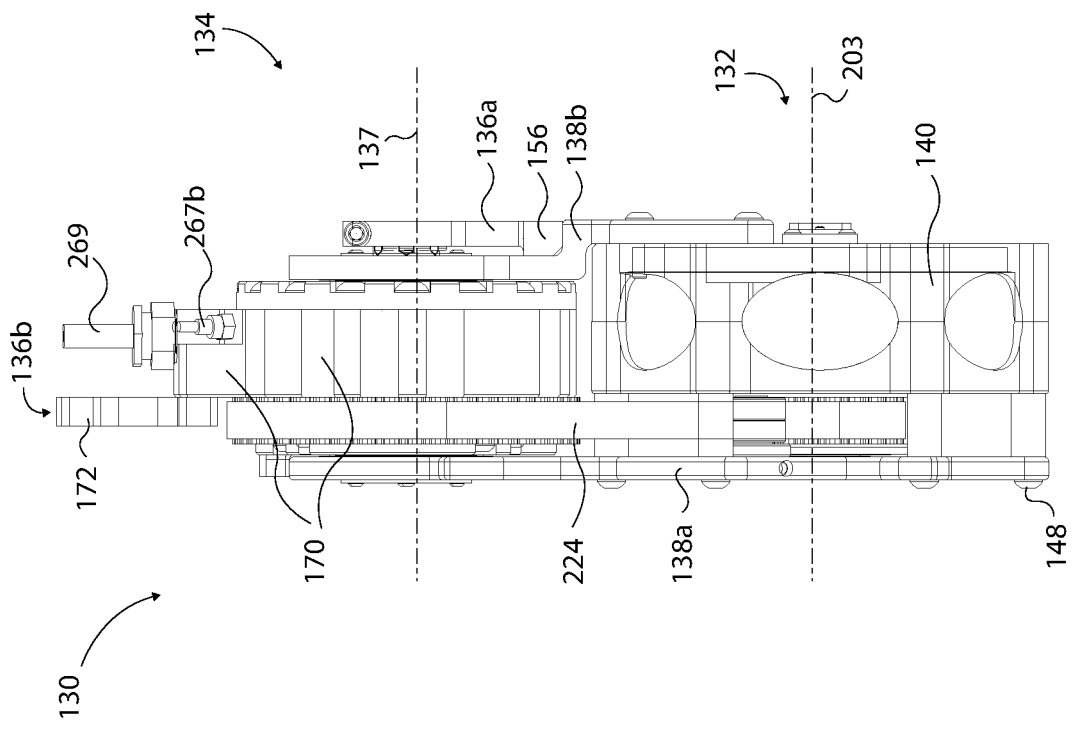
FIG. 6D is a left side view of the tunable actuator joint module of FIG. 6A.
Figure 6C:
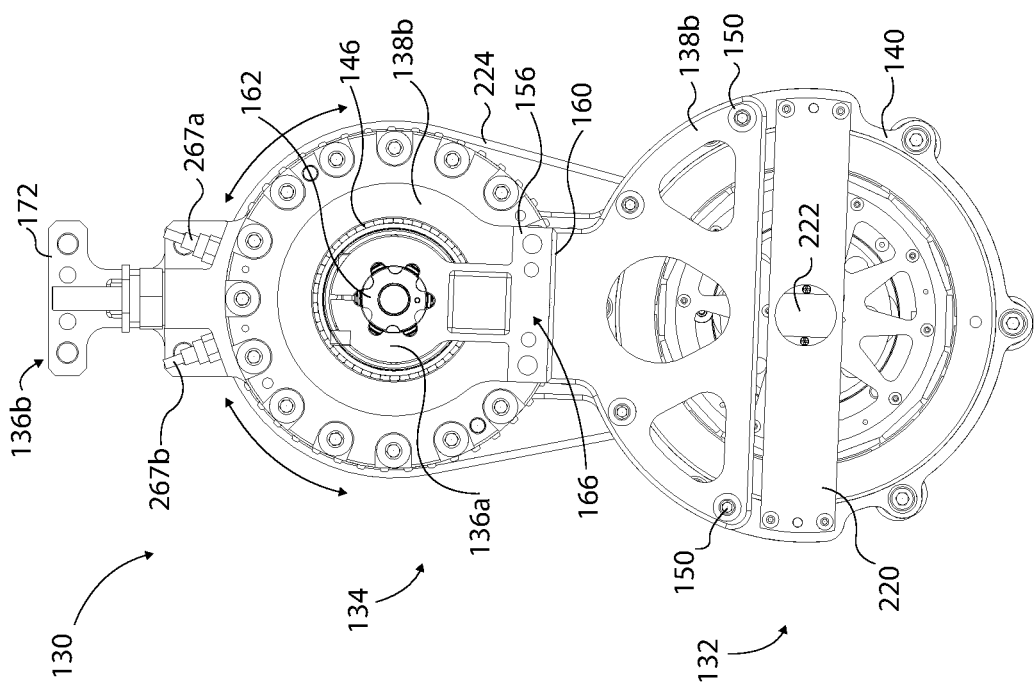
FIG. 6C is a front view of the tunable actuator joint module of FIG. 6A.

FIGS. 5A and 5B show close up, partial front and rear perspective views of the tunable actuator joint module 109a of FIG. 4A (with the support member 105b that supports the tunable actuator joint module 109a being hidden; but see FIGS. 4A and 4B, 12A and 12B). The particular tunable actuator joint module 109a of FIG. 5A will be specifically described regarding FIGS. 12A-12F.

The robotic assembly 101 of FIGS. 4A-5B can have the same or similar features as described generally with reference to FIG. 1. For example, the tunable actuator joint module 109a, which defines a degree of freedom corresponding to extension/flexion of a knee joint, can be configured to recover energy during a first gait movement and then release such energy during a second gait movement to apply an augmented torque to rotate the knee joint about the degree of freedom in parallel with a torque applied by a primary actuator of the tunable actuator joint module 109a, similarly as discussed above. Moreover, the tunable actuator joint module 109a can be selectively controlled to be disengaged from operation (i.e., inelastic by neither storing nor releasing energy) via a control system (e.g., a valve assembly), such that the joint "freely swings" with negligible resistance to rotate the joint as the operator walks or runs, for instance. And similarly, the tunable actuator joint module 109a can be "tuned" to define a predefined joint stiffness value, as further discussed below.

FIGS. 6A-11B illustrate various aspects of a tunable actuator joint module 130 according to an example of the present disclosure, which can be incorporated into a robotic assembly or system to comprise and define a joint as discussed herein. Although the tunable actuator joint module 130 in the present disclosure will be specifically focused as providing hip and/or knee joints of a robotic assembly this is not intended to be limiting in any way as those skilled in the art will recognize that similar concepts can be incorporated into a tunable actuator joint module configured for use in a different joint of the robotic system. For instance, the tunable actuator joint module 130 can readily be incorporated as the module 109a of FIG. 4A, with slight modification of the output member, as discussed below. Note that the tunable actuator joint module 130 is shown inverted for purposes of illustration clarity, yet it would readily be incorporated in the orientation as exemplified by the tunable actuator joint module 109a of FIG. 5A.

The tunable actuator joint module 130 comprises a primary actuator 132 and a quasi-passive elastic actuator 134 structurally coupled to each other, and operable with one another to provide torque to the joint. An input member 136a and an output member 136b (of the quasi-passive elastic actuator 134) can each rotate about an axis of rotation 137 (e.g., corresponding to an axis of rotation and corresponding degree of freedom of a human joint, such as the knee or hip joint). As shown, both the input and output members 136a and 136b can rotate about the same (collinear) axis of rotation 137; however, this is not meant to be limiting because the input and output members 136a and 136b could have different axes of rotation if positioned along different axes of rotation and operably coupled together. The primary actuator 132 (e.g., a geared electric motor) is operable to apply a torque to the output member 136b for rotation about the axis of rotation 137, and the quasi-passive elastic actuator 134 (e.g., a rotary pneumatic actuator) is selectively operable to generate a braking force, or to apply an augmented torque to the output member 136b along with the torque applied by the primary actuator 132 to actuate the joint, such as during a certain portion of a gait movement.

More specifically, the quasi-passive elastic actuator 134 is operable or controllable by a control system (e.g., a valve assembly) to selectively store energy or to selectively generate a braking force (in an elastic state or a semi-elastic state) upon a first rotation of the input member 136a, and to selectively release that energy (while still in the elastic or semi-elastic state) during a second or subsequent rotation of the input member 136a. In the elastic and semi-elastic states, the quasi-passive elastic actuator 134 can be enabled to generate a braking force to resist rotation of the joint, or to apply an augmented torque to the output member in parallel with the torque applied by the primary actuator 132 (as further detailed below), or both. Those skilled in the art will recognize that these different states of operation of the quasi-passive elastic actuator can entered into during rotation of the input member, and the joint, that is in the same or a different direction.

With respect to the elastic state of the quasi-passive actuator as it operates to store and release energy, in one aspect, the first rotation of the input member 136a can be achieved via active actuation of the primary actuator to actuate the tunable joint module and to cause rotation of the joint module (and any structural supports coupled thereto). In another aspect, the first rotation of the input member 136a can be achieved passively, namely by exploiting any available gravitational forces or external forces acting on the robotic system suitable to effectuate rotation of the input member 136b within the tunable actuator joint module (e.g., such as a lower exoskeleton being caused to perform a sitting or crouching motion, which therefore affects rotation of the various tunable joint modules in the exoskeleton). The exploiting of such gravitational forces by the quasi-passive actuator in parallel with a primary actuator provides the tunable joint module with compliant gravity compensation. Once the energy is stored, it can be released in the form of an augmented torque to the output member 136b, or it can be used to brake or restrict further rotation.

The quasi-passive elastic actuator 134 can further be configured, upon a third or subsequent rotation(s), to neither store nor release energy, the quasi-passive elastic actuator 134 being caused to enter an inelastic state. In this inelastic state, the input and output members 136a and 136b are caused to enter a "free swing" mode relative to each other, meaning that negligible resistance exists about the quasi-passive elastic actuator 134 (this is so that the actuator 134 does not exhibit a joint stiffness value that would restrict rotation of the input member 136a relative to the output member 136b, such as would be desired during a leg swing phase of a gait cycle of the robotic device). In this manner, the quasi-passive elastic actuator 134 is switchable between the elastic state and the inelastic state, such that the quasi-passive elastic actuator 134 applies an augmented toque (in the elastic state) in parallel with a torque applied by the primary actuator 134. This combined torque functions to rotate the output member 136b relative to the input member 136a in a more efficient manner as less torque is required by the primary actuator to perform the specific gait phase, thereby reducing the power requirements/demands of the primary actuator 134, as further detailed below.

In one example, the quasi-passive elastic actuator 134 can be structurally mounted to the primary actuator 132 by a first mounting plate 138a and a second mounting plate 138b, each positioned on either side so as to constrain the primary and secondary actuators 132 and 134 in a "sandwich" state (see FIGS. 7A-8B). The first mounting plate 138a is mounted to a housing mount 140 of the primary actuator 132 via a plurality of fasteners 142 (with spacers there between). The first mounting plate 138a comprises a primary aperture 144a (FIG. 8B) that rotatably supports a collar bearing 146 of the primary actuator 132, and comprises a secondary aperture 144b that rotatably receives a collar bearing 148 (FIG. 8B) supported by the quasi-passive elastic actuator 134.

The second mounting plate 138b is mounted to the other side of the housing mount 140 via a plurality of fasteners 151, and comprises an input aperture 152 that rotatably supports a collar bearing 154 (FIG. 8A) coupled to the quasi-passive elastic actuator 134. Therefore, collectively the input aperture 152 of the second mounting plate 138b and the secondary aperture 144b of the first mounting plate 138a are sized to structurally support the quasi-passive elastic actuator 134 and to facilitate rotation of the quasi-passive elastic actuator 134 via the collar bearings 148 and 154 supporting either side of the quasi-passive elastic actuator 134.

Figure 7A:
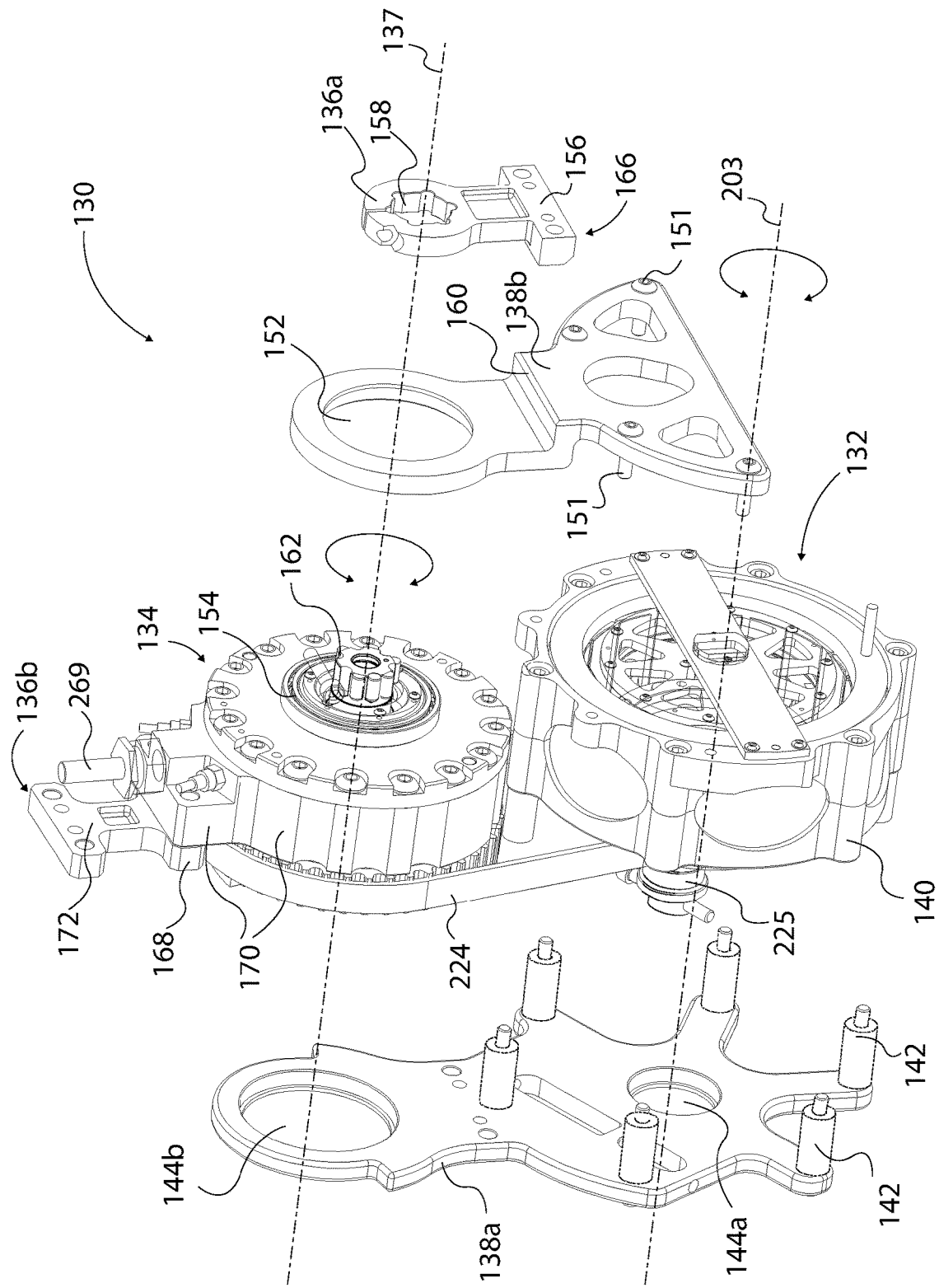
FIG. 7A is a partially exploded view of the tunable actuator joint module of FIG. 6A.
Figure 7B:
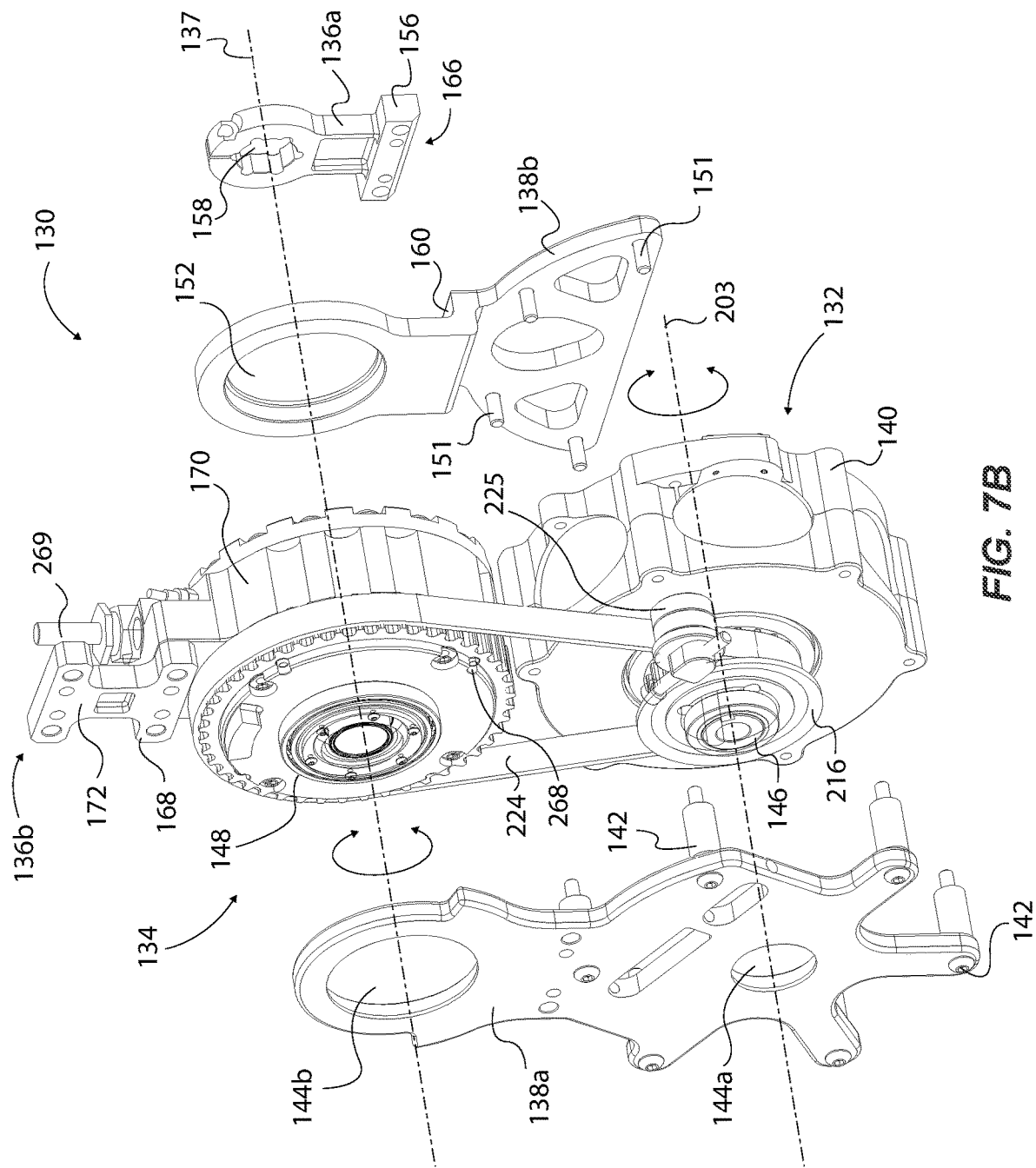
FIG. 7B is a partially exploded rear view of the tunable actuator joint module of FIG. 6A.
Figure 8A:
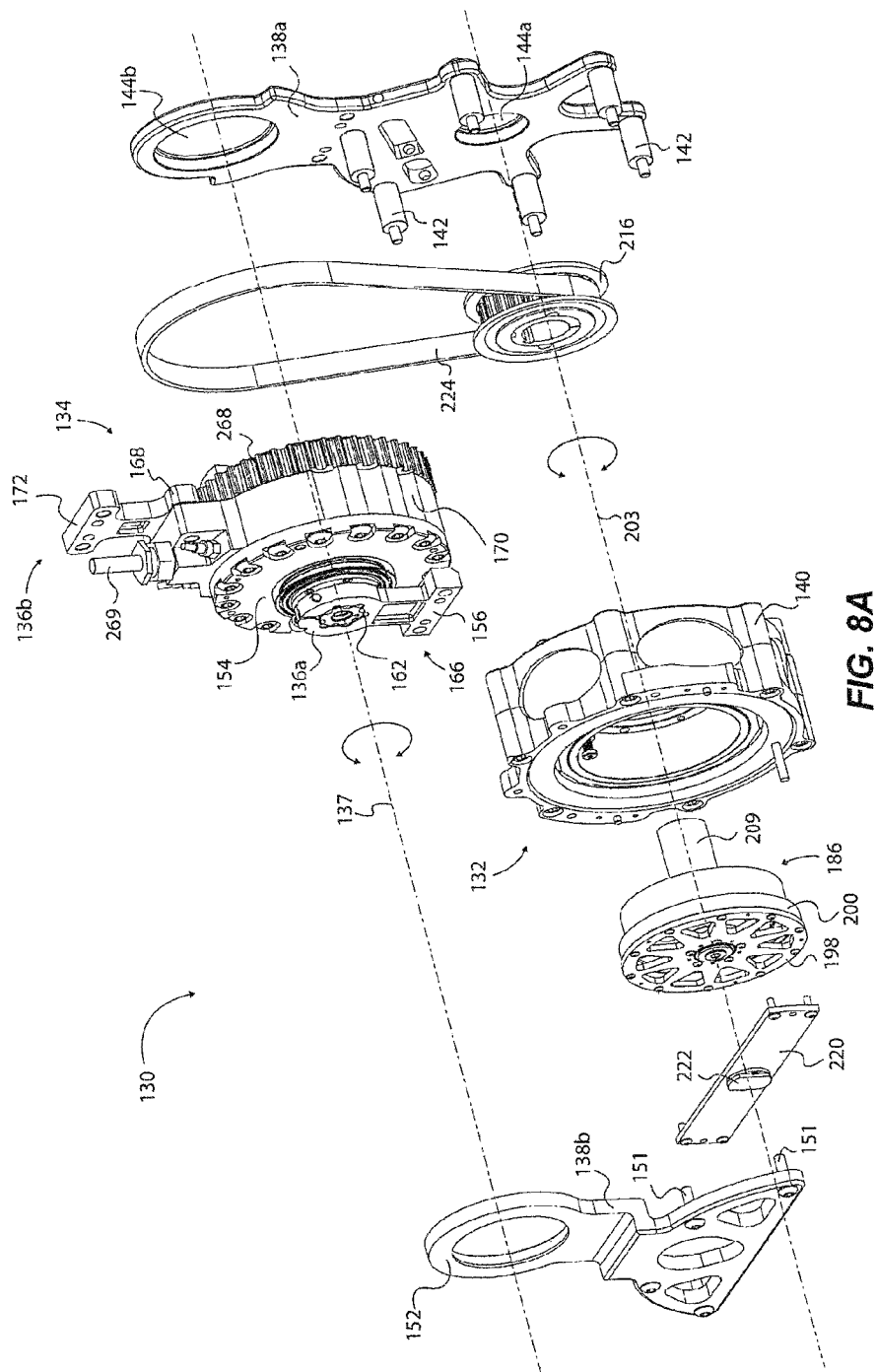
FIG. 8A is a partially exploded view of the tunable actuator joint module of FIG. 6A.
Figure 8B:
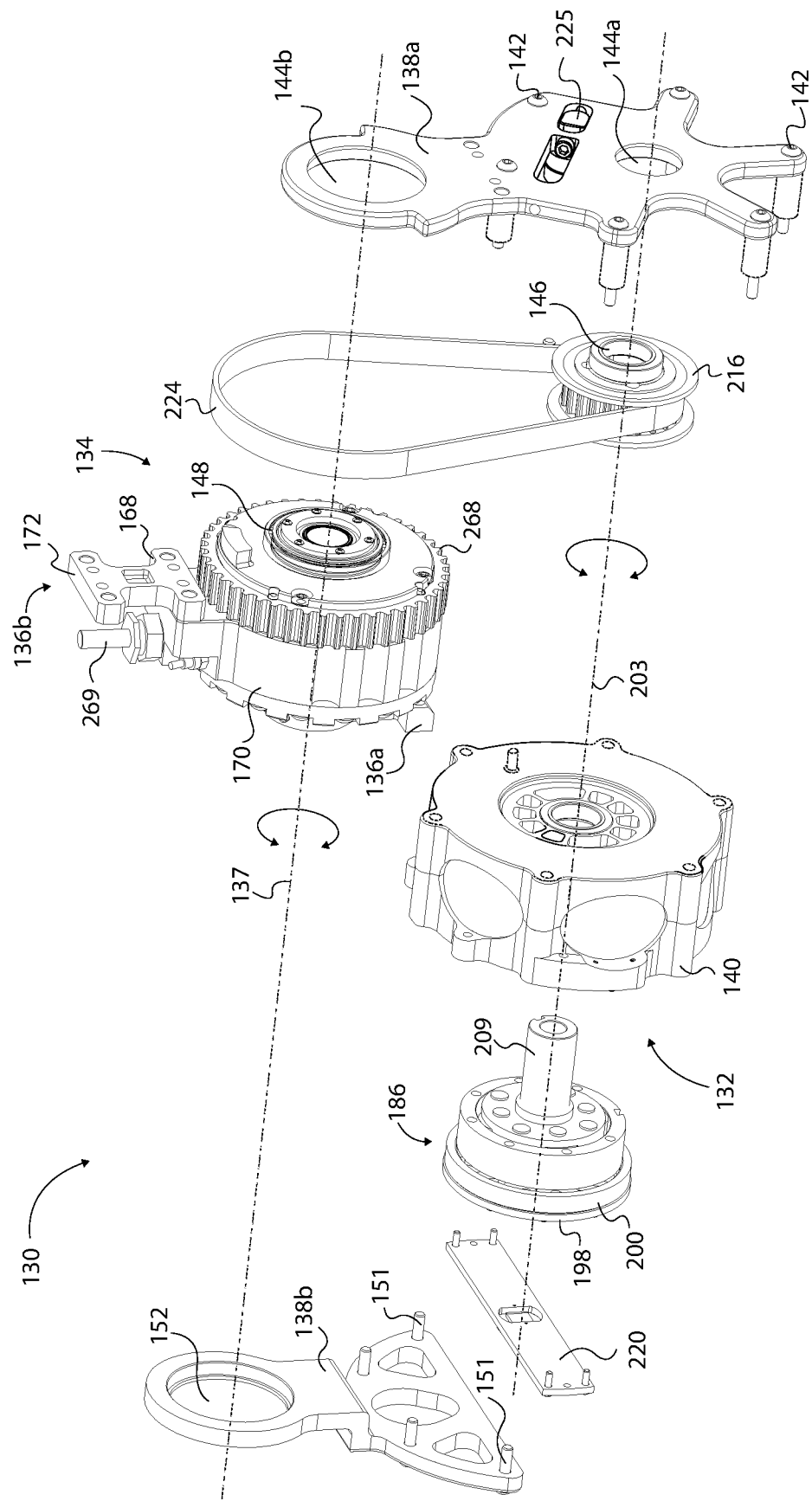
FIG. 8B is a partially exploded front view of the tunable actuator joint module of FIG. 6A.

The input member 136a can be a load transfer component that can comprise many different shapes and forms, depending upon the particular application (e.g., exoskeleton, humanoid robot, robotic hand or arm), and depending on the support member attached to the input member 136a (e.g., such as support member 105b of FIG. 4A). As such, the specific configurations shown are not intended to be limiting in any way. In the present example, the input member 136a can comprise a horizontal flange 156 and a rotary interface aperture 158 (FIGS. 7A and 8A). The horizontal flange 156 can be received and seated against a horizontal step portion 160 of the second mounting plate 138b to restrict movement of the input member 136a relative to the second mounting plate 138b, and thereby relative to the housing mount 140 of the primary actuator 134. The rotary interface aperture 158 can be coupled to an input interface member 162 of a first vane device 164 (see FIGS. 10A and 10B) that extends through the input aperture 152 of the second mounting plate 138b. The input member 136a can comprise a robotic support member interface portion 166 coupleable to a support structure of a robotic assembly, such as the support member 105b of FIG. 4A.

The output member 136b can be a load transfer component that can comprise many different shapes and forms, depending upon the particular application (e.g., exoskeleton, humanoid robot, robotic hand or arm). As such, the specific configurations shown are not intended to be limiting in any way. In the present example, the output member 136b can comprise an actuator interface portion 168 secured to a housing 170 of the quasi-passive elastic actuator 134 via fasteners (not shown). Alternatively, the output member 136b can be formed as an integral part of the housing, and be disposed closer to the axis of rotation 137, such as described below regarding FIGS. 12A-12E, and shown in the example exoskeleton of FIGS. 4A-5B.

The output member 136b can comprise a robotic support member interface portion 172 coupleable to a support structure of a robotic assembly, such as the exoskeleton of FIG. 4A. Therefore, as the quasi-passive elastic actuator 134 rotates about the axis of rotation 137, the output member 136b (and its associated support member) concurrently rotates with the attached housing 170 about the same axis of rotation 137.

With regards to the primary actuator 132 (see particularly FIGS. 9A and 9B with the primary actuator 132 shown in an exploded view), can comprise a housing mount 140. The housing mount 140 comprises a first mount structure 174a and a second mount structure 174b coupled to each other via fasteners 176. The first and second mount structures 174a and 174b are fastened together to house and structurally support many of the components of the primary actuator 132. For instance, the primary actuator 132 comprises a motor 178 that is seated in respective annular recesses of the first and second mount structures 174a and 174b. The motor 178 can be a high-performance Permanent Magnet Brushless DC motor (PM-BLDC), which can be a variant of a frameless torque motor with winding optimized to achieve the desired maximum torque and speed while operating using a 48 VDC supply and a high-performance COTS controller, such as motor MF0127-032 marketed by Allied Motion. Controlling a brushless electric motor is well known and will not be discussed in detail, but it will be appreciated that any number of control schemes can be used in combination with the motor and sensors associated with the tunable actuator joint module 130 to operate the motor. The motor described above and shown in the drawings is not intended to be limiting in any way. Indeed, other motors suitable for use within the primary actuator 132 are contemplated herein, as are various other types of actuators, such as hydraulic actuators.

The motor 178 can comprise a stator 180 and rotor 182 rotatable relative to each other (in a typical fashion for commercially available frameless brushless motors). The motor 178 can be configured to comprise a central void 184 about the central area of the motor 178 and surrounded by the rotor 182. Advantageously, a transmission, such as the planetary transmission 186, can be positioned within (entirely or partially) the central void 184. This provides a low-profile geared motor state with high torque output for a relatively small electric motor, as exemplified below. It should be appreciated that the planetary transmissions exemplified herein can be replaced (or supplemented with) other transmission types, such as harmonic, cycloidal, worm, belt/chain, crank, four-bar linkage, backhoe linkage, bell crank, continuously variable, or any others as will be recognized by those skilled in the art. These other types of transmissions are not detailed herein as those skilled in the art will recognize how these may be implemented without undue experimentation.

Planetary transmissions are well known and will not be discussed in great detail. However, in the present example the planetary transmission 186 can be configured as a 4:1 geared planetary transmission. Thus, in one example the planetary transmission 186 can comprise an outer ring 190 engaged to four planet gears 188 (one labeled) mounted about a carrier 192, whereby the four planet gears 188 have gear teeth that engage with the gear teeth of a central sun gear 194 (FIG. 9B). With planetary transmissions generally, the stationary component can be any one of the outer ring 190, or the carrier 192, or the sun gear 194, for instance, whereby the other two components are rotatable relative to the chosen stationary component.

In the present example, the outer ring 190 is stationary, as it is fastened to the first mount structure 174a via fasteners (not shown) through apertures 196 around the outer ring 190 and into threaded bores 197 in the first mount structure 174a. A rotatable transfer wheel 198 (FIG. 9A) is disposed on an outer side of the primary actuator 132 adjacent the second mount structure 174b, and is fastened to a drive collar 200 via perimeter fasteners 202. The drive collar 200 is fastened or fixed to the rotor 182 of the motor 178. The transfer wheel 198 is operable to transfer rotation from the rotor 182 of the motor 178 to the sun gear 194 about the axis of rotation 203 (FIG. 8A). A spacer sleeve 201 can be positioned adjacent the drive collar 200 and between the outer ring 190 of the planetary transmission 186 and the rotor 182 to act as a support spacer between the planetary transmission 186 and the rotor 182.

The transfer wheel 198 can comprise a central aperture 204 that supports a transfer hub 206 that is fastened to the transfer wheel 198 via fasteners 208. The transfer hub 206 can have inner gear teeth (not shown) that can be engaged with outer gear teeth of the sun gear 194. Therefore, upon applying an electric field to the motor 178, the rotor 182 rotates about axis 203, which causes the transfer wheel 198 to rotate, which thereby causes the sun gear 194 to rotate, all in a 1:1 ratio. Upon rotation of the sun gear 194 about axis of rotation 203, the planetary gears 188 rotate around the sun gear 194, which causes the carrier 192 to rotate. An output shaft 209 is secured to a central portion 211 of the carrier 192, such that rotation of the carrier 192 causes rotation of the output shaft 209 about axis 203, which provides a 4:1 geared-down transmission arrangement from rotation of the rotor 182 to the output shaft 209 via the planetary transmission 186. Other planetary transmission types and gear reduction schemes can be used instead of a 4:1 transmission, such as a 3:1 or a 2:1 (or even greater ratios) planetary gear scheme.

To reduce build height, the planetary transmission 186 can be positioned inside of the rotor 182 of the motor 178. Depending on the motor selected, the inside diameter of the rotor will dictate the maximum outside diameter of the planetary transmission. Once the planetary ring has been constrained by its outside diameter, there are a limited amount of options for gear ratios and output torques available. The output ratio is determined from the ratio of the number of teeth on the ring gear to the number of teeth on the sun gear. To obtain a higher reduction in the compact design of the planetary unit, the sun gear diameter can be reduced, which generally corresponds to less power transmission. The capacity to transmit higher torques is reduced with a smaller sun gear. A balance of reduction and strength can be determined for a planetary unit that will physically fit inside the motor rotor. By implementing a helical cut gear, higher forces can be transmitted on the gear teeth making the unit stronger. A wider tooth will also improve the load carrying capacity of the sun gear, however this increases the weight as well.

In addition, the sun gear 194 makes contact with several teeth simultaneously so the contact ratio is much higher than a conventional spur gear transmission. Another benefit of planetary gears is the fact that the transmission is in-line with the motor, which allows for compact mounting states. Two of the 4:1 planetary units (one shown on FIG. 9B) can be nested together to produce a 16:1 final drive, for instance.

Thus, in one example using Allied Motion's MF0127-032 motor, it has an inside diameter of 3.3 inches, which means that a planetary transmission of approximately 3.15 inches (or less) could be used and disposed in the central void of the motor. And, Matex's 75-4MLG12 planetary transmission can be incorporated, which is a 4:1 unit with a 2.95 inch outside diameter having a 118 N-m peak torque, weighing just 500 grams. Such planetary transmission could be incorporated with a brushless motor as discussed herein to generate a compact configuration. Therefore, in the illustrated example of FIG. 9B, the output shaft 209 applies a relatively higher torque at a low speed with very little noise and backlash via the planetary transmission 186, all in a compact form because the planetary transmission 186 is housed within the void 184 of the brushless frameless electric motor 178, for instance. It is noted that the specific types of motors and planetary transmissions described herein are not intended to be limiting in any way, as will be recognized by those skilled in the art.

Figure 9A:
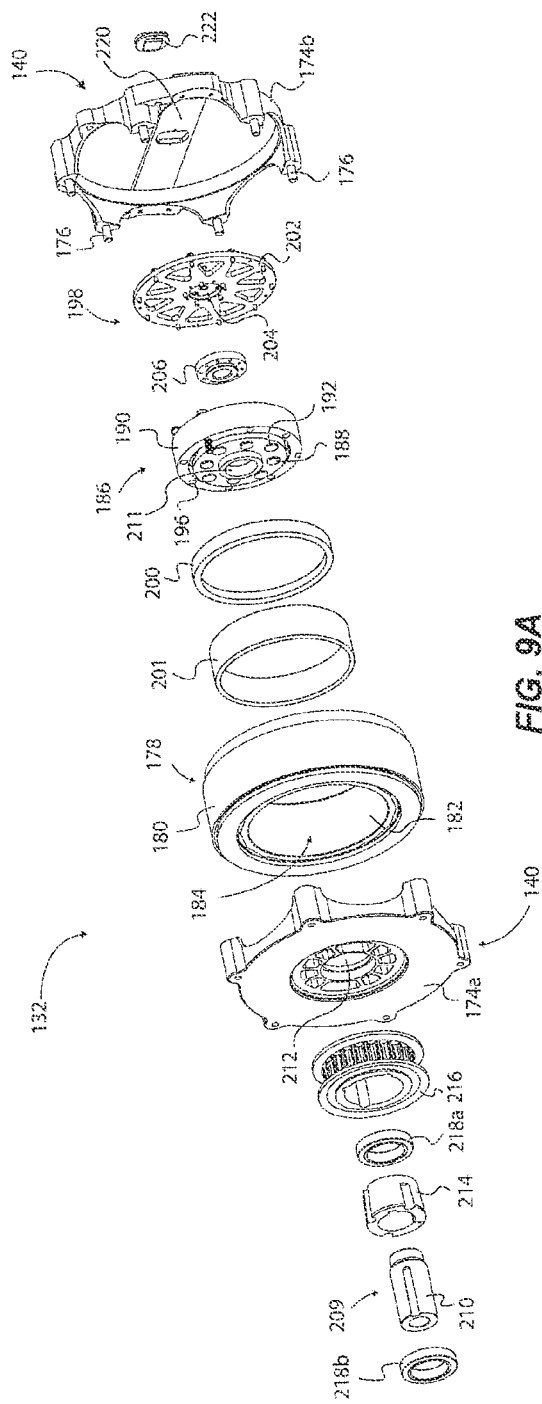
FIG. 9A is an exploded view of the primary actuator of the tunable actuator joint module of FIG. 6A.
Figure 9B:
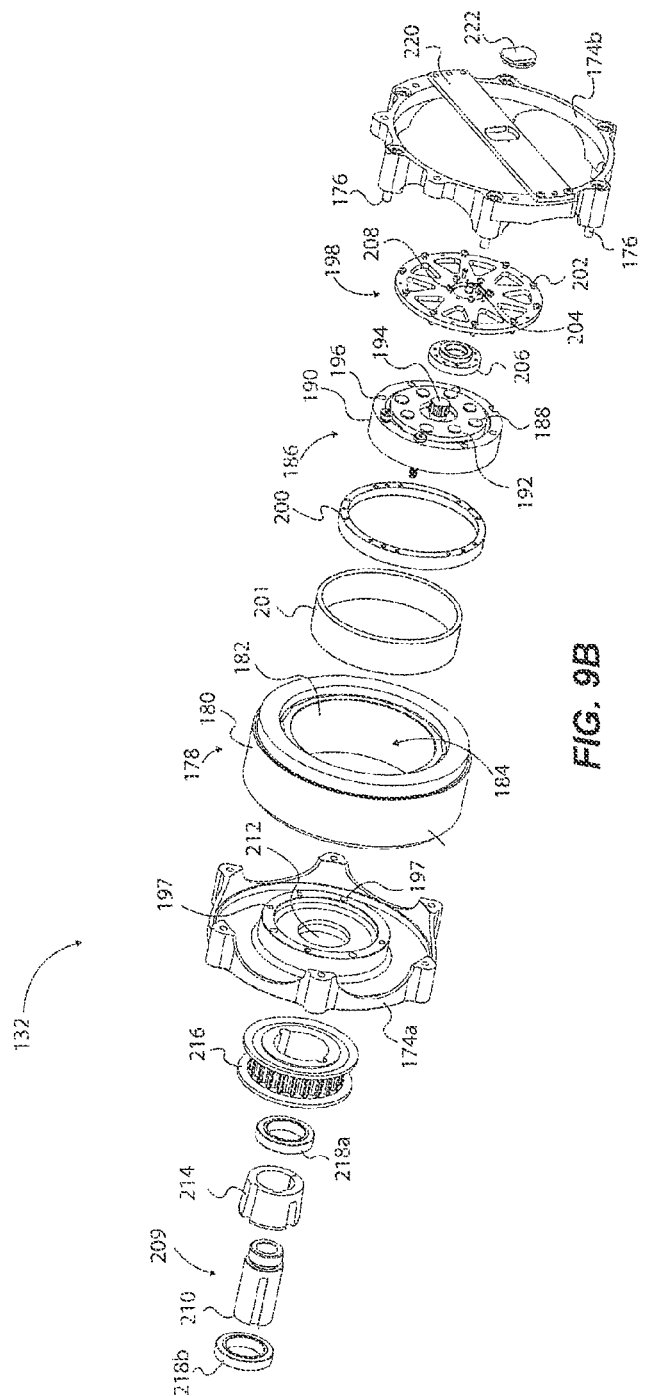
FIG. 9B is a partially exploded front view of the primary actuator of the tunable actuator joint module of FIG. 6A.

With continued reference to FIGS. 9A and 9B, a free end 210 of the output shaft 192 extends through an aperture 212 of the first mount structure 174a. A tapered support collar 214 surrounds and is coupled to the output shaft 192 (a key and slot interface can be used to couple the support collar 214 to the output shaft 192). The tapered support collar 214 has an outer tapered surface that mates to an inner tapered surface of a primary pulley 216 (e.g., such as a Morse taper interface) to couple the output shaft 192 to the primary pulley 216 (a key and slot interface can be used to couple the support collar 214 to the primary pulley 216). A first collar bearing 218a is positioned within the aperture 212 (FIG. 9A) of the first mount structure 174a to rotatably support the output shaft 192, and a second collar bearing 218b is positioned with an outer end of the primary pulley 216 to rotatably support the free end 210 of the output shaft 192.

In one example, a sensor plate 220 can be fastened to an outer side of the second mount structure 174b, and has an aperture that supports a position sensor 222. The position sensor 222 is adjacent the transfer wheel 198, which has an aperture through to the sun gear 194 to allow the position sensor 222 to determine the position of the sun gear 194, which can ultimately determine the rotational position of the output shaft 209, thereby providing the angular position of a knee or hip joint, for instance. The position sensor 222 can be any suitable sensor, such as a 13-bit hall-effect sensor. Additional positions sensors can be coupled to the system, and utilized to ultimately determine the position of the joint. As discussed above regarding the graphs of FIGS. 3B and 3C (and below regarding the valve assembly), the particular position of the knee joint is relevant in determining and controlling actuation of a valve assembly to switch the tunable actuator joint module between the inelastic and elastic or semi-elastic states (e.g., engage and disengage the elastic actuator), or to dynamically vary a zero point or position of the elastic actuator, as further discussed below.

Referring back to FIGS. 6A-8B, upon rotation of the output shaft 209 (in either rotational direction) by operating the motor 178, the primary pulley 216 rotates a transmission belt 224 that is coupled to the quasi-passive joint actuator 134 (as further discussed below) to provide a primary torque to rotate the tunable actuator joint module 130 to rotate the knee joint, for instance. The transmission belt 224 can be a Gates Poly Chain GT Carbon synchronous belt, or other suitable belt. A belt tensioning device 225 (FIGS. 7B and 8B) can be adjustably slidably coupled to a slot of the first mounting plate 138a via a fastener, which is operable by a user with a tool to slide the belt tensioning device 225 toward or away from the belt 224 to tighten or loosen the belt 224, as desired. In some examples, various other torque-transmitting devices can replace the particular configuration of the belt 224, such as one or more belts or linkages or gears or tendons or others (or combinations of such), and such alternatives can be arranged to have an axis of rotation that is offset (e.g., oriented in a direction along a plane that is perpendicular or orthogonal or some other angle) to the axis of rotation 203 of the primary actuator 132 (or some other angle other than parallel). And, various transmissions can be arranged to provide different gear reductions from input to output, including a relatively high gear reduction (e.g., 20:1, or more), or a relatively low gear reduction (e.g., 1:1), or any gear reduction between these, depending on the particular application. In some examples, the torque-transmitting device in the form of belt 224, or such various alternative torque-transmitting devices, can allow the primary actuator 132 to be remotely located away from the output (i.e., the primary actuator 132 is located a given distance away from the output of the tunable actuator joint module, but operably connected thereto via the torque-transmitting device), wherein the remotely located primary actuator 132 can be actuated and its torque transferred to the output of the tunable actuatable joint module corresponding to a joint of the robotic system. For instance, the primary actuator 132 could be located at a lower back area of an exoskeleton (e.g., FIG. 4A), while such alternative torque-transmitting device(s) could transfer the primary toque from the lower back area to an output member located in the tunable actuator joint module for the hip joint for actuating the hip joint.

With regards to the quasi-passive elastic actuator 134 (particularly with reference to FIGS. 10A and 11B), the quasi-passive elastic actuator 134 is operable to apply an augmented or supplemental torque (e.g., to the output member 136b, which can be fixed to a support member, such as a robotic support member). The input member 136a and the output member 136b can each be rotatable about the axis of rotation 137 (or rotatable about different axes). Notably, the axis of rotation 137 is substantially parallel to the axis of rotation 203 of the primary actuator 132 (see FIG. 7A). This contributes to the compact nature of the tunable actuator joint module 130 because the primary actuator 132 and the quasi-passive elastic actuator 134 are vertically positioned, or stacked, relative to one another (e.g., see FIGS. 6A-6D), which locates substantially all of the mass of the tunable actuator joint module 130 proximate or near the axis of rotation 137 of the joint (i.e., about the input and output members 136a and 136b).

In one example, the quasi-passive elastic actuator 134 can comprise a rotary pneumatic (e.g., or other) actuator having a rotary pneumatic spring as the elastic component that is selectively operable (e.g., engageable and disengageable at select times and for select durations) to apply an augmented torque to the output member 136b along with the torque applied by the primary actuator 132, or to generate and apply a braking force. The quasi-passive elastic actuator 134 can be made selectively operable via control of a valve assembly associated with the elastic actuator 134 (discussed further below). The quasi-passive elastic actuator 134 is operable to selectively store energy (elastic state) upon a first rotation of the input member 136a, and to selectively release energy (elastic state) upon a second rotation of the input member 136a to apply an augmented torque to the output member 136b in parallel with the torque applied to the output member 136b by the primary actuator 132, where the release of the energy and the augmented torque are caused to occur at phases, or portions of phases, of the gait cycle that exhibit an elastic response (see FIG. 3A). The quasi-passive elastic actuator 134 is further configured, upon a third rotation, to neither store nor release energy (inelastic state) about the quasi-passive elastic actuator 134. Likewise, a braking force can be generated during certain operating scenarios where it may be desirable to brake or restrict, to some degree, rotation of the joint. The braking force can be applied to restrict rotation when the primary actuator is inactive, but rotation of the input member and joint are still occurring (e.g., in response to an external force), but this is not intending to be limiting as the braking force can be applied at a time when the primary torque is being applied to the output member from the primary actuator.

The housing 170 of the quasi-passive elastic actuator 134 can comprise a housing body 226 and a faceplate 228 fastened together via a plurality of fasteners 230, and that collectively define a cavity 232 (FIG. 10B) of the housing 170. A first vane or vane device 164 and a second vane or vane device 229 are supported by the housing 170 and rotatable relative to each other about the cavity 232. The input interface member 162 of the first vane device 164 extends through a central aperture 234 of the faceplate 228 (and through the input aperture 152 of the second mounting plate 138b (see FIG. 7A)).

The input interface member 162 is rotatably supported about the faceplate 228 by a collar bearing 236. The collar bearing 236 is held in position by a ring 241 fastened to the faceplate 228. The input interface member 162 comprises key slots 238 disposed radially around the input interface member 162, and that receive keys/rods (not shown) that interface with corresponding key slots formed internally about a central aperture 240 of the input member 136a.

Opposite the input interface member 162 of the first vane device 164 is a cylindrical stabilizing portion 242 (FIG. 10A) that extends through a central aperture 244 of the chamber body 226, and is rotatably supported to the housing 170 by a collar bearing 246 that surrounds the annular stabilizing portion 242. The collar bearing 246 can be seated in an outer recess of the housing body 226. A ring 248 can be fastened to the housing body 226 to retain the collar bearing 246 about the housing body 226. The collar bearing 148 surrounds an outer annular member 250 of the housing body 226 and is rotatably interfaced with the secondary aperture 144b of the first mounting plate 138a (see FIG. 7B) to rotatably support the housing body 226 with the mounting plate 138a.

Figure 10A:
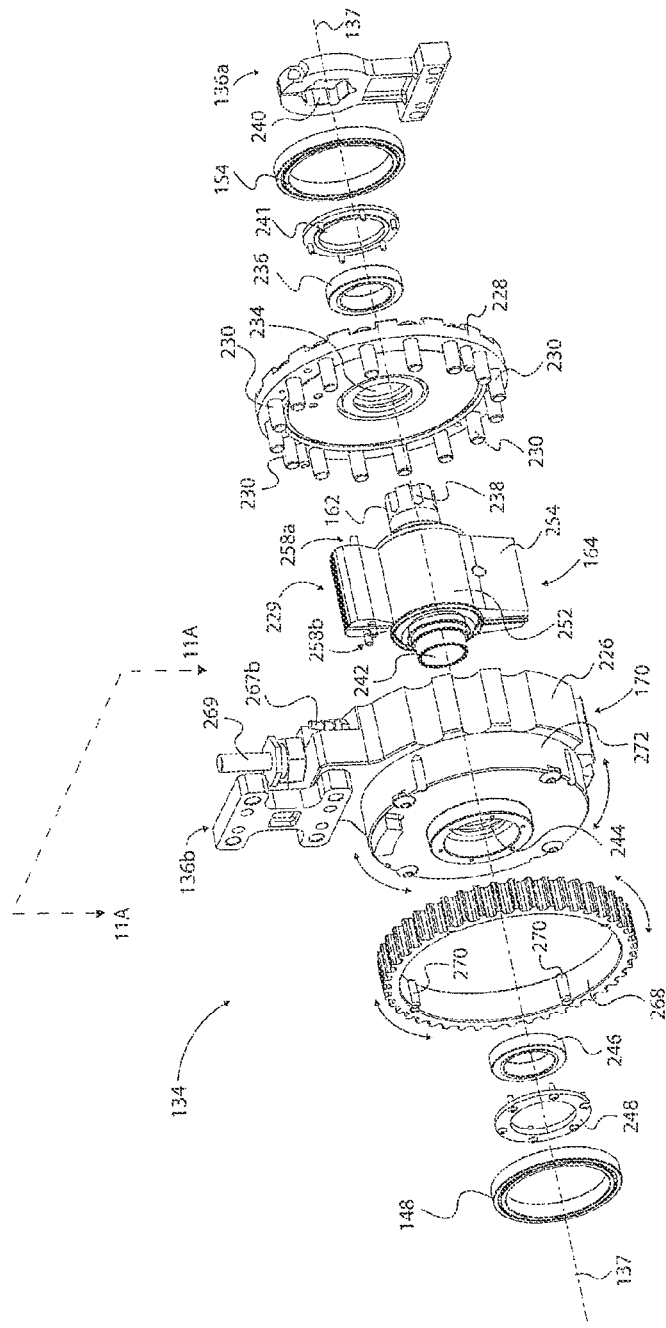
FIG. 10A is an exploded view of the quasi-passive elastic actuator of the tunable actuator joint module of FIG. 6A.
Figure 11A:
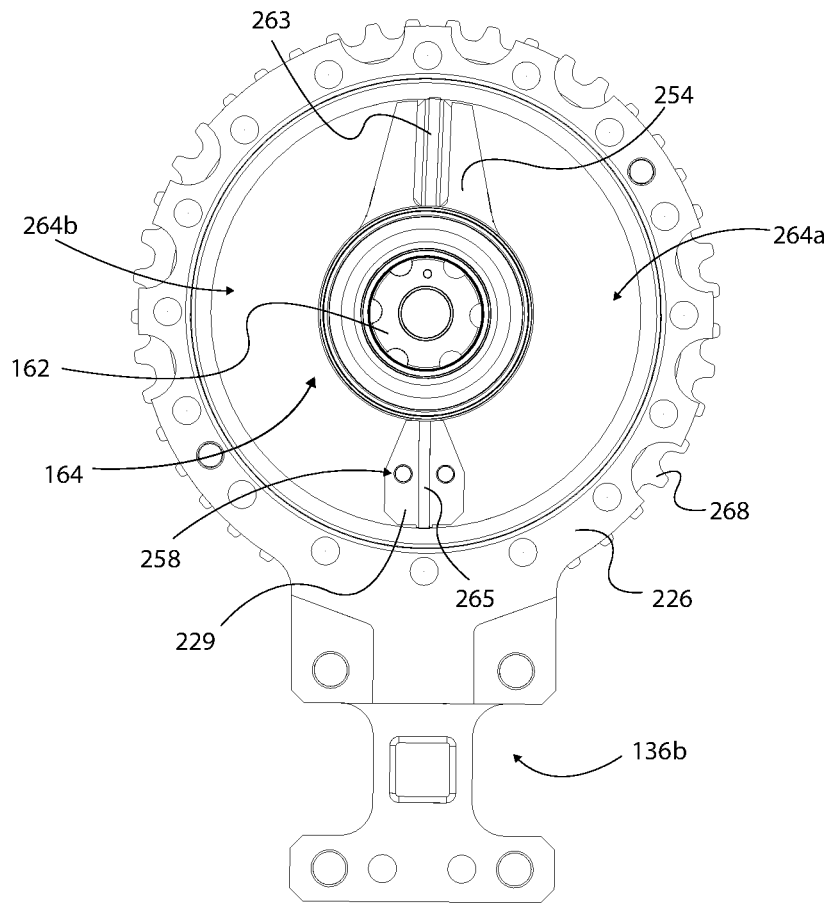
FIG. 11A is a cross-sectional view of the quasi-passive elastic actuator of the tunable actuator joint module of FIG. 6A taken along lines 11A in FIG. 10B.
Figure 14A:
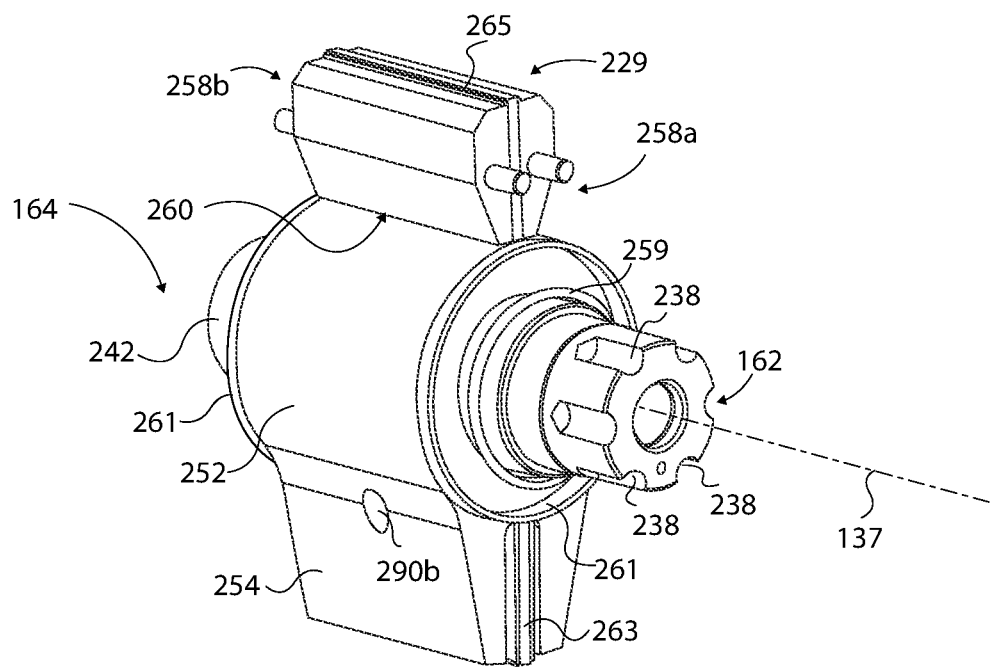
FIG. 14A is an isometric view of a first vane device and a second vane device of a quasi-passive elastic actuator of a tunable actuator joint module operable with the any one of the tunable actuator joint modules of FIGS. 5A, 6A, 12A, and 13A, in accordance with an example of the present disclosure.
Figure 14B:
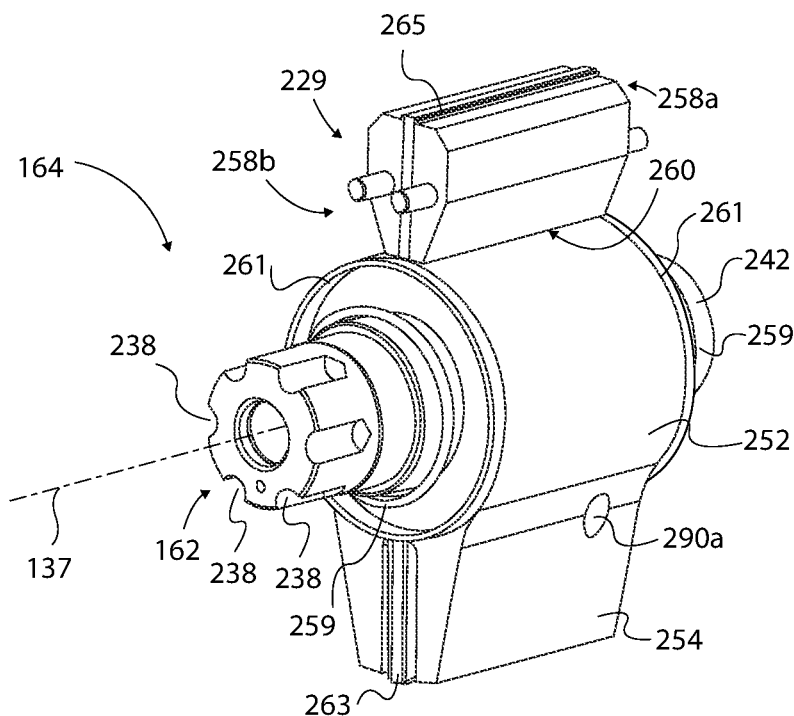
FIG. 14B is an isometric view of the first vane device and the second vane device of FIG. 14A from another perspective.

With continued reference to FIGS. 10A and 10B, and with reference to FIGS. 14A-14B, the first vane device 164 can be a unitary or uniform body that comprises a cylindrical body portion 252 and an elongated vane 254 extending from the cylindrical body portion 252. In one example, the second vane device 229 can comprise an elongated vane positioned such that it extends approximately 180 degrees from the elongated vane 254 of the first vane device 164 when in a nominal position (FIG. 11A). The second vane device 229 can be fixed to the housing body 226 and the faceplate 228 by a pair of pins 258 (FIG. 10B) that extend laterally through either end of the second vane device 229. The pair of pins 258 extend into receiving bores of the housing body 226 and the faceplate 228. Thus, the second vane device 229 is fixed to the housing 170, such that rotation of the housing 170 about the axis of rotation 137 causes concurrent rotation of the second vane device 229 relative to the first vane device 164 (see e.g., comparison and discussion of FIGS. 11A and 11B). In this manner, the second vane device 229 has an interface surface 260 that slidably engages the outer surface 262 of the cylindrical body portion 252 of the first vane device 164 (FIG. 14A).

Figure 11B:
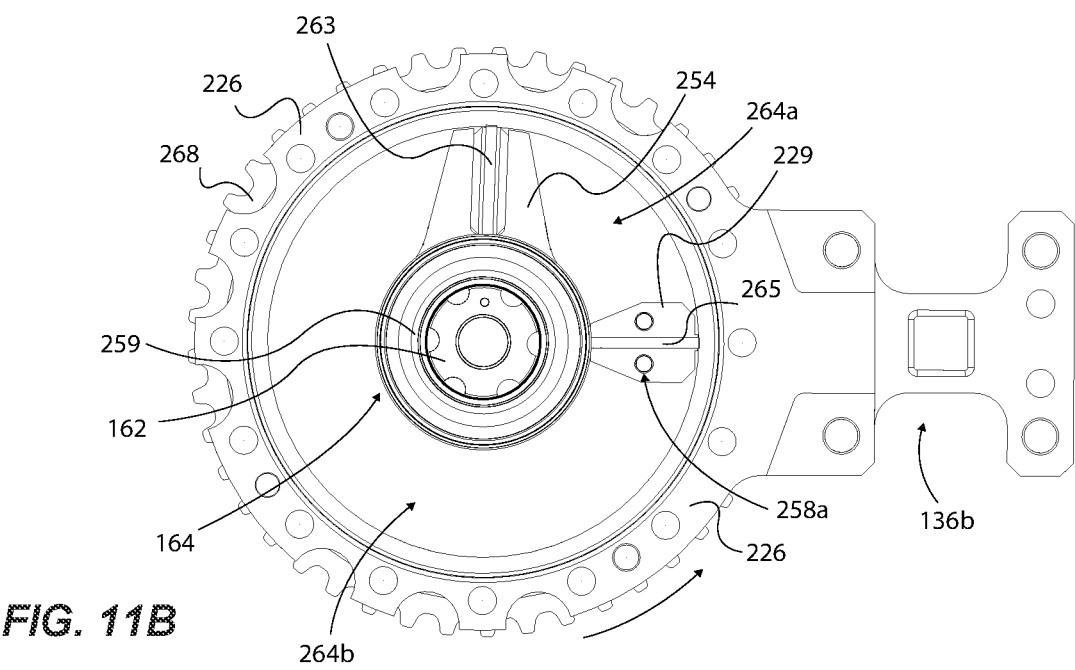
FIG. 11B is a cross-sectional view of the quasi-passive elastic actuator of the tunable actuator joint module of FIG. 6A taken along lines 11A in FIG. 10B, but shown in a rotated state.

As can be appreciated from FIGS. 11A and 11B, the first vane device 164 and the second vane device 229 define a compression chamber 264a and an expansion chamber 264b (as also defined by the boundaries of the cavity 232 of the housing 170). The location of the second vane device 229 relative to the first vane device 164 can define the volume of these chambers. In one example, the second vane device 229 can be located 180 degrees from a 0 degree position of the first vane device 164, wherein the compression and expansion chambers 264a and 264b, respectively, comprise the same volume, as shown on FIG. 11A. Note that the cross sectional view of FIG. 11A is inverted relative to the position shown on FIG. 10B. The second vane device 229 can be located relative to the first vane device 164 at other positions so as to provide or define compression and expansion chambers having disparate volumes, or in other words different volume ratios, when the quasi-passive elastic actuator is in the inelastic state or mode (that facilitating free-swing). Furthermore, the elastic component can be pre-charged prior to the first rotation, such that a pressure differential exists between the compression chamber and the expansion chamber.

The cavity 232 (i.e., the compression and expansion chambers 264a and 264b, respectively) of the housing 170 can be gas pressure charged to a nominal pressure (e.g., approximately 1500 psi) via a valve 269 (FIG. 10B), such that both chambers 264a and 264b have equalized gas pressure when the first vane device 164 is at its nominal position (the position of the rotor vane relative to the second vane device when the quasi-passive elastic actuator is in the inelastic mode just prior to entering the elastic mode) (e.g., 180 degrees relative to the second vane device 229, 90/270 degrees relative to the second vane device 229, and others)

(and when the valve assembly is open, as discussed below). A compression chamber valve 267a and an expansion chamber valve 267b (FIG. 10B) are each in fluid communication with respective compression and expansion chambers 264a and 264b to facilitate removing or adding an amount of gas pressure in each or both chambers as desired to generate a particular spring stiffness value. In some example, this spring stiffness value can be dynamically modified by the operator while in the field of use. For instance, a person or operator wearing an exoskeleton may desire a stiffer knee joint when performing a particular task or carrying a certain load. Accordingly, the nominal gas pressure in the cavity 232 can be dynamically tuned or modified in real-time and in the field by removing or adding gas pressure within the housing 170 via the valves, thus permitting a variable joint stiffness value within the quasi-passive elastic actuator. This is an advantage over systems that have a manufactured spring stiffness that is not modifiable by a user. In any event, the quasi-passive elastic actuator can be pre-charged with a pre-charge pressure to comprise a predetermined joint stiffness value. In some examples, "pre-charge" can refer to injecting or introducing pressurized gas (i.e., above ambient) into both the compression and expansion chambers 264a and 264 when the first and second vane devices are at their nominal positions (e.g., 180 degrees relative to each other, in the above example). Therefore, the higher the pre-charge pressure (e.g., 200 psi vs. 1646 psi), then the greater the spring stiffness value for a particular actuator joint module, because a greater gas pressure would result in a particular compression chamber when pre-charging with a higher gas pressure with the same amount of rotation of the first vane device relative to the second vane device, when comparing the resulting compression chamber pressure of differing pre-charge gas pressure values. This is one example of what is meant by the term "tunable" actuator joint module, because the example actuator joint modules discussed herein can be tuned to have a particular joint stiffness value by selecting the amount of gas pressure charged in (or removed from) the chambers of the actuator joint modules, as will be appreciated by the examples and discussion herein.

Upon rotation of the input member 136a relative to the output member 136b about the axis of rotation 137 (e.g., in the counter clockwise direction of FIG. 11B), the quasi-passive elastic actuator can be engaged so as to cause the first vane device 164 to rotate (e.g., the first vane device 164 can be caused to rotate approximately 90 degrees, for instance (in practice, the rotation may be more or less than 90 degrees)). Such rotational movement can be the result of a gait movement, external forces, or other type of movement, that causes a first support member to rotate about a second support member, such as between the points A to B of FIG. 3A. That is, the input and output members 136a and 136b would rotate relative to each other, as being secured to respective first and second support members of a robotic assembly, for instance (e.g., FIG. 4A). Accordingly, upon such rotation, gas (e.g., air, nitrogen, carbon dioxide, argon, Freon, a mixture of gases, etc.) within the compression chamber 264a can be compressed between the first vane device 164 and the second vane device 229, thereby storing energy therein, as illustrated in FIG. 11B (the compressed gas exhibiting spring-like behavior). And, upon a second gait movement, such as between points B to C of FIG. 3A, the input member 136a is initiated to rotate relative to the output member 136b in the opposite direction (i.e., clockwise direction) (again, rotating in the opposite direction is not required as energy can be stored and released during rotation in the same direction in other examples). Accordingly, with the elastic actuator engaged (either still engaged, or engaged selectively at a later time), compressed gas in the compression chamber 264a expands, thereby releasing stored/potential energy harvested during the first rotation or gait movement. This expanding gas pushes or causes a biasing force to the elongated vane 254 of the first vane device 164. As a result, a torque is exerted by the first vane device 164 relative to the second vane device 229 to rotate the second vane device 229 and the attached housing 170, which consequently applies the augmented torque to the output member 136b. Notably, during rotation of a particular joint module, the spring stiffness of the joint module is varied because of the nonlinear manner (with the valve assembly in the fully closed position) in which energy is stored when continually compressing gas in a compression chamber. Thus, the spring stiffness will vary through the various degrees of compression and expansion cycles as the quasi-passive elastic actuator is actuated during various degrees of rotation of the joint module and corresponding joint.

In some examples, the manufactured position of the second vane device 229 can be selected at a certain position to achieve a desired elastic response. For instance, the second vane device 229 can be fixed to the housing 170 at less than or greater than 180 degrees relative to the elongated vane 254 of the first vane device 164, thus increasing or decreasing the disparity between the expansion and compression volumes, or in other words, providing different and unequal compression and expansion chamber volumes. This can be advantageous for users having differing knee heights and differing gait types, or for task-specific movements, such as crouching and jumping where knee joint rotation may be greater than merely walking or running. Moreover, locating the second vane device 229 at different positions relative to the first vane device 164 when the valve assembly is closed can produce linear or nonlinear responses or output. With disparate compression and expansion chamber volumes, the differential pressure can evolve more rapidly, particularly when the expansion chamber volume is relatively small, since the volume ratio is higher than the compression side for the same rotor rotation. This means that a lower charge pressure can be implemented to attain the same pneumatic spring stiffness as would be obtained if the volumes were equal.

For example, assume in one non-limiting example that the second vane device 229 is initially positioned 90 degrees relative to the first vane device 164 (see FIG. 11B as a reference to show such possible initial position), and that the total volume of the housing body 226 is approximately 137 cc. Accordingly, the compression chamber 264a can comprise a larger volume (e.g., approximately 108 cc) than the expansion chamber (e.g., approximately 29 cc). The pre-charge pressure of the compression and expansion chambers 264a and 264b can be approximately 1646 psi, thereby producing an 1854 psi peak at 20 degrees rotation, which produces 140 N-m of torque. This pre-charge pressure of 1646 psi can accomplish a targeted joint stiffness of 7 N-m/deg. Positioning the second vane device 229 a position other than 180 degrees apart relative to each other provides disparate expansion and compression chamber volumes, which maintains lower charge and actuation pressures (as compared to the "180 degree" positioning example and substantially equal volumes) because the first vane device 164 requires about half the rotational movement to achieve the same amount of energy storage about the compression chamber 264a as compared to if the volumes were equal. This can also reduce or minimize the size and weight of a particular quasi-passive elastic actuator because a smaller chamber volume is possible. This is another example of what is meant by the term "tunable" actuator joint module, because the example actuator joint modules discussed herein can be tuned to have a particular joint stiffness value by selecting the initial or starting position of the second vane device 229 relative to the first vane device 164, as will be appreciated by the examples and discussion herein.

In one example, as shown in FIGS. 14A and 14B (and with continued reference to FIGS. 4A-11B), a pair of small ring seals 259 can each be disposed on either side of the first vane device 164 to seal gas from transferring between (or exiting) the compression and expansion chambers 264a and 264b, respectively. Likewise, another pair of larger ring seals 261 can each be disposed on either side of the cylindrical body portion 252 to seal gas from transferring between the chambers 264a and 264b, thereby providing two stages of sealing. The elongated vane 254 can have a seal member 263 positioned through a slot extending through a central area of the vane 254 to seal gas from transferring between chambers 264a and 264b. Likewise, the second vane device 229 can also comprise a seal member 265 disposed in a groove around the perimeter of the second vane device 229 to seal areas of contact around the second vane device 229 on all four vertical/lateral sides.

As discussed above, the primary actuator 134 can be operated to apply a primary torque (along with the augmented torque) to rotate the output member 136b about axis of rotation 137. In this manner, a splined ring gear 268 can be coupled to the housing body 226 via keys 270 (FIG. 10A) that mate the splined ring gear 266 about an annular interface portion 272 of the housing body 226. The splined ring gear 266 can be rotatably coupled with the primary pulley 216 (of the primary actuator 134) via the transmission belt 224. Therefore, upon the desired or selected second gait movement, the quasi-passive actuator 134 applies the augmented torque concurrently with the torque of the primary actuator 134 to actuate the tunable actuator joint module 130 about the axis of rotation 137. Because the torque applied by the primary actuator 132 is supplemented with the augmented torque applied by the quasi-passive elastic actuator 134, the motor 178 can be selected from a group of smaller motors (e.g., having less power dissipation) than would otherwise be needed within a joint module not having an elastic actuator for accomplishing the same task or function of the robotic assembly, which further contributes to the compact configuration of the module 130.

For instance, the motor 178 can be a Brushless DC motor (BLDC), such as a Permanent Magnet BLDC sold by Allied Motion (MF0127-032) having a 95 mm outside diameter and a 32 mm think frameless motor with torque in the range of 40 to 60 N-m, and peak torque as large as 90 N-m, and with winding optimized to achieve the desired maximum torque and speed while operating using a 48 VDC supply and a high performance COTS controller. The motor coils can be rated for operation up to 130 deg. C., so the motor may be able to operate continuously while running even at ambient temperature as high as 50 to 60 deg. C. (122 to 140 deg. F.) but ideally at a steady state temperature of approximately 40 degrees C. above ambient. Of course, this is only one specific example that is not intended to be limiting in any way.

In one example of power usage, assume a lower body exoskeleton (e.g., FIG. 4A) includes left and right hip joints for flexion/extension, and knee joints for flexion/extension, where each of these joints comprises a tunable actuator joint module as discussed herein. While walking at approximately 3.5 mph, the total power usage to actuate each hip joint is approximately 90 W per gait cycle, while operating at approximately 40 degrees C. above ambient. And, the total power usage to actuate each knee joint is approximately 70 W per gait cycle, while operating at approximately 60 degrees C. above ambient. Thus, the total average power for two exoskeleton legs (while walking) is approximately 320 W (i.e., 90+90+70+70). Therefore, the energy used per meter while walking is approximately 213 J/m (or a travel distance of approximately 17 km/kW-hr used).

While running at approximately 6 mph, the total power usage to actuate each hip joint is approximately 150 W per gait cycle, while operating at approximately 70 degrees C. above ambient. And, the total power usage to actuate each knee joint is approximately 145 W per gait cycle, while operating at approximately 60 degrees C. above ambient Thus, the total average power for two exoskeleton legs (while running) is approximately 590 W.

These same two example operating conditions (walking and running) can be achieved with a tunable actuator joint module weighing approximately 5.08 kg (or less depending on material choices and other variables), and having a max torque of 300 N-m for the primary actuator (e.g., motor and one planetary transmission). The maximum torque for the quasi-passive elastic actuator (i.e., that which applies an augmented torque) can be 460 N-m for a hip joint (with a 645 psi pre-charge), and 350 N-m for a knee joint (with a 1525 psi pre-charge). These results are with a maximum speed of 600 degrees/second for each hip and/or knee joint. In some examples, the pre-charge pressure can be up to 3000 psi, with a burst pressure of 5000 psi or less. Note that the ankle joints can have the performance results discussed below regarding the linear pneumatic actuator of FIGS. 20A-20F.

In some examples, a second transmission, such as a second planetary transmission, can be incorporated with the primary actuator 132 to provide further gear reduction. For instance, a low or high drive second planetary transmission could be coupled to the output (e.g., carrier) of the planetary transmission 186, and the output of the second planetary transmission could be coupled to the output shaft 210. Thus, such cascaded planetary transmissions and the transmission belt 224 can provide a three stage gear reduction from the original output torque and speed of the motor 178.

In the example illustrated in FIGS. 6A-10B, the planetary transmission 186 can be a 4:1 transmission with the belt 224 providing a 2.05:1 transmission reduction (as a result of the larger diameter of the gear ring 268 and the smaller diameter of the output pulley 216, as discussed above). The resulting ratio gear reduction from the motor 178 to the output member 136b can be 8.2. In an example where the motor 178 is a 48V motor (and Allied Motion's motor mentioned above), the maximum output torque can be approximately 342 N-m, and the maximum output speed can be 1008 degrees/second. This example is not meant to be limiting in any way. In another example, the belt 224 can provide a 1:1 transmission reduction, or it can vary from this ratio. Likewise, the planetary transmission can be a 3:1 or a 5:1 (or even greater ratios), as mentioned above. As will be recognized by those skilled in the art, and similar to the first transmission discussed above, other types of transmission types can be incorporated and used as a second transmission. In some examples, other frameless, brushless motors (or other types of primary actuator types (e.g., hydraulic, pneumatic)) can be incorporated, as discussed above, to generate a maximum output torque that is greater or less than 342 N-m, and greater or less than a maximum output speed of 1008 degrees/second, depending on the particular requirements of the joint to be actuated.

Figure 12A:
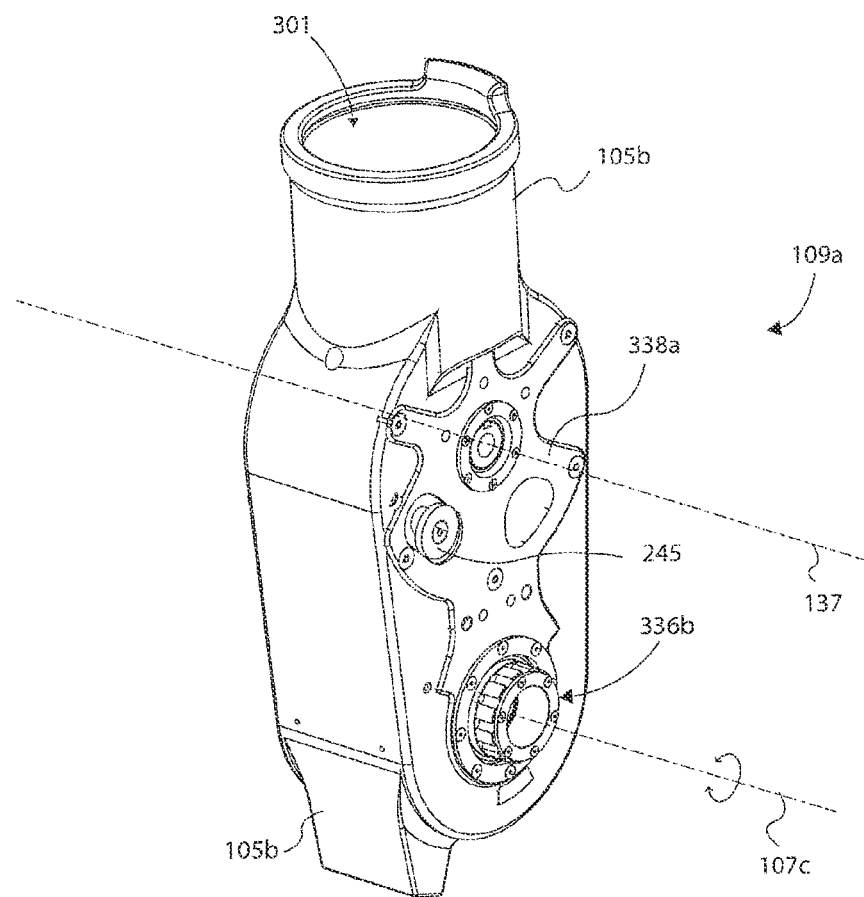
FIG. 12A is an isometric view of a the tunable actuator joint module operable with the robotic assembly of FIG. 4A in accordance with an example of the present disclosure.
Figure 12B:
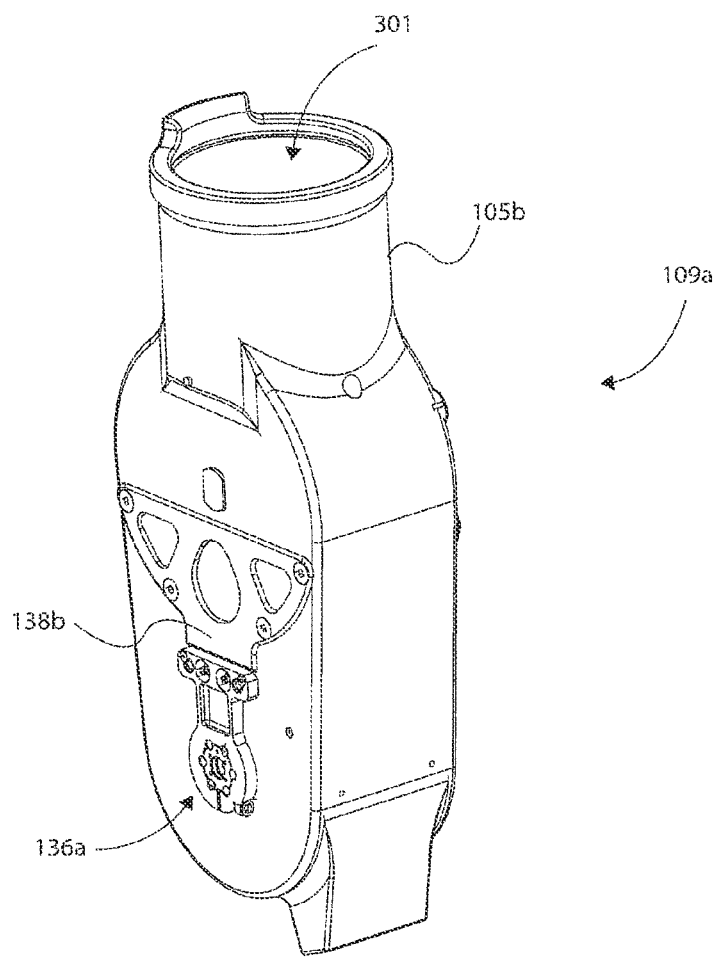
FIG. 12B is an isometric view the tunable actuator joint module of FIG. 12A.
Figure 12C:
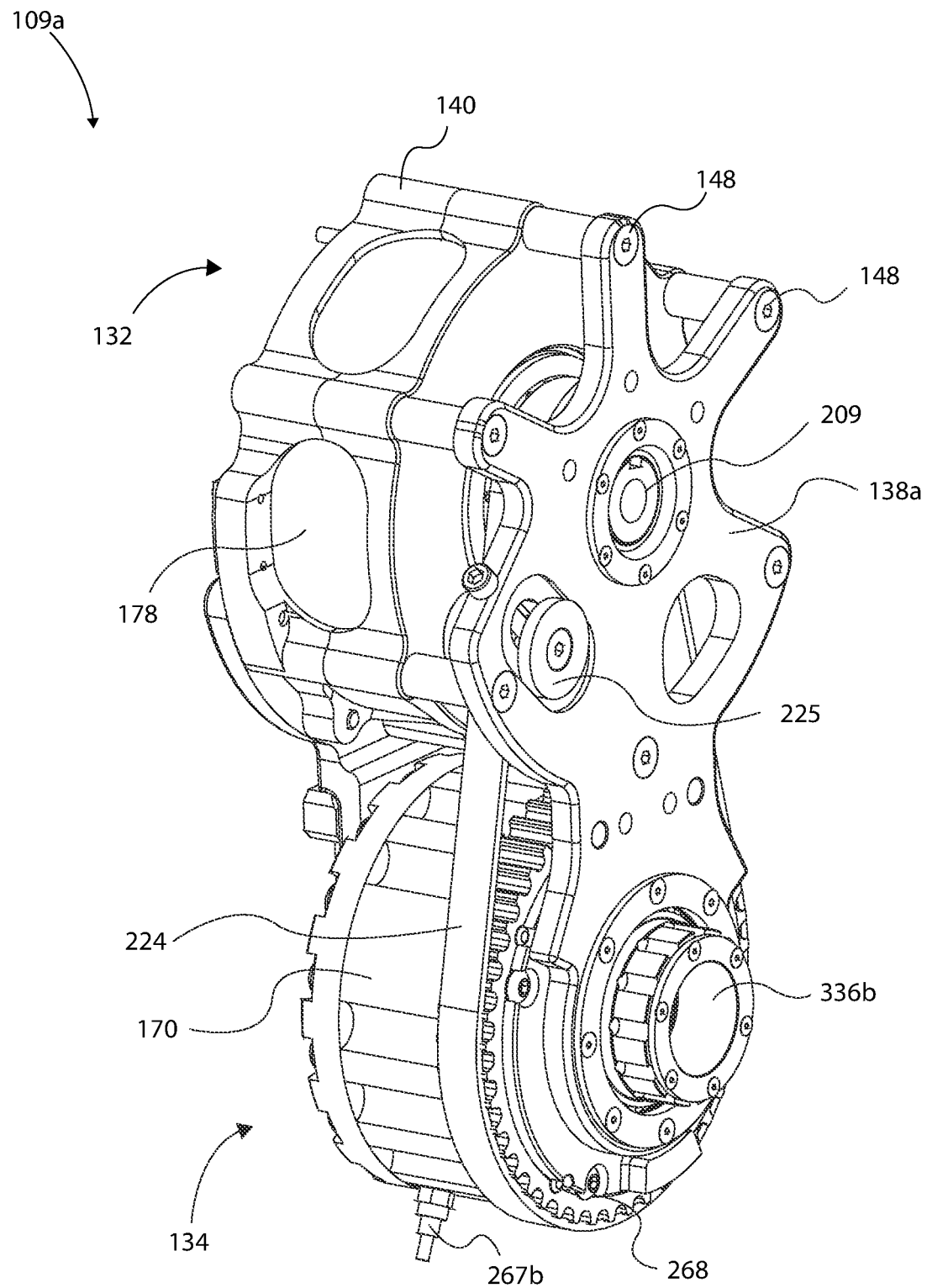
FIG. 12C is an isometric view the tunable actuator joint module of FIG. 12A.
Figure 12D:
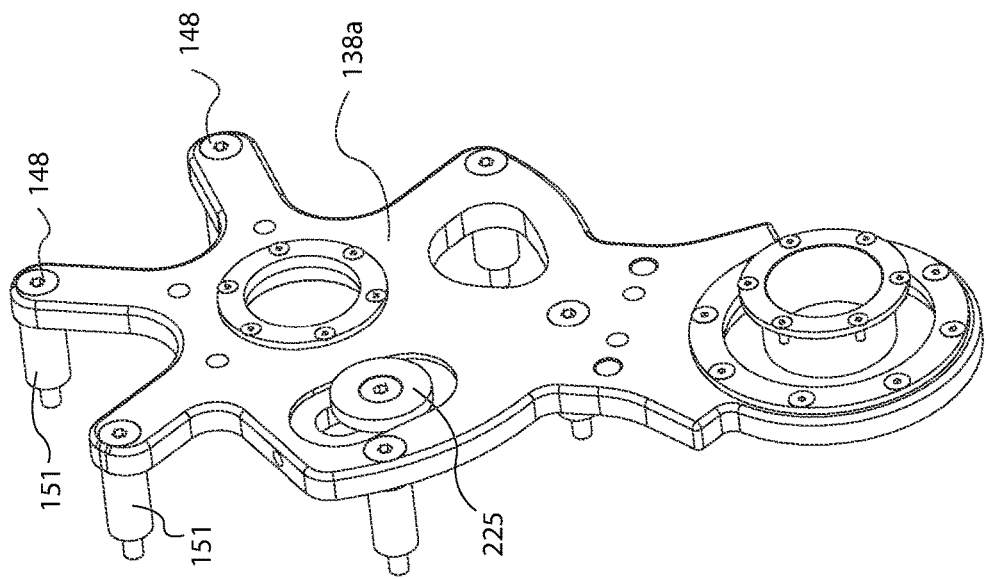
FIG. 12D is a partial exploded view the tunable actuator joint module of FIG. 12A.
Figure 12D:
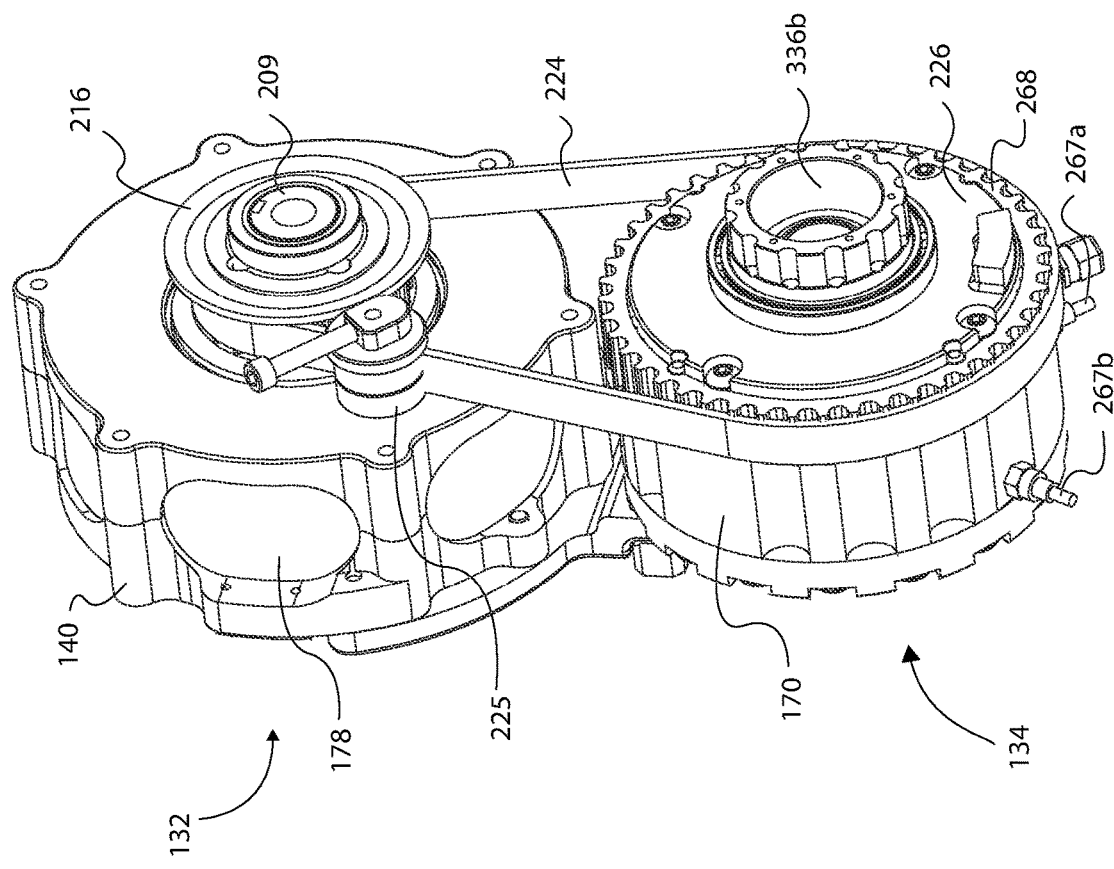
Figure 12E:
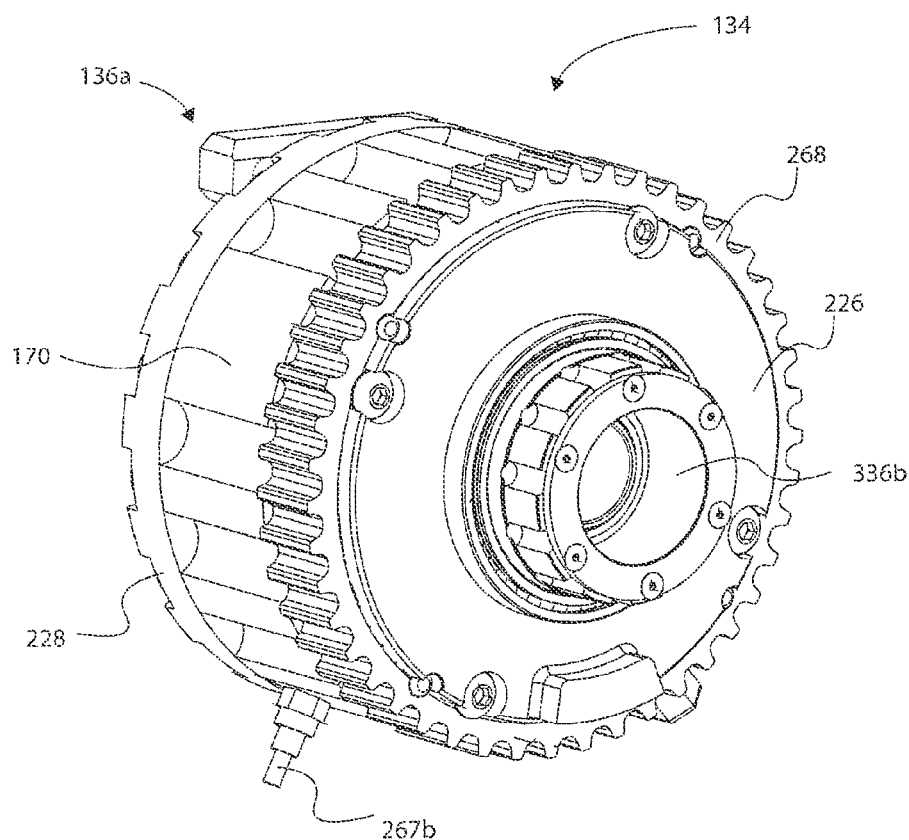
FIG. 12E is an isometric view of the quasi-passive elastic actuator of the tunable actuator joint module of FIG. 12A.
Figure 12F:
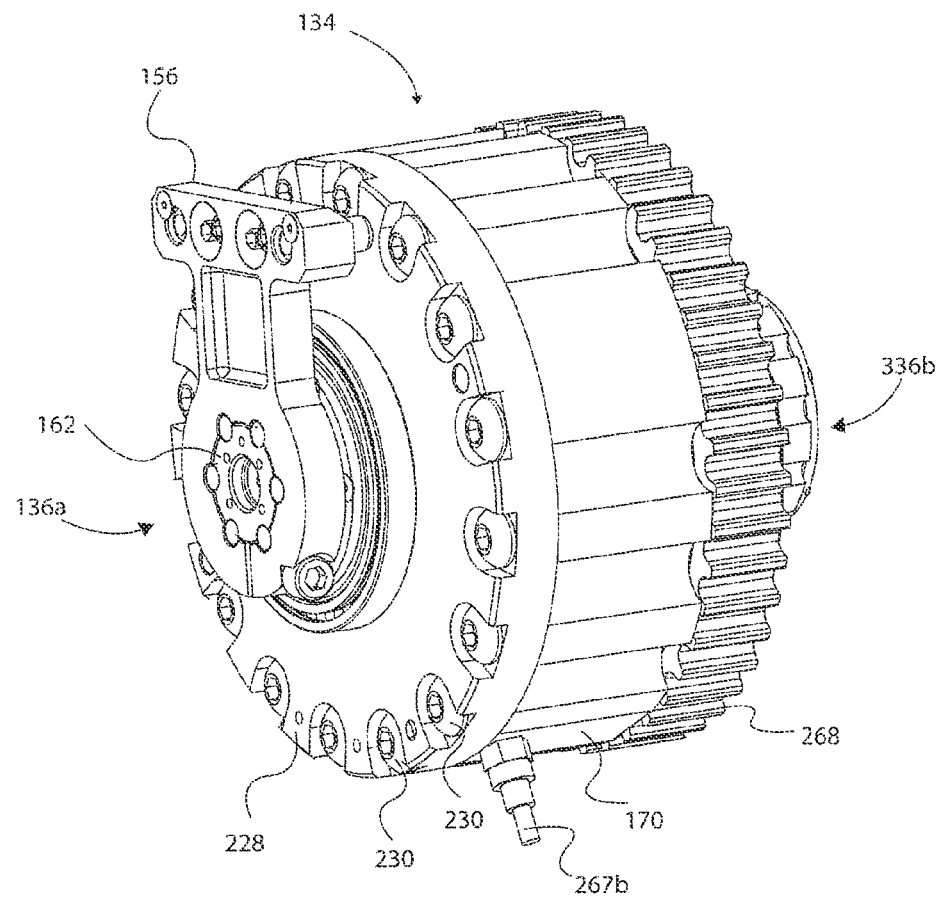
FIG. 12F is an isometric rear view of the quasi-passive elastic actuator of the tunable actuator joint module of FIG. 12A.
Figure 13A:
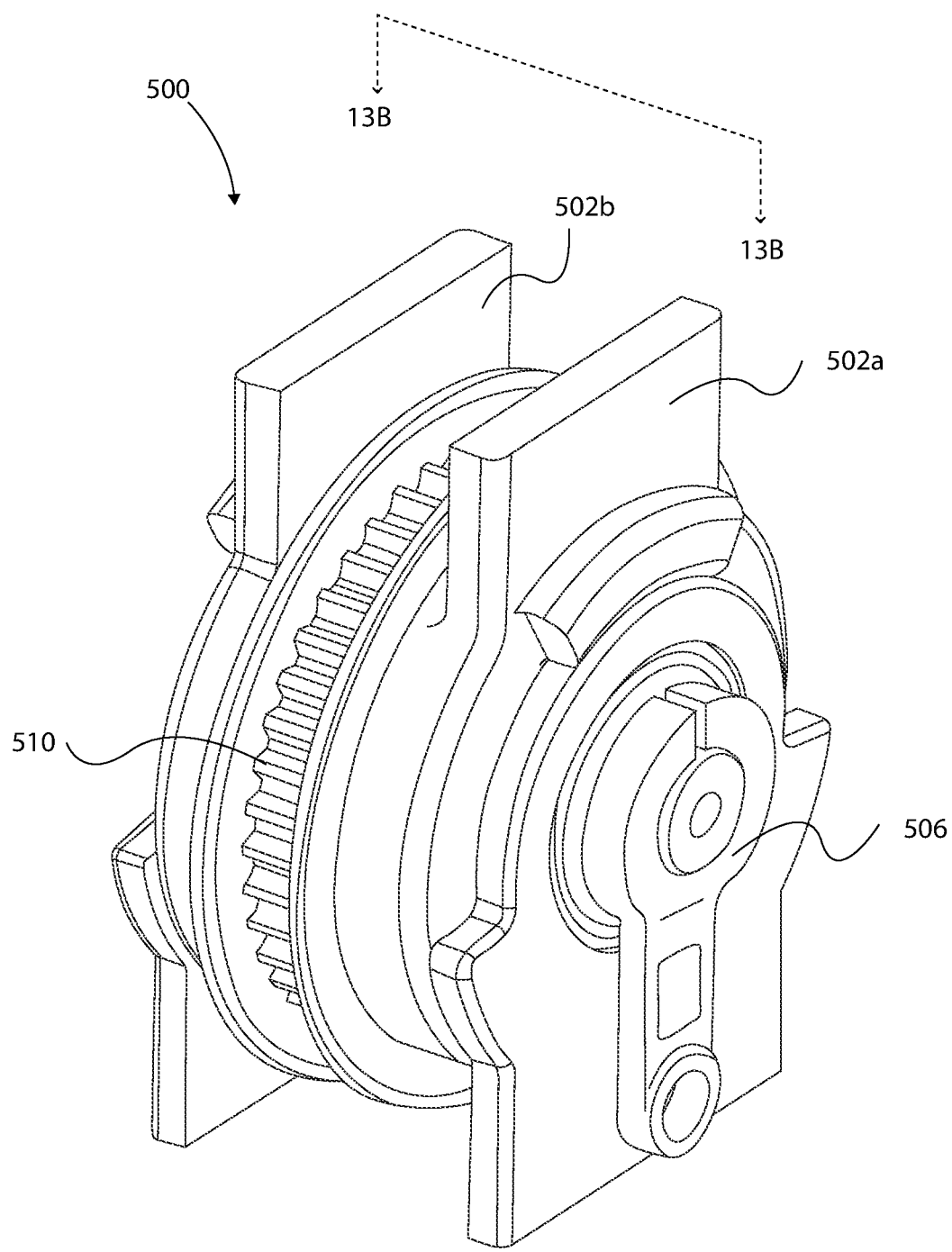
FIG. 13A is an isometric view of a tunable actuator joint module operable with the robotic assemblies of FIGS. 1 and 4A in accordance with an example of the present disclosure.
Figure 13B:
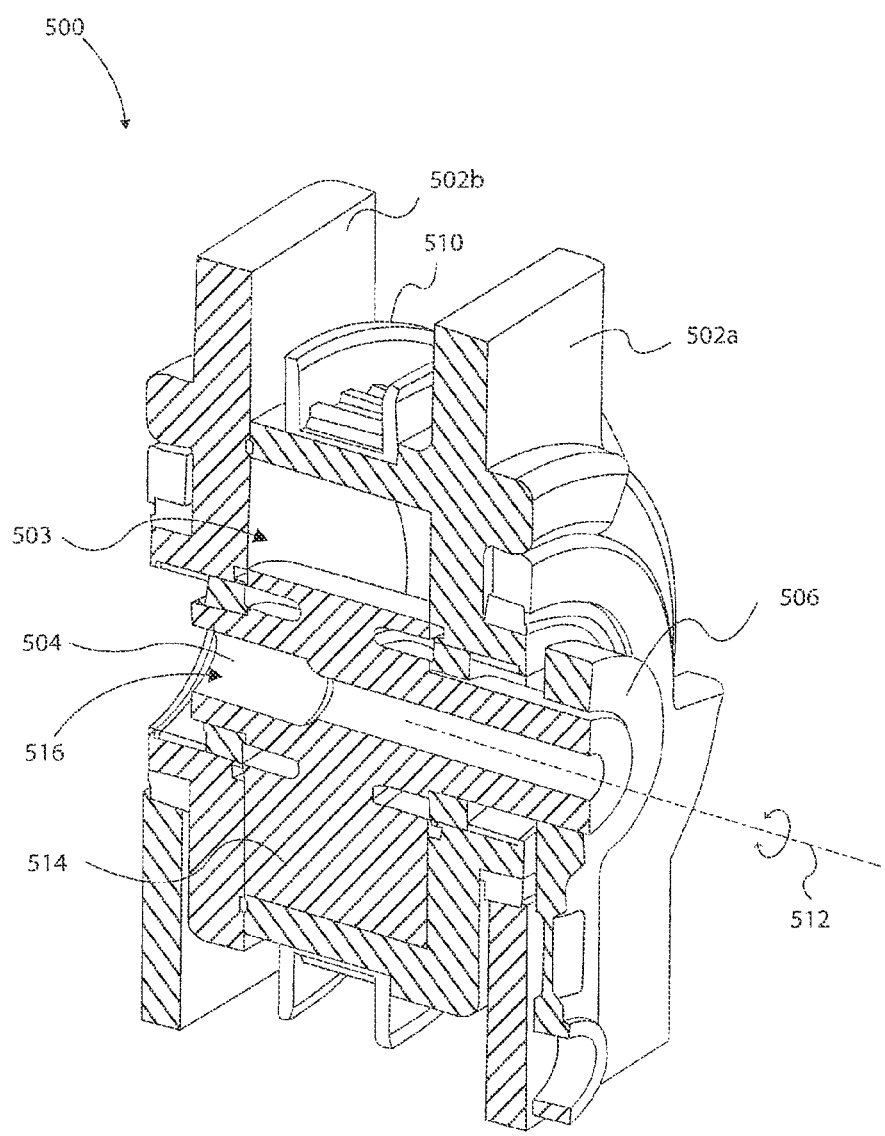
FIG. 13B is a cross-sectional view of the tunable actuator joint module of FIG. 13A taken along lines 13B of FIG. 31A.

FIGS. 12A-12F show various views of the tunable actuator joint module 109a, as exemplified in FIGS. 4A-5B as an actuator for a knee joint of a robotic assembly. The support member 150b (FIGS. 4A and 5A) can structurally support the tunable actuator joint module 109a by being fastened or otherwise secured or coupled to the tunable actuator joint module 109a, such as to mounting plates 338a or 338b or both. The support member 150b can comprise an opening 301 that receives and supports other structural support members, such as an exoskeleton as shown in FIGS. 4A and 5A. The tunable actuator joint module 109a can have substantially all the same components and functionality as described above regarding the tunable actuator joint module 130, except that the output member 336b of the quasi-passive elastic actuator 134 is formed as part of the housing 370, as best shown in FIG. 12E. Either way, the input member 336a and the output member 336b rotate about axis 107c, as in FIGS. 4A and 12A.

It should be appreciated that many of the components and functionality of the tunable actuator joint module 130 described above regarding FIGS. 6A-11B can be readily incorporated with the tunable actuator joint module 109a of FIGS. 12A-12F. To this end, FIGS. 12A-12F will not be discussed in great detail; however, the same components are labeled in FIGS. 12A-12F as corresponding to the same components of the tunable actuator joint module 130 of FIGS. 6A-11B.

Thus, the quasi-passive elastic actuator 134 and the primary actuator 132 are operative to apply a torque to rotate the input member 136a relative to the output member 336b, which can rotate support member 105c (FIG. 4A) relative to support member 105b, for instance. Or, the quasi-passive elastic actuator 134 can be operable to apply a braking force to restrict rotation of the input member 136a relative to the output member 336b. Note that the only substantive difference between the example of FIGS. 12A-12F and the example of FIGS. 6A-11B is the fact that the output member 336b is formed as part of the housing body 226 of the housing 170 (as opposed to coupled to and extending from the housing body 226, as shown with output member 136b regarding FIGS. 6A-11B). In this manner, output member 336b can be coupled to one side of support member 150c (FIG. 5A), and input member 336 can be coupled to the other side of support member 150c (FIG. 5B). Although not shown in FIGS. 12A-12F, the quasi-passive elastic actuator 134 can support a first vane device (e.g., 164), second vane device (e.g., 229), and a valve assembly (discussed below) disposed through the first vane device, and controllable to switch the quasi-passive elastic actuator 134 between inelastic and elastic states, similar to or the same as the quasi-passive elastic actuator of FIGS. 6A-11B.

Notably, the quasi-passive elastic actuator 134 can be positioned laterally adjacent a human knee joint (while wearing the exoskeleton of FIG. 4A), such that the axis of rotation 107c is at or near the axis of rotation of the human knee joint. This can minimize the moment of inertia of one support member 105b relative to the coupled adjacent support member 105c because the axis of rotation 107c is positioned at or near the axis rotation of the human knee joint, so less work/power is required as compared to exoskeleton joints that are not positioned at or near the axis of rotation of the human knee joint. This also positions the mass of the tunable actuator joint module 130 near the axis of rotation of the human knee joint, which can also assist to minimize the power requirements of the primary actuator to actuate the joint module 130 because less work/power is required to actuated the tunable actuator joint module 130 as compared to exoskeleton joints having a mass positioned distally away from the axis of rotation of the human knee joint.

FIG. 13A shows another example of a quasi-passive elastic actuator 500, and FIG. 13B shows a vertical cross sectional view of the quasi-passive elastic actuator 500 along lines 13B-13B of FIG. 13A. The quasi-passive elastic actuator 500 is similar to and can function in a similar manner as the quasi-passive elastic actuator 134 of FIG. 6A (and the quasi-passive elastic actuator 109a of FIG. 5A), such that it is operable with a primary actuator (e.g., 132) to apply an augmented torque to actuate a tunable actuator joint module (not shown herein, but see, for example, the tunable actuator joint modules 109a, 130 discussed above), or to apply a braking force to restrict rotation of the input member relative to the output member within the tunable actuator joint module, as described herein. As such, the above discussion can be referred to in understanding the quasi-passive elastic actuator 500. The quasi-passive elastic actuator 500 can comprise a first housing body 502a rotatably coupled to a second housing body 502b, and defining a cavity 503 that can be pressurized to a desired gas pressure (as described above). A first vane device 504 can be rotatably supported on either end by each of the housing bodies 502a and 502b. An output member 506 can be coupled to an output end of the first vane device 504.

The second housing body 502b can operate as an input member (e.g., as part of, or coupled to, a robotic support member), and can be coupled to the other end of the first vane device 504. A second vane device (not shown here, but similar to FIG. 10B) can be coupled to the first housing body 502a and can be operable with the first vane device 504, such as is described above, with respect to FIGS. 10A-11B. The output member 506 can be coupled to a support member, which can be coupled to, or be part of, a robotic support member (e.g., a lower leg member). An annular ring gear 510 can be secured to the first housing body 502a, and can be coupled to a primary actuator (e.g., 132) via a torque-transfer device (e.g., belt 224).

Therefore, similarly as described above regarding the tunable actuator joint module 130, upon rotation of the input member in the form of the second housing body 502b relative to the output member 506 about an axis of rotation 512, the first vane device 504 can be caused to rotate. Such rotational movement can be the result of a gait movement of a robotic assembly, such as between points A and B of FIG. 3A. That is, the input and output members can rotate relative to each other, as being secured to respective first and second support members, for instance (e.g., see FIG. 4A). Accordingly, upon such rotation, gas within a gas compression chamber (e.g., 264a of FIG. 11B) is compressed between the first vane device 504 and the second vane device (e.g., 229), thereby storing energy therein (or generating a braking force). Upon a second gait movement, such as between points B to C of FIG. 3A, the input member in the form of the second housing body 502b is initiated to rotate relative to the output member 506, such as in the opposite direction (again, rotation may be in the same or different directions). Accordingly, compressed gas in the gas compression chamber expands to release potential energy stored therein. This expanding gas pushes or causes a force to be exerted on an elongated vane 514 of the first vane device 504. As a result, a torque is exerted by the first vane device 504 relative to the second vane device (e.g., 229) to rotate the first housing body 502a and to apply an augmented torque to the output member 506 that supplements the torque provided by the primary actuator to rotate the input and output members during the second gait movement.

During such second gait movement, a primary actuator (e.g., 132) rotates the transmission belt, which rotates the annular ring 510 to apply a primary torque to rotate the first housing body 502a, which exerts a torque to rotate the output member 506. The first vane device 504 can comprise an opening 516 that can support and receive a valve assembly to selectively control operation of the quasi-passive elastic actuator 500, as further detailed below. As such, and although not shown here, the quasi-passive elastic actuator 500 can comprise a valve assembly similar to those described herein.

With reference to FIGS. 10A-11B, and particular reference to FIGS. 14A-23, discussed are various valve assemblies that can be incorporated with any of the quasi-passive elastic actuators discussed herein (e.g., 109a, 134, 500). The following description of such valve assemblies will be described with reference to each of their respective figures, as well as FIGS. 10A-11B, which describe and illustrate the exemplary tunable actuator joint module 130 and the quasi-passive elastic actuator 134, these being included in the description for the sake of simplicity and clarity, although they are intended only as one example of a joint module capable of implementing any one of the valve assemblies discussed below and shown in FIGS. 14A-23.

As taught herein, the tunable actuator joint module 130 can be switchable between an elastic state, a semi-elastic state, and an inelastic state with the assistance of a control system operatively coupled to the quasi-passive elastic actuator 134 for selectively controlling application of the augmented torque or the braking force (e.g., during selective portions of a gait cycle, during a lifting task, during a climbing task, in response to an external load acting on the robotic system (including gravity), or during other movements by a robotic device or system). The control system can comprise any one of the valve assemblies discussed herein, a first vane device (e.g., see first vane device 164), and a controller (not shown) for controlling operation of a particular valve assembly. The controller can be part of a computer system on-board the robotic system, such as onboard an exoskeleton, or remotely located, such as could be the case in a teleoperated or humanoid type of robotic system, for instance. The valve assemblies can comprise pneumatic valves operable to switch the mode of operation of the quasi-passive elastic actuator, such as between that of a spring (valve closed), that which facilitates free swing of a limb (valve opened) or that of a damper or brake (valve partially opened).

Each of the valve assemblies provides or facilitates a "clutch" or "brake" type of capability that permits gas to transfer (i.e., shunt) back and forth between the compression and expansion chambers, via what is termed a shunt circuit, when the valve assembly is opened, or partially opened, and for gas to be restricted and compressed to compress the elastic component, when the valve is closed, or partially open or closed, such as to provide controlled and variable damping or braking when the valve is partially opened or partially closed. The shunt circuit can be defined, at least in part, by the flow pathways of the gas between the quasi-passive actuator and one or more of its components, including the valve assembly and one or more of its components. Different valve assemblies can comprise different flow paths, and thus differently configured shunt circuits. As such, the quasi-passive actuator can comprise a shunt circuit that can be opened (the elastic component is caused to enter the inelastic state), closed (the elastic actuator is caused to enter the elastic state), or partially opened (causing the elastic actuator to enter the semi-elastic state to act as a damper and/or brake) by the selective and variable control or operation of the valve. Spring stiffness can be a function of piston (first vane device) and chamber geometries, as well as gas pressure charge. Thus, the magnitude of stiffness for a given joint is adjustable, such as for mission specific payloads and terrain-specific gaits while the active valve controls exactly when that stiffness is engaged for energy recovery during the support phase and when it is disengaged during the ballistic or free swinging phase. The valve assemblies discussed herein provide the tunable joint module with the ability to rapidly vary the characteristics of the quasi-passive actuators between that of a near free joint to that of a nominally linear elastic element (when opened or partially opened). This results in power operation of the joints of the robotic system (e.g., shoulder, elbow, hip, knee and ankle joints) that is relatively low compared with prior joints that do not have a quasi-passive elastic actuator.

The valve assemblies discussed herein can be operated and controlled to be closed, thereby facilitating application of an augmented torque, regardless of whether the primary actuator is operated to apply a primary torque. Thus, the term "augmented" is not meant to be limited to applying a supplemental or additional torque with the primary torque, because the augmented torque may be the only torque applied to actuate a particular clutched joint module. For instance, after an exoskeleton's upper body is used to lower a load (thereby storing energy about quasi-passive elastic actuators associated with joint modules the upper body), and after the load is released by the upper body, the arms of the upper body may be moved upwardly and back to a normal position only by virtue of the "augmented torque" being applied by the associated quasi-passive elastic actuators. This is because the primary actuator may not be needed to move the arm back up to a normal position because the stored energy is sufficient for such purpose. Moreover, during such application of "only" applying the augmented torque, the associated valve assemblies can be variably controlled to desired positions (e.g., partially opened) to provide a damping force or braking force to control the speed or rate at which the respective quasi-passive elastic joint modules move, as discussed elsewhere herein. Of course, for the same movement, such can also be applied in addition to a primary torque provided by the primary actuator.

Moreover, in some examples, the valve assemblies discussed herein can be located and operable at a joint of the robotic system. In one example, the valve assembly can be supported within an opening of the first vane device of the quasi-passive elastic actuator, such that the valve is integrated into or positioned through the first vane device (and particularly within the first vane shaft), and supported in a position about an axis of rotation of the tunable actuator joint module, and particularly the quasi-passive elastic actuator. In this position, the valve assemblies can comprise an axis of actuation that is parallel, and in some cases, collinear, with the axis of rotation of the tunable joint module (and a joint of the operator in some robotic systems, such as with an exoskeleton). The axis of actuation can comprise an axis of rotation in those cases where the valve device of the valve assembly is rotatable in a bi-directional manner to open and close the valve assembly, or an axis of translation in those cases where the valve device is translatable in a bi-directional manner to open and close the valve assembly.

Figure 15A:
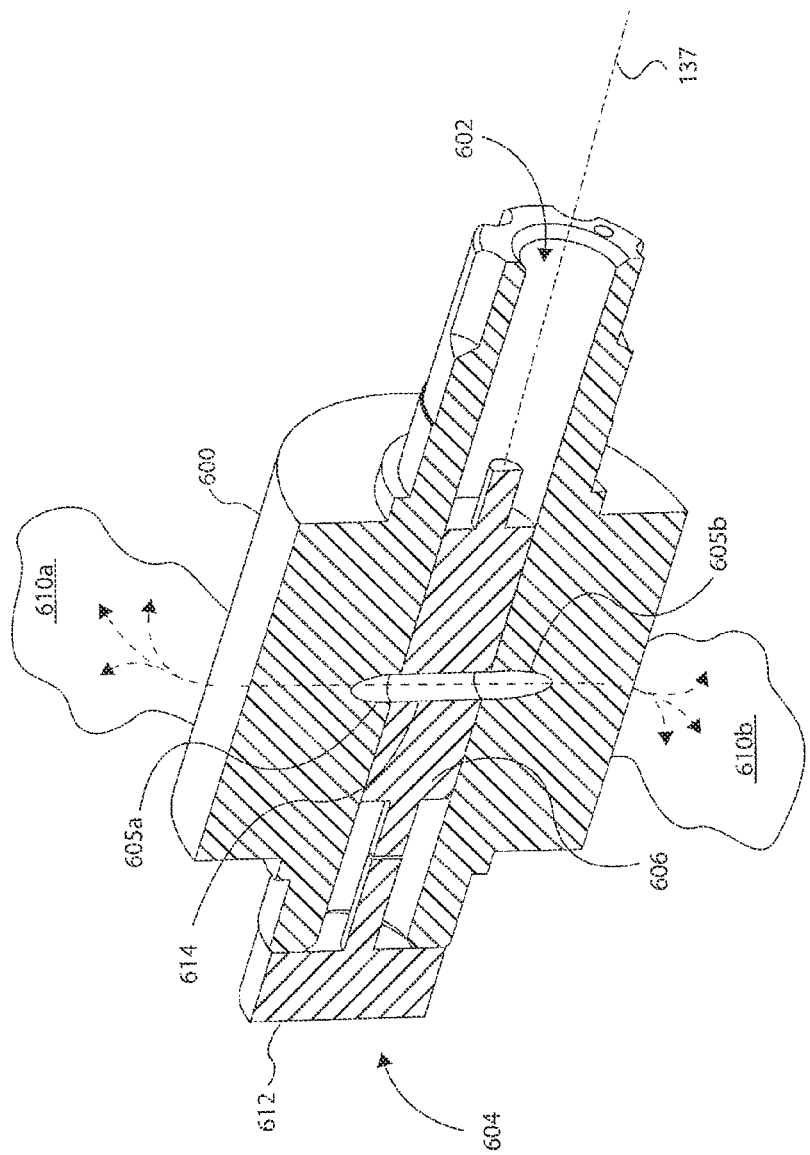
FIG. 15A is a cross-sectional view of a valve assembly operable with the first vane device of FIG. 14A in accordance with an example of the present disclosure.
Figure 15C:
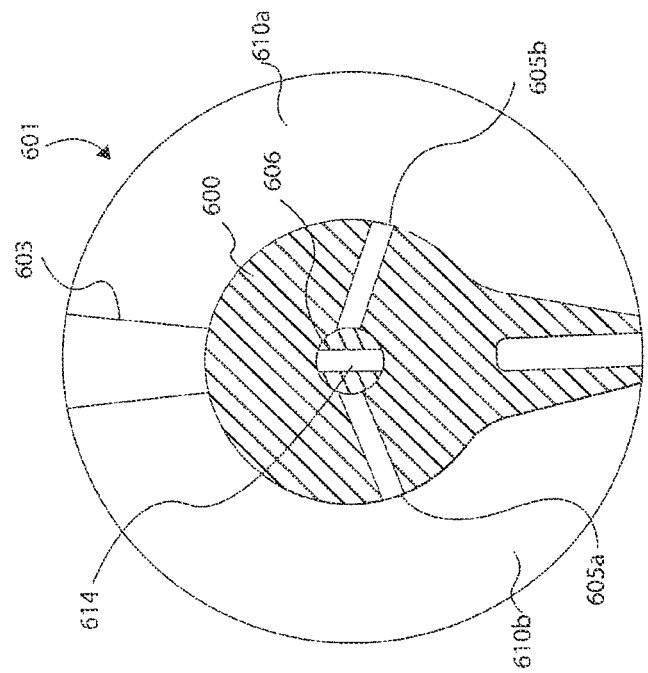
FIG. 15C schematic cross-sectional front view of the valve assembly of FIG. 15A operable with the first vane device and the second vane device of FIG. 14A, with the shunt circuit closed.
Figure 15B:
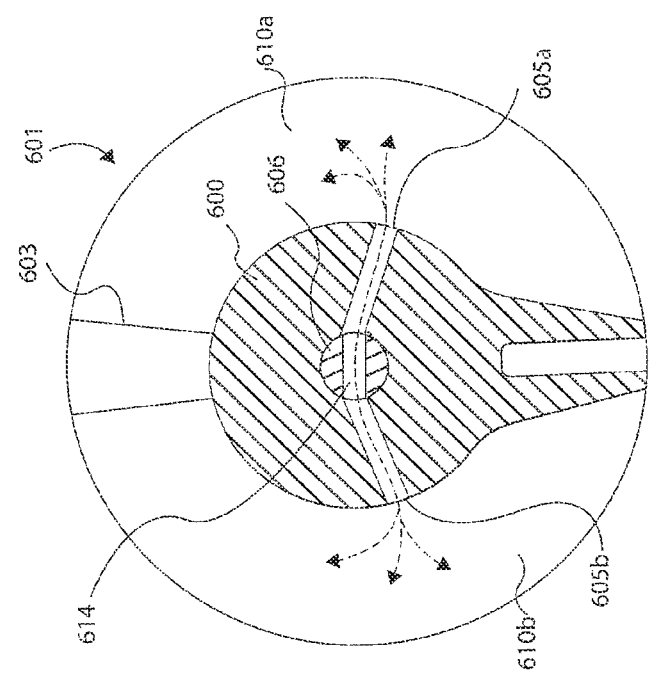
FIG. 15B is a schematic cross-sectional front view of the valve assembly of FIG. 15A operable with the first vane device and the second vane device of FIG. 14A, with the shunt circuit open, in accordance with an example of the present disclosure.
Figure 16A:
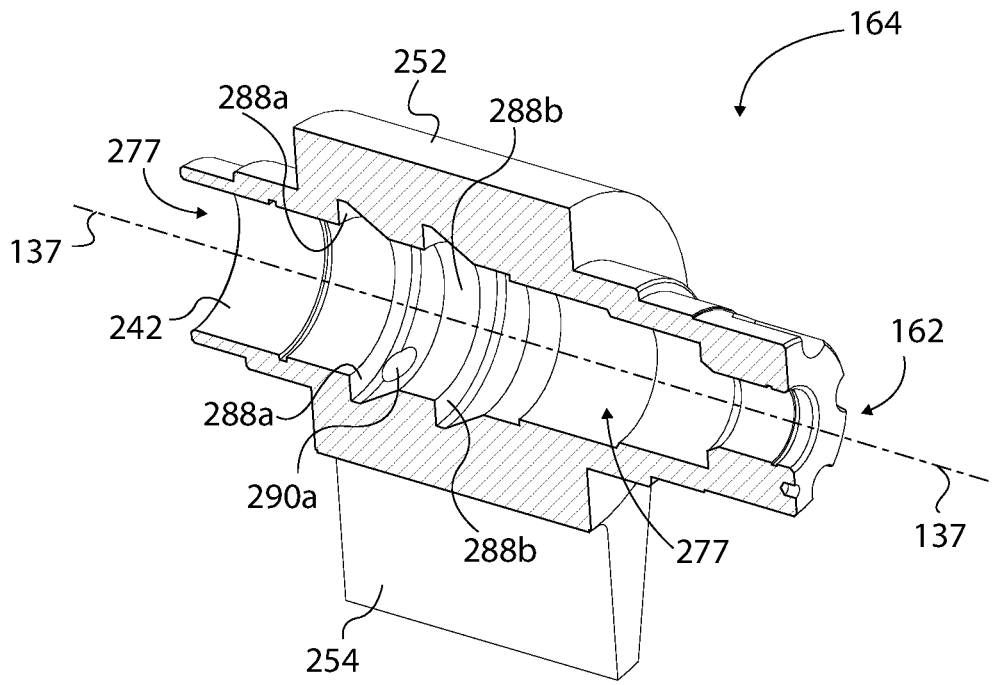
FIG. 16A is a cross sectional view (y-plane) of a first vane device (e.g., FIG. 14A) which forms part of a valve assembly in accordance with an example of the present disclosure.
Figure 16B:
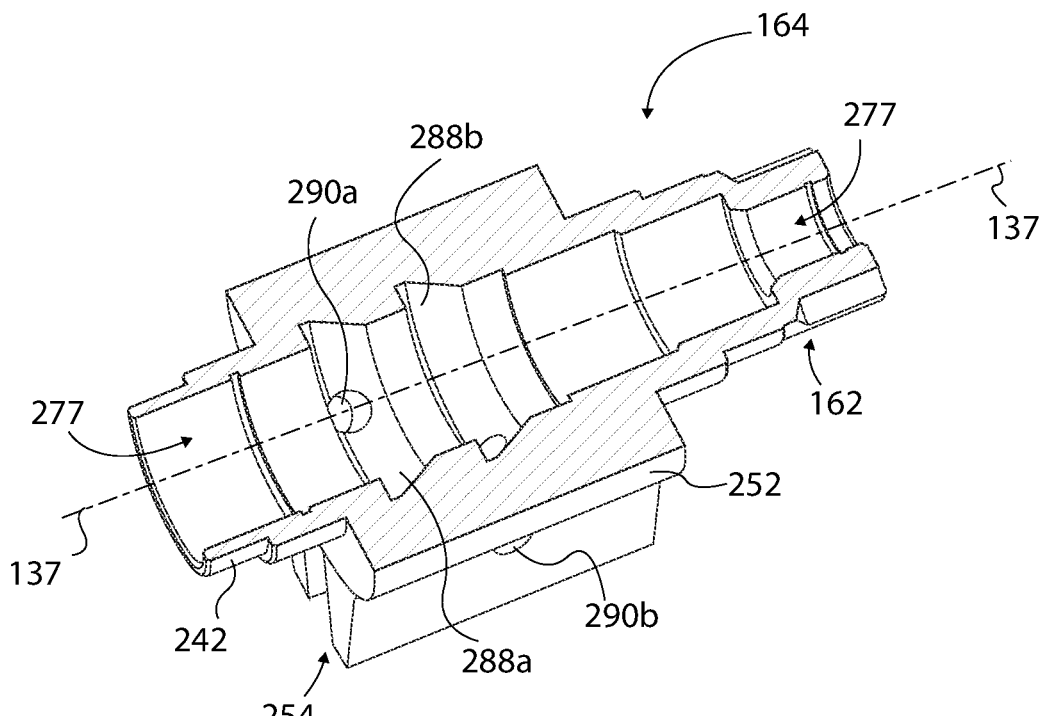
FIG. 16B is a cross sectional view (x-plane) of the first vane device of FIG. 16A.

FIGS. 15A-15C illustrate a valve assembly 604 operable with a first vane device 600 (similar to the first vane device 164 described above) in accordance with one example. In this example, the first vane device 600 comprises an opening or bore 602 extending through a central area of the first vane device 600 and along an axis of rotation 137. The valve assembly 604 comprises a valve device 606 disposed within the opening or bore 602 of the first vane device 600. The valve device 606 can comprise at least one cylindrical portion (i.e., a portion having a cylindrically configured surface) positioned through the opening 602, which interfaces with a corresponding inner cylindrical surface of the opening 602. Of course, a cylindrical cross-sectional configuration is not intended to be limiting in any way, particularly in the example configuration in which the valve device 606 translates relative to the first vane device 600. In one example, the valve device 606 can be situated about the axis of rotation 137, or at least have a portion that intersects the axis of rotation 137.

The first vane device 600 can define, at least in part, a valve body of the valve assembly 604. In this manner, the first vane device 600 can comprise a first conduit 605a in fluid communication with a compression chamber 610a (e.g., 264a of FIG. 11A), and a second conduit 605b in fluid communication with an expansion chamber 610b (e.g., the expansion chamber 264b of FIG. 11A), such that, in at least one operating state, gas can be caused to move between the compression chamber 610a and the expansion chamber 610b through, and as controlled by, the valve assembly 604 (a portion of which assembly comprises the first vane device 600). These described fluid flow paths comprise and define a part of the shunt circuit that exists between the compression and expansion chambers and the valve assembly.

The valve assembly 604 can comprise a valve actuator 612, such as a voice coil or other solenoid or electric actuator, operatively coupled to the valve device 606 to facilitate selective actuation (i.e., movement) of the valve device 606. The valve actuator 612 can actuate the valve device 606 by rotating it or by axially moving it about or relative to the opening or bore 602. Thus, the valve assembly 604 and the valve device 606 comprises an open or partially open position (FIGS. 15A and 15B) that permits at least some fluid flow (i.e., the shunting of fluid) between the compression and expansion chambers 610a and 610b. The valve device 606 further comprises a closed position (FIG. 15C) (when actuated by the actuator 612) that restricts or blocks fluid flow between the compression and expansion chambers 610a and 610b.

More specifically, the valve device 606 comprises at least one opening 614 through the valve device 606 that can be selectively positioned between an open, partially open, and a closed position. With the valve device 606 in an open position or partially open position, the opening 614 is aligned, at least in part, with the first and second conduits 605a and 605b so as to facilitate fluid communication between the compression and expansion chambers 610a and 610b via the respective conduits 605a and 605b (e.g., to open or partially open the shunt circuit, where the valve assembly functions to try to equalize pressure between the compression and expansion chambers 610a and 610b), as shown in FIGS. 15A and 15B. In the inelastic state with the shunt circuit open where gas pressure is equalized, and where there is little to no resistance to movement of the first vane device 600 relative to the second vane device 603 (i.e., gas is free to move between the compression and expansion chambers through the valve assembly as the tunable joint module is rotated), the quasi-passive elastic actuator 601 neither stores nor releases energy in the form of an augmented torque to the tunable actuator joint module 130, nor does it generate a braking force. Rather, the quasi-passive elastic actuator is in free swing mode where the first vane device 600 is freely rotatable relative to the second vane device 603, and where negligible resistance (or reduced resistance) is generated between the first vane device 600 and the second vane device 603 (and consequently negligible resistance from the quasi-passive actuator is transferred to the first and second support members rotatably coupled about the quasi-passive elastic actuator 601).

Thus, keeping with the discussion above regarding FIGS. 11A and 11B, the valve assembly 604 can be selectively controlled so that it is maintained in an open position where the shunt circuit is maintained in an open position, such that no torque assistance is provided to the primary actuator (except in cases where the valve is variably controlled in a partially open position where some residual torque exists as a damping or braking torque). In other words, the tunable actuator joint module 130 can function with only the primary actuator providing any needed torque input, or in response to an external force (e.g., an impact force, momentum or gravity that induces rotation) during a free swing mode. For example, during a portion of a gait movement, such as is desired between points D-A (FIG. 3A), the valve assembly 604 of the quasi-passive actuator can be opened (i.e., inactive) to open the shunt circuit, and to allow free swing of a joint of a robotic joint of a robotic exoskeleton, for instance.

Conversely, as illustrated in FIG. 15C, the valve device 606 can be positioned in the closed position, thereby closing the shunt circuit. In the closed position, the quasi-passive elastic actuator 601 (e.g., 109a, 134, 500) is operable in the elastic state and is active to store energy and to release energy to the tunable joint actuator module. That is, the valve device 606 is actuated (e.g., rotated or translated) by the valve actuator 612 to a closed position, such that the opening 614 formed in the body of the valve device 606 is brought out of alignment with the conduits 605a and 605b, so as to restrict fluid communication between the compression and expansion chambers 610a and 610b via the respective conduits 605a and 605b, thereby closing the shunt circuit. Thus, in this closed position, the quasi-passive elastic actuator 301 functions to store energy in the form of compressed gas pressure, and then to release the stored energy when needed in the form of an augmented torque that supplements the torque provided by the primary actuator to the tunable actuator joint module. As explained above regarding the discussion pertaining to FIGS. 11A and 11B, during a first portion of a gait movement or gait cycle, the valve device 606 can be closed so as to cause the quasi-passive actuator to store energy as the primary actuator inputs a torque to cause the tunable actuator joint module to rotate to carry out the first portion of the gait cycle. During this rotation, the rotator vane device is displaced as discussed above. Upon completion of the first portion of the gait cycle, a second portion of the gait cycle, where rotation of the tunable actuator joint module is in the opposite direction, can take advantage of the stored energy in the form of an augmented torque that is applied in the same direction as the torque input by the primary actuator, the augmented torque generated as the compressed gas attempts to place the first vane device and the second vane device in equilibrium. Indeed, both the storing and release of energy occurs with the valve assembly 604 in the closed position of FIG. 15C to engage or actuate the quasi-passive actuator. Although not shown, the valve device 606 of the assembly 604 can be placed in a position so as to partially open the shunt circuit, wherein rotation of the joint causes the quasi-passive elastic actuator 301 to be partially actuated to store (and in some cases to also release) some energy that can be applied to the joint as a braking force.

It is further noted that the valve device 606 can be, in some examples, strategically positioned about an axis of rotation 137 of the tunable actuator joint module and the robotic joint. For example, where the valve device 606 is rotated by the valve actuator 612, the valve device 606 (or at least a component of the valve device 606) has an axis of rotation that is congruent or parallel with the axis of rotation 137 of the robotic joint. Likewise, in examples where the valve device 606 is axially translated through the opening 602, the valve device 606 comprises an axis (such as an axis of translation) parallel or collinear with the axis of rotation 137 of a robotic joint (and in some cases with the joint of an operator, such as an operator operating an exoskeleton).

As discussed, in some examples, the valve assembly 604 and valve device 606 can be controlled to actively dampen rotation of a particular tunable actuator joint module. More specifically, the valve device 606 can be variably controlled to multiple different positions, between the opened and closed positions, that place the joint module, and particularly the quasi-passive elastic actuator, in a semi-elastic state, so that the compression and expansion chambers are in fluid communication with each other to some degree (e.g., the valve device being 10 percent, 20 percent, 50 percent, 75 percent "open"). This "semi-elastic state" or "damping state" of the quasi-passive elastic actuator can provide a corresponding active braking or damping force that can be varied with the varying of the position of the valve device 606 to selectively store and recover some degree of energy as desired. In the example shown, a controlled signal can be transmitted to the actuator 612 to variably control the rotational position of the valve device 606. For example, during the free swing phase the valve device 606 can be moved to a position such that the opening 614 is not completely in the open position as shown in FIG. 15B; rather, it may be rotated slightly to be partially open so that some fluid flows through the opening 614, thereby at least partially actuating the quasi-passive elastic actuator to provide a controlled damping feature or damping mode to restrict or damp absolute free movement of a particular joint module. This "active damping" can also be advantageous in task-specific movement of the robotic system, such as when lowering a load. For example, with a load being carried by an upper exoskeleton, the valve devices of the elbow and/or shoulder tunable actuator joint modules can be actively and variably controlled to a position that provides damping to control (i.e., slow down) the downward movement of the arm supporting the load. It will be appreciated that the position of the various valve device examples discussed herein can also be variably controlled between the open and closed positions in this manner to provide a controlled damping or braking force or component.

It should be noted that valve assembly (and the shunt circuit) can be also be partially opened during the release of energy from the quasi-passive actuator in order to smoothen an output response. In other words, with the joint module configured to release energy stored by the quasi-passive actuator, the valve assembly can be partially opened and the quasi-passive actuator placed in the semi-elastic state or damping mode during the release of such energy, such that the output response can be made less nonlinear, and in some cases made linear, than would otherwise be the case if the valve assembly were to be fully closed. The degree to which the valve assembly (and the shunt circuit) can be opened and the timing of this is controllable in real-time during any rotation of the joint module.

FIGS. 16A-17E illustrate a valve assembly operable with a first vane device in accordance with another example. In this example, a valve assembly 654 can comprise a valve device 656. At the outset, the valve device 656 can comprise the same or similar features described above regarding valve device 606. Moreover, the valve assembly 654 is shown as being operable with the specific first vane device 164 described above (see FIGS. 16A and 16B).

The first vane device 164 can comprise a portion of the valve assembly 654, or in other words, the first vane device 164 can form a part of or can comprise a component of the valve assembly 654. In one example, the first vane device 164 can define, at least in part, a valve housing configured to house and facilitate operation of the valve device 656. Specifically, the first vane device 164 can comprise a first channel 288a formed annularly about an opening or bore 277 formed through a central area of the first vane device 164. The first vane device 164 includes a compression chamber conduit 290a (see also FIGS. 14A and 14B) that can be in fluid communication with a compression chamber as discussed herein. Similarly, a second channel 288b is formed annularly about the opening 277 and includes an expansion chamber conduit 290b (see also FIG. 14B) that can be in fluid communication with an expansion chamber as discussed herein.

The valve device 656 can be disposed and operably situated within the opening 277 of the first vane device 164, wherein the opening, and the walls defining the opening, function as a valve housing for the valve device 656 (and any other corresponding components of the valve assembly). In this example, the valve device 656 comprises a movable valve component 657 coupled to a valve actuator 662, such as by one or more fasteners 651. The valve actuator 662 can comprise a piston 663 and an actuator device 665, such as a voice coil. The actuator device 665 can be electrically coupled to a power source and a controller (not shown) to electrically control the actuator device 665 to axially move the piston 663 along the axis of rotation 137 of the first vane device 164, for instance. Therefore, the valve actuator 662 is configured to axially move the movable valve component 657 between open, partially open, and closed positions.

The valve device 656 further comprises a first valve body 659 adjacent and in support of the movable valve component 657. The first valve body 659 comprises an outer annular channel 661, and a plurality of fluid openings 664 formed through the first valve body 659 radially around the outer annular channel 661. The first valve body 659 can comprise interface portions 668a and 668b on either side of the outer annular channel 661, which can each support seals 666 that function to seal off gasses, the interface portions 668a and 668b and the seals 666 being operable to engage and interface with the inner surface defining the opening 277 of the first vane device 164.

Figure 17A:
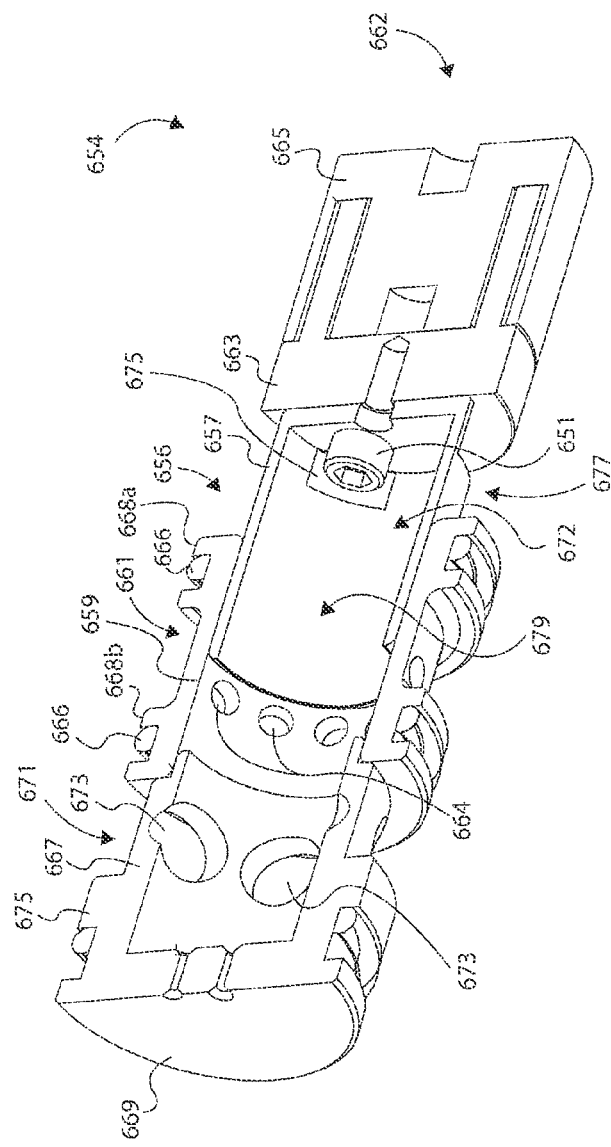
FIG. 17A is a cross sectional view of a valve assembly operable with the first vane device of FIG. 14A in accordance with an example of the present disclosure.
Figure 17B:
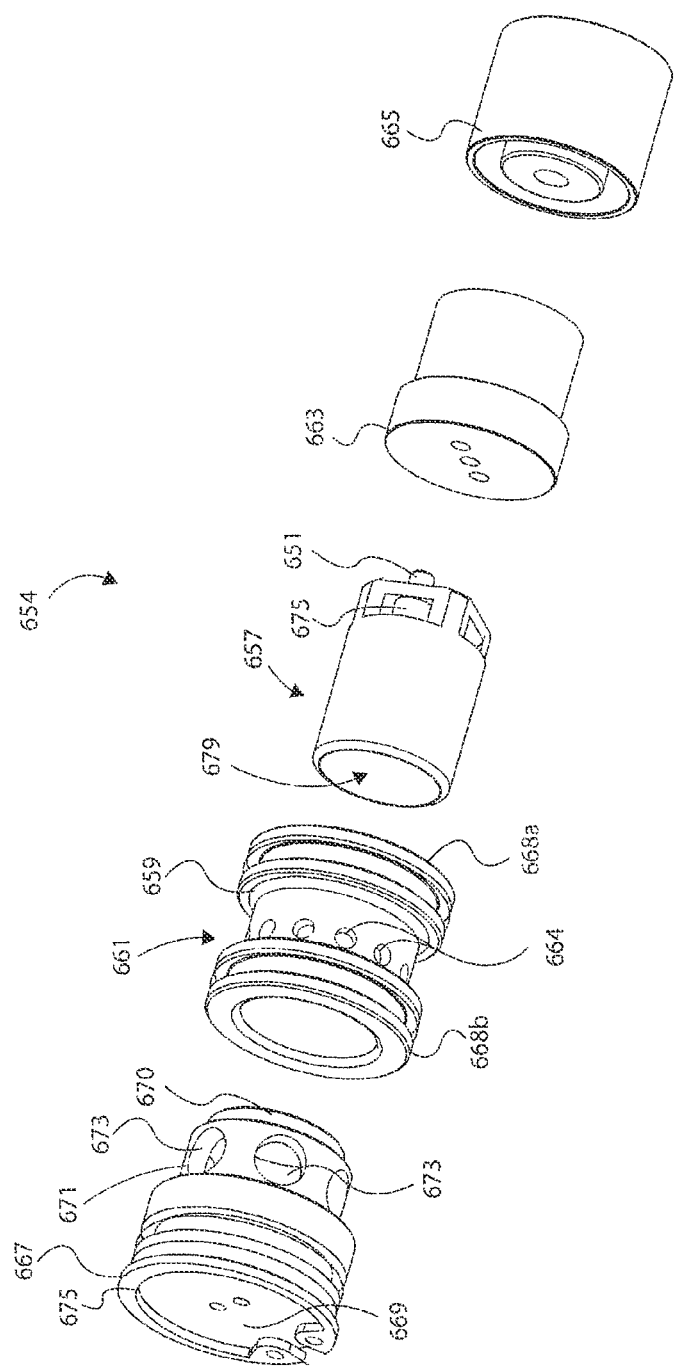
FIG. 17B is an exploded view of the valve assembly of FIG. 17A.
Figure 17C:
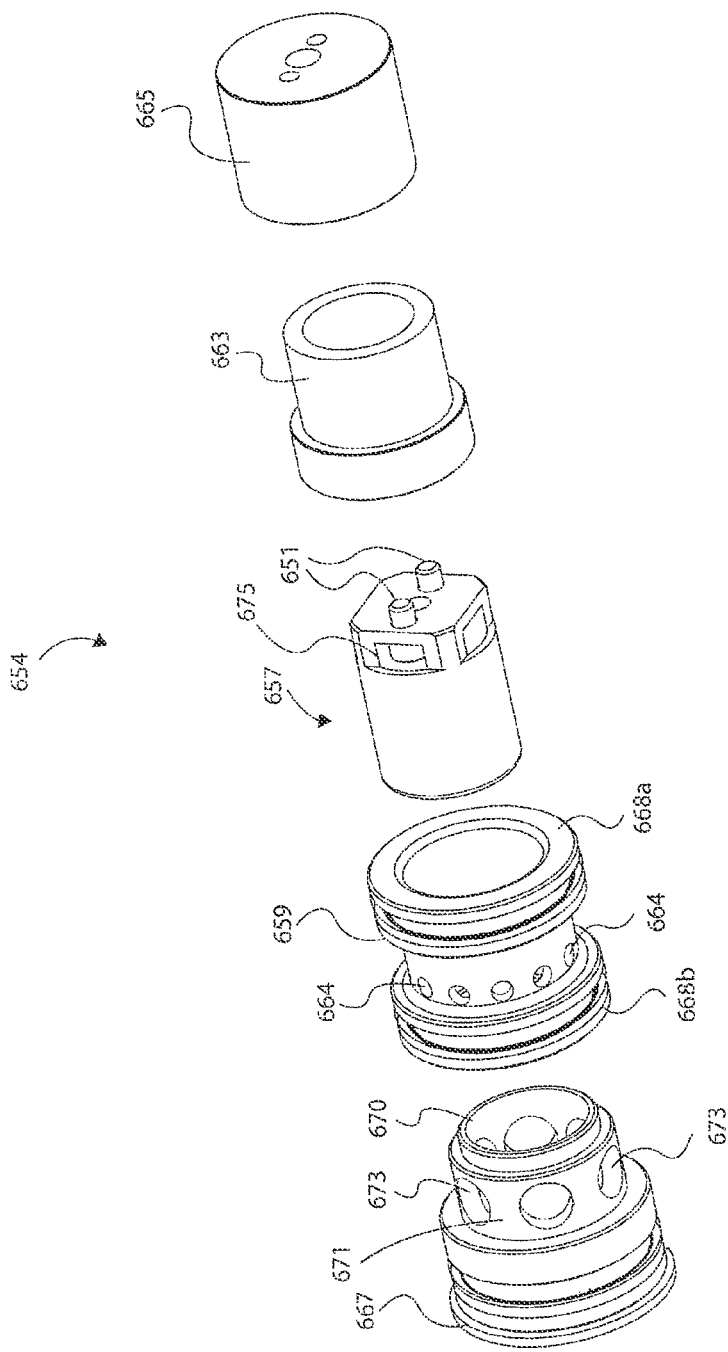
FIG. 17C is an exploded right view of the valve assembly of FIG. 17A.

The plurality of fluid openings 664 are each configured to be in fluid communication with the second channel 288b of the first vane device 164 (see FIG. 17D), which second channel 288b is in fluid communication with an expansion chamber via the conduit 290b, as discussed above. As shown in FIG. 17A, the first valve body 659 can be generally cylindrically shaped and can comprise a central opening 672 through which the movable valve component 657 translates axially, as discussed below.

The valve device 656 further comprises a second valve body 667 adjacent and engaged with the first valve body

659. The second valve body 667 can be formed generally as a cylindrically shaped cap member disposed within and interfaced with the opening 277 of the first vane device 164. At one end, the second valve body 667 can comprise an interface portion 670 that interfaces with or mates to the first valve body 659, and at the other end a cap portion 669 that seals off an inner chamber area 679 defined by the various components of the valve assembly 654. The second valve body 667 comprises an outer annular portion 671 that has a plurality of fluid openings 673 formed radially around the outer annular portion 671. The second valve body 667 can comprise an interface portion 675 adjacent the outer annular portion 671, which can help support a seal 677 to seal off gasses. The plurality of fluid openings 673 are each in fluid communication with the first channel 288a of the first vane device 164 (FIG. 17D), which is in fluid communication with a compression chamber via the conduit 290a, as discussed above.

Figure 17D:
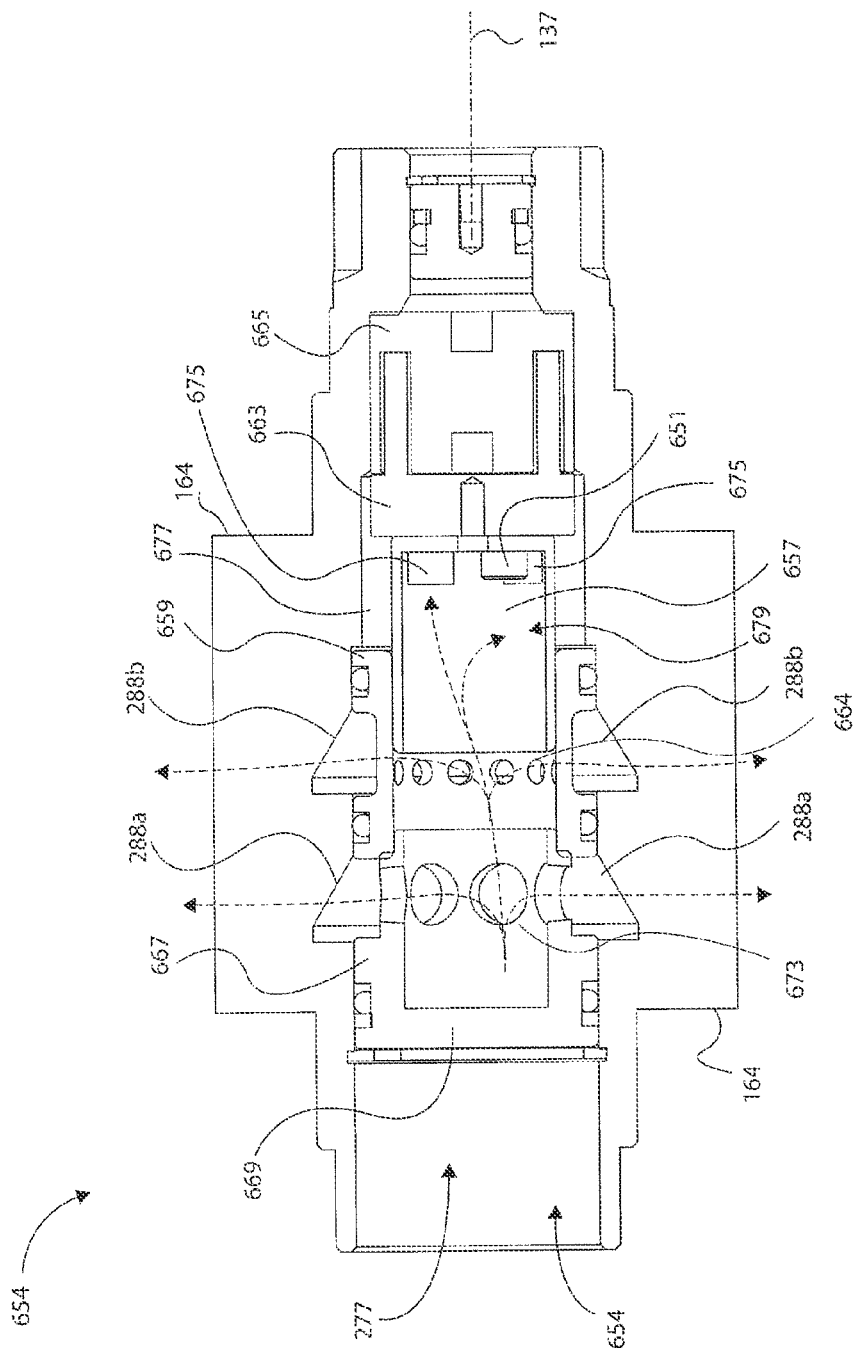
FIG. 17D is a cross-sectional view of the valve assembly, in an open position, of FIG. 17A.

As shown in FIGS. 17A and 17D, the valve device 656 is in the open position, specifically showing the movable valve component 657 retracted by the piston 663, which exposes or uncovers the plurality of openings 663 of the first valve body 659. Thus, the openings 664 are in fluid communication with the openings 673 of the second valve body 667 about chamber 679, which thereby places the conduits 290a and 290b in fluid communication with each other, which thereby places the compression and expansion chambers (e.g., 264a and 264b, FIG. 11A) in fluid communication with each other, thereby equalizing pressure between chambers of the quasi-passive elastic actuator when in the inelastic state, as discussed herein. Such open position can facilitate free swing mode of a robotic joint, for instance, as discussed above.

Figure 17E:
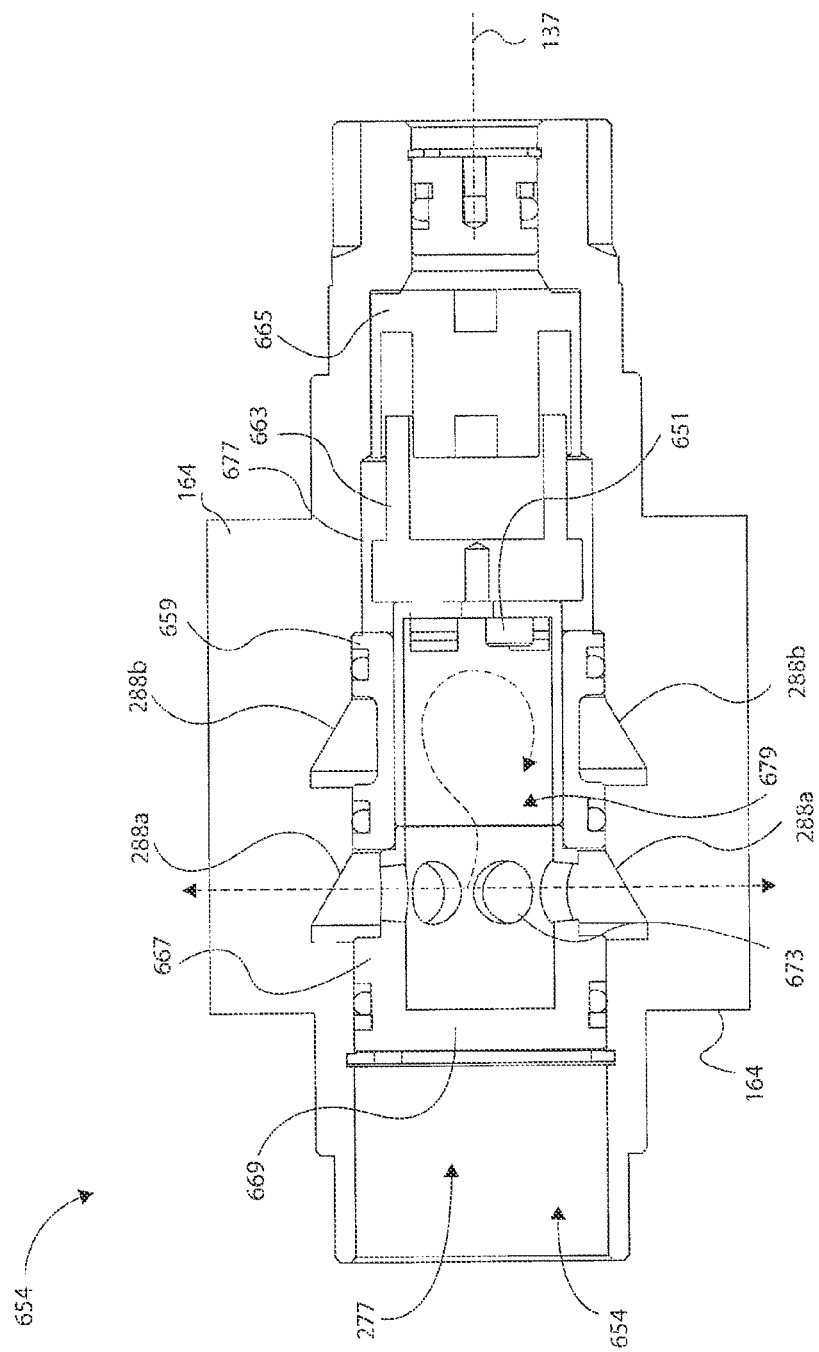
FIG. 17E is a cross-sectional view of the valve assembly, in a closed position, of FIG. 17A.

As shown in FIG. 17E, the valve device 656 is in the closed position, specifically showing the movable valve component 657 extended by the piston 663 (upon actuation), which blocks or covers the plurality of openings 664 of the first valve body 659. In this position, the openings 664 are not in fluid communication with the openings 673 of the second valve body 667, which thereby restricts fluid flow between the conduits 290a and 290b, which thereby restricts fluid flow between the compression and expansion chambers (e.g., 264a and 264b, FIG. 11A). The result is that the quasi-passive elastic actuator is placed in the elastic state to store energy or release energy, as discussed above. Although not shown, the valve device 656 can be positioned in the partially open position to place the quasi-passive actuator in the semi-elastic state.

Notably, the openings 664 and 673 are formed radially around the perimeters of the respective valve bodies 659 and 667. This configuration provides a radial balance of gas pressure about the first and second valve bodies 659 and 667, and also about the movable valve component 657, because an equal amount of gas pressure is passing through the openings 664 and 673 around the entire perimeter of the first and second valve bodies 659 and 667. This tends to result in equal or balanced gas pressure being exerted radially about the movable valve component 657, which reduces friction when the movable valve component 657 is actuated between the open and closed positions. Providing radial gas pressure balancing can reduce the amount of generated heat at a given speed at which the movable valve component 657 is actuated. In one example, the movable valve component 657 can switch between the open and closed positions in less than 15 milliseconds, or even less than 10 milliseconds. This is advantageous when it is desirable to quickly switch the quasi-passive elastic actuator between inelastic, semi-elastic, and elastic states, such as when a user is running while wearing an exoskeleton. This also maximizes or improves the efficiency of the quasi-passive elastic actuator because it reduces the likelihood that the quasi-passive elastic actuator is engaged or disengaged at an improper time that is counterproductive to the actual movement occurring about the joint of the robotic device.

In addition to the radial gas pressure balancing feature, the valve assembly 654 can also be axially gas pressure balanced. That is, the movable valve component 657 can comprise a cylindrically shaped tube body that has at least one fluid opening 675 in constant fluid communication with a first chamber 677 (shown adjacent the piston 663; FIG. 17D) and a second chamber 679, whether in the open or closed positions. That is, the at least one fluid opening 675 is formed through the movable valve component 657 adjacent the first chamber 677, which is defined by an inner surface of the first vane device 164. And, second chamber 679 is defined by in the inner surfaces along both of the movable valve component 657, the first valve body 659, and the second valve body 667. Thus, regardless of whether the valve assembly 654 is in the closed position, partially opened position, or the open position, there is continuous fluid communication between at least one fluid opening 675, the first chamber 677, and the second chamber 679, such that gas is not compressed or expanded about the first and second chambers 677 and 679 when switching between the open, partially open and closed positions. Thus, pressure is equalized between the first and second chambers 677 and 679 as the movable valve component 657 is axially moved between the open and closed positions, which equalization prevents gas pressure from being exerted against the movable valve component 657 in either axial direction (as discussed above) during switching the quasi-passive elastic actuator between inelastic and elastic states. Similar in principle to the radial gas pressure balancing discussed above, this axial gas pressure balancing tends to result in equal axial gas pressure being exerted about the valve assembly 654, which reduces friction when the movable valve component 657 is actuated between the open and closed positions, which reduces heat at a given speed at which the movable valve component 657 is actuated. This is advantageous when it is desirable to quickly switch a quasi-passive elastic actuator between inelastic and elastic states. This also maximizes or improves the efficiency of the quasi-passive elastic actuator because it reduces the likelihood that the quasi-passive elastic actuator is engaged and disengaged at an improper time that is counterproductive to the actual movement occurring about the joint of the robotic device.

With reference to FIGS. 18A-18D, illustrated is an example valve assembly operable with a first vane device in accordance with another example. In this example, a valve assembly 704 can comprise a valve device 706. The valve device 706 can comprise the same or similar features described above regarding valve device 606, and the valve device 706 can be incorporated into and operable with the first vane device 164 described above (see FIGS. 16A and 16B).

The valve device 706 can be disposed within the opening or bore 277 of the first vane device 164, along the axis of rotation 137 of the robotic joint. In this example, the valve device 706 can comprise a movable valve component 707 coupled to a valve actuator 712, such as by fasteners 705. A first valve body 709 can be coupled to the movable valve component 707, and the first valve body 709 can comprise a spool having an opening 703 that receives and facilitates the coupling of the movable valve component 707. The spool can comprise or can be made of a polytetrafluoroethylene (PTFE) material, or other similar material. Although not meant to be limiting in any way, the movable valve component 707 can be configured as a cylindrical tube with a flange mount, as shown, that is fastened to the valve actuator 712 via fasteners 705.

The valve actuator 712 can comprise a piston 713 and an actuator device 715, such as an arrangement with voice coils. The actuator device 715 can be electrically coupled to a power source and a controller (not shown) to electrically control the actuator device 715 to axially move the piston 713 along the axis of rotation 137, for instance. Therefore, the valve actuator 712 is configured to axially move the coupled movable valve component 707 and the first valve body 709 between the open, partially open, and closed positions (further described below regarding FIGS. 18C and 18D).

The valve device 706 can further comprise a second valve body 717 having a central opening 718 that slidable receives and supports the first valve body 709. The second valve body 717 comprises a first annular channel 711 having a plurality of first openings 723a formed through the second valve body 717 and disposed or positioned around the first annular channel 711. The plurality of first openings 723a are each in fluid communication with the second channel 288b of the first vane device 164 (see FIG. 18C), and the second channel 288b can be in fluid communication with an expansion chamber (e.g., such as expansion chamber 264b of FIGS. 11A and 11B) via the conduit 290b of the first vane device 164, as discussed above regarding FIGS. 14A and 14B.

The second valve body 717 comprises a second annular channel 719 having a plurality of second openings 723b formed through the second valve body 717 and disposed or positioned around the second annular channel 719. The second valve body 717 can comprise interface portions 725a-c adjacent and separating the respective annular channels 711 and 719, and that are configured to engage and to interface with the inner surface defining the opening 277 of the first vane device 164. Each interface portion 725a-c can further support one or more seals operable to seal off gasses between the first and second openings 723a and 723b. A cap member 735 can be coupled to an end of the second valve body 717 to seal off the inner chamber area of the valve assembly 706.

The plurality of second openings 723b are each in fluid communication with the first channel 288a of the first vane device 164 (see FIG. 18C), which is in fluid communication with a compression chamber (e.g., 264a) via the conduit 290a, as discussed above.

The first valve body 709 can comprise a first annular stop portion 727 and a second annular stop portion 729 formed on opposing sides of the structure defining the annular passageway 731. The annular passageway 731 can have curved surfaces that extend from respective stop portions 727 and 729 toward a neck portion. The annular passageway 731 can be configured to permit fluid flow between the first and second openings 723a and 723b (when in the open or partially open position) of the second valve body 717.

Figure 18A:
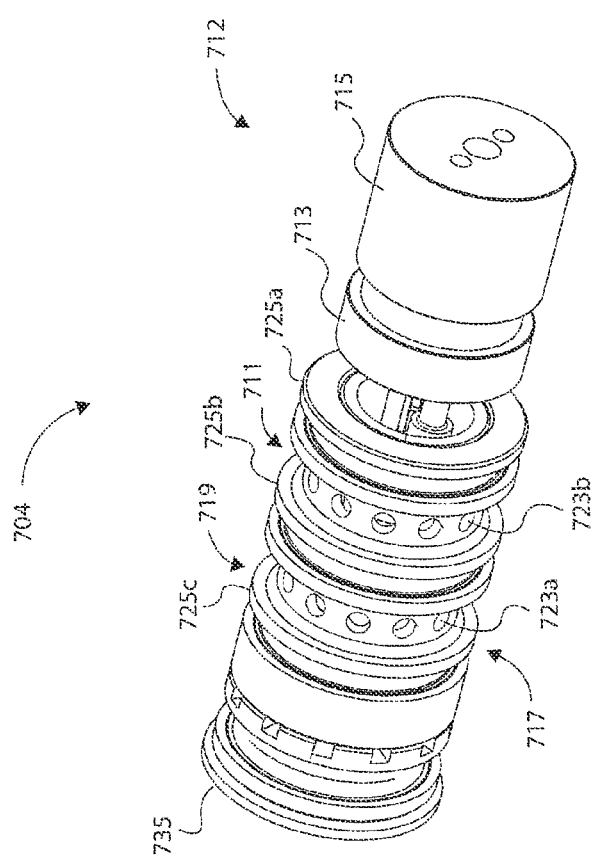
FIG. 18A is an isometric view of a valve assembly operable with the first vane device of FIG. 14A in accordance with an example of the present disclosure.
Figure 18B:
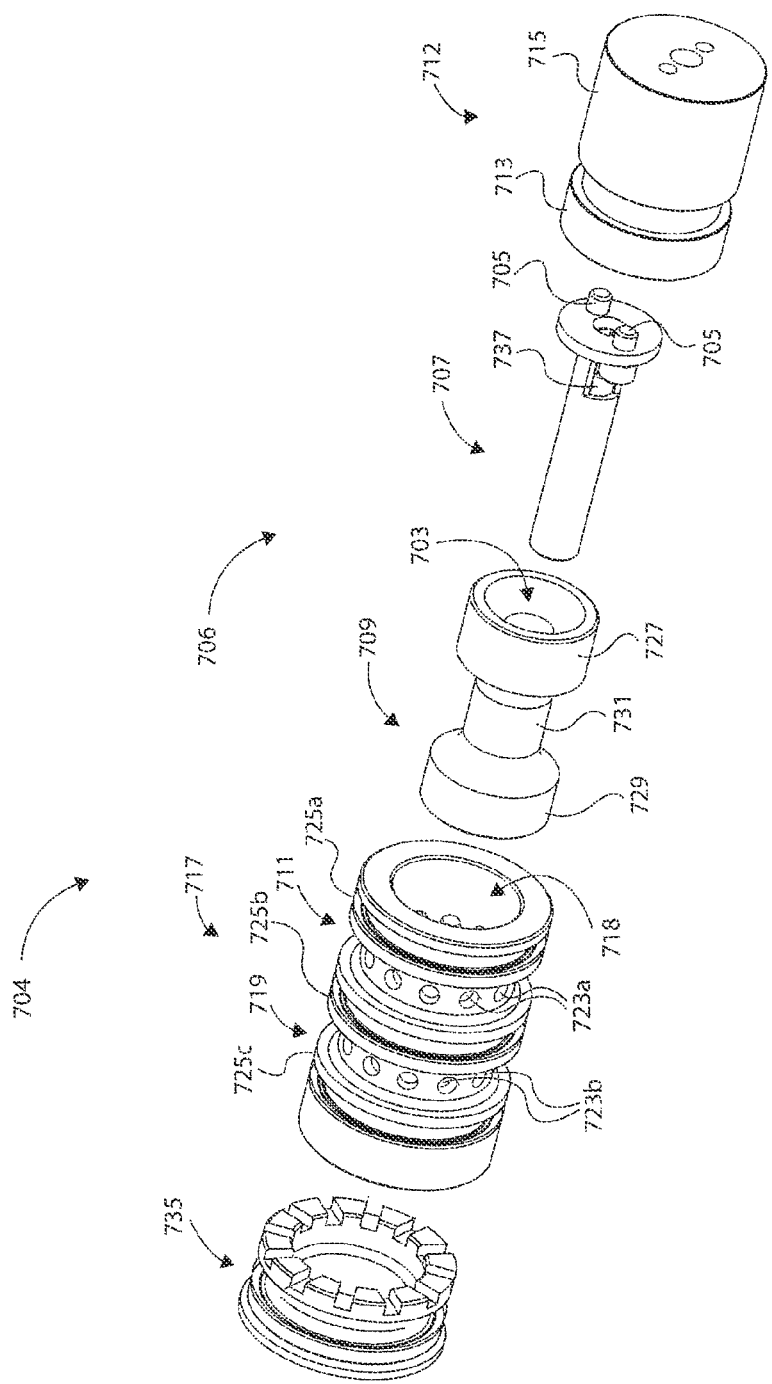
FIG. 18B is an exploded view of the valve assembly of FIG. 18A.
Figure 18C:
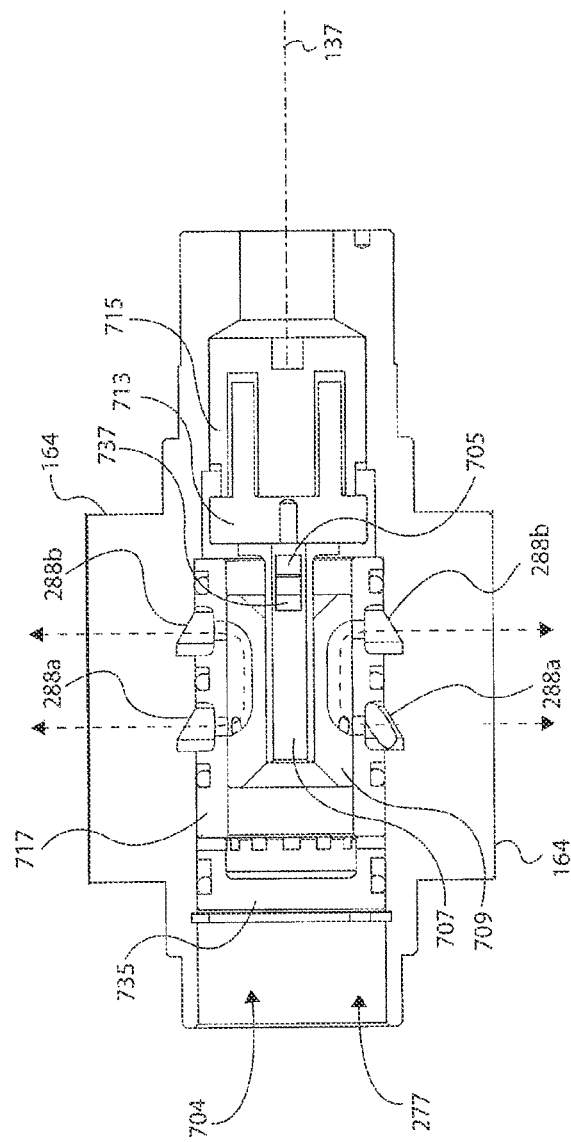
FIG. 18C is a cross-sectional view of the valve assembly, in an open position, of FIG. 18A.

FIG. 18C illustrates the valve device 706 in the open position, specifically showing the movable valve component 707 and the first valve body 709 as retracted by the piston 713, which exposes or uncovers the first and second openings 723a and 723b of the second valve body 717. Thus, the first and second openings 723a and 723b are in fluid communication with each other about the annular passageway 731 of the first valve body 709, which thereby places the conduits 290a and 290b (FIGS. 16A and 16B) in fluid communication, which thereby places the compression and expansion chambers (e.g., 264a and 264b) in fluid communication. In this open position, the quasi-passive elastic actuator is caused to enter the inelastic state, wherein pressures within the chambers of the quasi-passive elastic actuator are equalized, as discussed herein. Such open position can occur during free swing mode of a robotic joint, for instance.

Figure 18D:
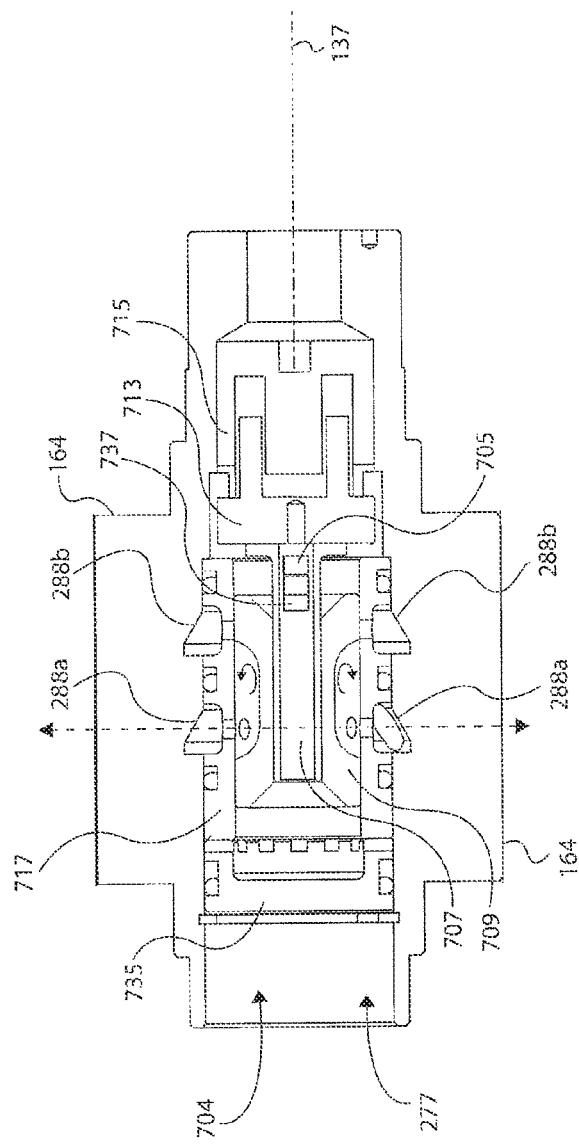
FIG. 18D is a cross-sectional view of the valve assembly, in a closed position, of FIG. 18A.

Conversely, FIG. 18D illustrates the valve device 706 in the closed position, specifically showing the movable valve component 707 and the first valve body 709 extended by the piston 713 (upon actuation), which position functions to block or cover the first openings 723a of the second valve body 717. In this position, the second openings 723b are not in fluid communication with the first openings 723a of the second valve body 717, thereby restricting fluid flow between the conduits 290a and 290b, which thereby restricts fluid flow between the compression and expansion chambers (e.g., 264a and 264b, FIG. 11A), such that the quasi-passive elastic actuator is caused to enter the elastic state to store or release energy (depending on the respective gait motion, for instance), as discussed above. Although not shown, the valve device 706 can be positioned in the partially open position to place the quasi-passive actuator in the semi-elastic state.

Notably, the first and second openings 723a and 723b are formed radially around the perimeter of the second valve body 717. This configuration provides a radial balance of gas pressure about the valve bodies 709 and 717 because an equal amount of gas pressure is entering the first and second openings 723a and 723b around the entire perimeter of the second valve body 717. And, because the first valve body 709 is formed symmetrical along the x plane and along the y plane (FIG. 18A), gas pressure is exerted and balanced radially around the entire perimeter annular passageway 731 (whether the valve is in the open, partially open or closed position). This tends to result in equal radial gas pressure being exerted to the first valve body 709 and the movable valve component 707, which reduces friction when the movable valve component 707 is actuated between the open and closed positions. Providing radial gas pressure balancing can reduce the amount of generated heat at a given speed at which the movable valve component 707 (and the first valve body 709) is actuated.

Furthermore, the valve assembly 704 can be axially gas pressure balanced. That is, the movable valve component 707 can comprise a cylindrically shaped tube body (see FIG. 18A) that has at least one fluid opening 737 in constant fluid communication with chambers on either side of the movable valve component 707, whether in the open, partially open or closed positions (similar in function as the axially balanced principle discussed regarding FIGS. 17A-17E). That is, pressure is equalized axially as the movable valve component 707 is moved between the open and closed positions, which prevents gas pressure from being exerted against the movable valve component 707 in the axial directions during switching the quasi-passive elastic actuator between inelastic and elastic states. As with the radial gas pressure balancing discussed above, this axial balancing tends to result in equal axial gas pressure being exerted about the valve assembly 706, which reduces friction when the movable valve component 707 is actuated between the open, partially open and closed positions, and which reduces heat at a given speed at which the movable valve component 707 is actuated.

FIGS. 19A-19D illustrate a valve assembly operable with a first vane device in accordance with another example. In this example, a valve assembly 700 can comprise a valve device 702 disposed and operably situated within an opening or bore 740 of a first vane device 764 (FIG. 19C), which can be configured to be similar to the first vane device described above. In one non-limiting example, the valve assembly 700 can be operable with the first vane device 764, such that the first vane device 764 can comprise or makeup a portion of the valve assembly 700, such as a housing for the valve device 702. In one example, the valve assembly 700 can be situated about an axis of rotation 708 of the first vane device 764, such that the axis of rotation 708 extends through at least some of the structural elements making up the valve assembly 700. Said another way, the valve device 702 can have at least a portion of its structural elements that intersect, or operate about, the axis of rotation 708.

The valve assembly 700 can comprise a valve actuator 742, such as an electric actuator, operatively coupled to the valve device 702 to facilitate selective actuation of the valve device 702. The valve device 702 can comprise a movable valve component 714 and a support frame 716. The support frame 716 can be coupled to a housing of the valve actuator 742 via one or more fasteners 718. A rotatable shaft 720 of the valve actuator 742 extends through an aperture 722 of the support frame 716 and is coupled to the movable valve component 714 via at least one fastener 724. The rotatable shaft 720 can be rotatable by an electric motor of the valve actuator 742 to rotate the movable valve component 714 about the axis of rotation 708 and between open, partially open, and closed positions.

The movable valve component 714 can comprise a radial band member 726 and a central drive shaft 728. The radial band member 726 can be a thin sheet of material (e.g., metal) formed in an S-shape along the axis of rotation 708, and a central portion of the radial band member 726 can be coupled to the central drive shaft 728. In one example, the radial band member 726 can be received through an elongated slot of the central drive shaft 728, and secured therein. A bearing cap 730 can be coupled to an end of the central drive shaft 728 that rotatably couples the movable valve component 714 to the support frame 716, and for sealing gas about the valve assembly 700. A first curved stop surface 732a of the radial band member 726 wraps around, and is rotatably/slidably interfaced to, a first support member 734a of the support frame 716. Likewise, a second curved stop surface 732b of the radial band member 726 wraps around, and is slidably interfaced to, a second support member 734b of the support frame 716.

Figure 19A:
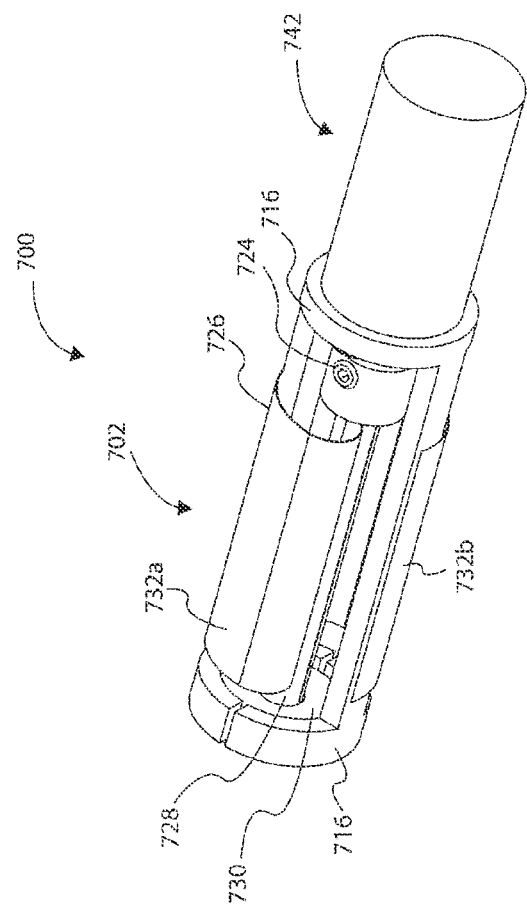
FIG. 19A is an isometric view of a valve assembly usable with a first vane device.
Figure 19B:
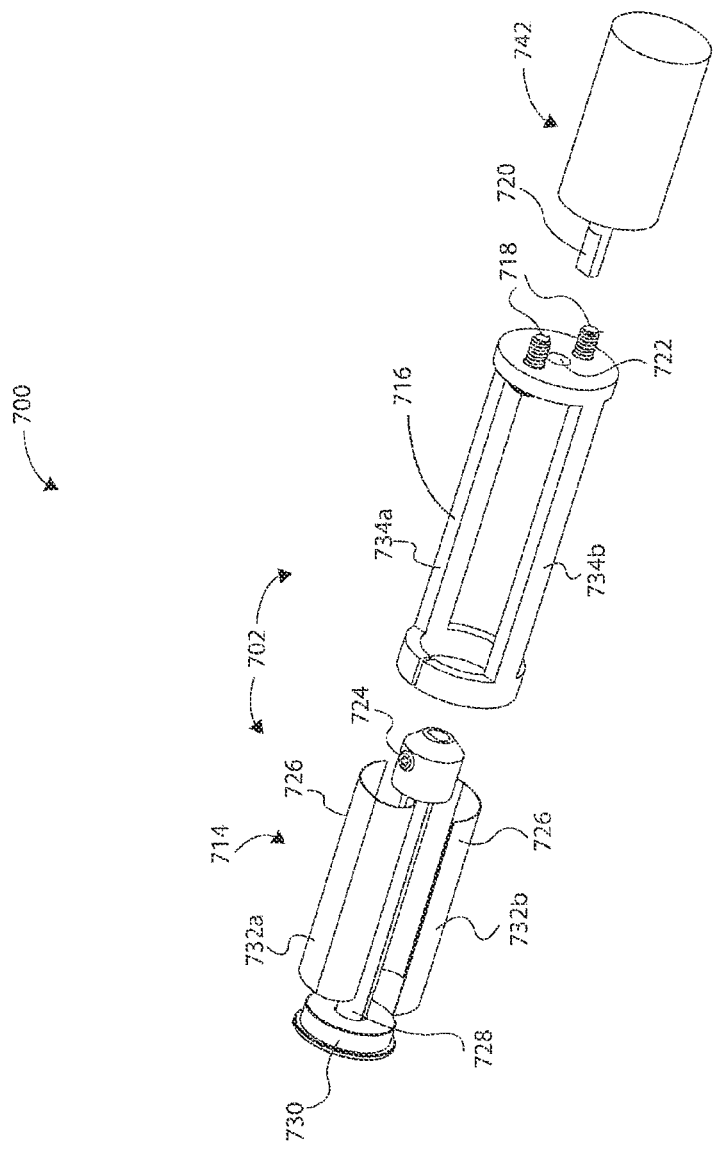
FIG. 19B is an exploded view of the valve assembly of FIG. 19A.
Figure 19C:
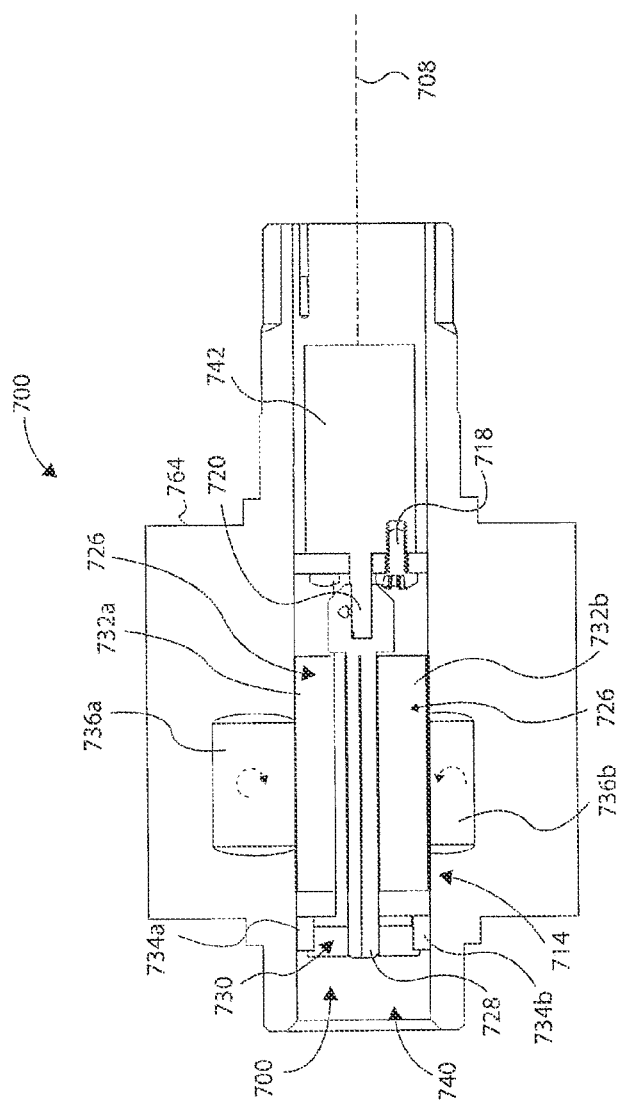
FIG. 19C is a cross sectional view of the valve assembly, in a closed position, of FIG. 19A.
Figure 19D:
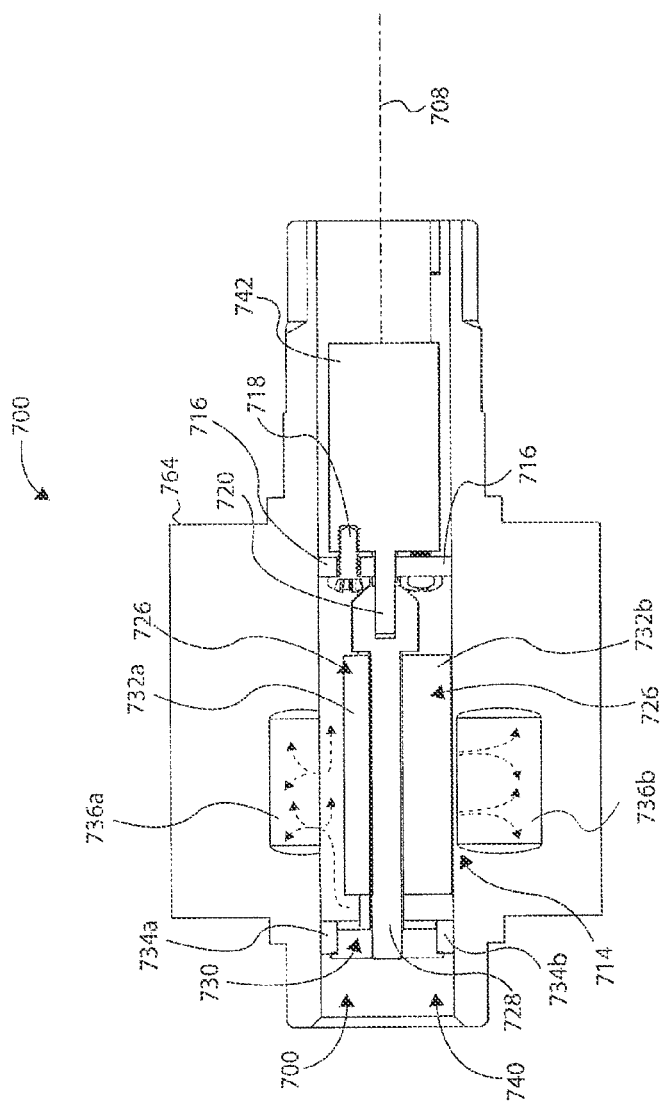
FIG. 19D is the cross sectional view of the valve assembly, in an open position, of FIG. 19C.

With particular reference to FIG. 19C (closed position) and FIG. 19D (open position), the valve assembly 700 can be disposed through the opening 740 of a first vane device 764. The opening 740 can be defined by one or more walls or surfaces of the first vane device 764. The first vane device 764 can comprise a first conduit 736a in fluid communication with a compression chamber (e.g., 610a of FIG. 15B) of the first vane device 764, and a second conduit 736b in fluid communication with an expansion chamber of the first vane device 764 (e.g., 610b of FIG. 15B). Note that only a section of each of the first and second conduits 736a and 736b are shown (and as slots), because they can traverse at an angle through the first vane device 764, so it should be appreciated that the first and second conduits 736a and 736b can be configured similarly as described above with reference to FIGS. 15A-15C. As shown in FIG. 19C, upon receiving a control signal (e.g., from a controller), the valve actuator 742 can actuate/rotate the movable valve component 714, to cause rotation of the central drive shaft 728 and the radial band device 726 to the closed position, such that the first curved stop surface 732a blocks or covers the first conduit 736a to restrict airflow, and such that the second curved stop surface 732b blocks or covers the second conduit 736b to restrict airflow. In this manner, a shunt circuit is closed that restricts airflow between the compression and expansion chambers (e.g., 610a and 610b) about the valve assembly 700.

Upon receiving a valve control signal (e.g., from a controller), the valve actuator 742 can actuate/rotate the movable valve component 714 counter clockwise (see FIG. 19A) to the open position shown in FIG. 19D, or the partially open position. As a result, the first and second curved stop surfaces 732a and 732b move to uncover or expose the respective conduits 736a and 736b, which opens or partially opens the shunt circuit that permits fluid flow around/about the radial band device 726, and therefore between the compression and expansion chambers (e.g., 610a and 610b), as illustrated by the airflow arrows of FIG. 19D.

Thus, when the valve device 714 is in the closed position of FIG. 19C, the quasi-passive elastic actuator (having the first vane device 764 and the valve assembly 700) operates in the elastic state because the shunt circuit restricts airflow between compression and expansion chambers about the valve assembly 700, such that the quasi-passive elastic actuator can either store energy or release energy, as discussed herein. Conversely, when the valve device 702 is in the open position, thereby opening the shunt circuit, gas pressure can be equalized between compression and expansion chambers so that the quasi-passive elastic actuator does not store or release energy; rather, it is in free swing mode where the first vane device 764 (e.g., 600 of FIG. 15B) is freely rotatable relative to the second vane device (e.g., 603). In this manner, negligible resistance exists between the first vane device and the second vane device (and consequently first and second robotic support members rotatably coupled to the quasi-passive elastic actuator, as exemplified above). With the valve device 702 in the partially opened position, with the shunt circuit partially opened, the quasi-passive actuator can operate in the semi-elastic state to generate and apply a braking force.

Notably, the valve device 702 provides radial and axial gas pressure balancing when in the closed and open and partially open positions. The valve device 702 is axially gas pressure balanced because it rotates about the axis of rotation 708, and when in the open, partially open and closed positions, gas freely flows axially along the radial band device 726. The valve device 702 is radially gas pressure balanced because, when in the closed position, an equal amount of radial gas pressure is exerted to each of the first and second curved stop portions 732a and 732b, because they are formed opposite each other so that an equal amount of pressure is exerted inwardly via the first and second conduits 736a and 736b.

Providing both the radial and axial gas pressure balancing can reduce the amount of generated heat due to friction at a given speed at which the movable valve component 657 is actuated. This is advantageous when it is desirable to quickly switch a quasi-passive elastic actuator between inelastic and elastic states. This also maximizes or improves the efficiency of the quasi-passive elastic actuator because it reduces the likelihood that the quasi-passive elastic actuator is engaged, partially engaged or disengaged at an improper time that is counterproductive to the actual movement occurring about the joint of the robotic device. The radial band device 726 is also relatively lightweight because it is a thin sheet of metal, for instance, and therefore it actuates relatively quickly, and with very little friction.

Figure 20A:
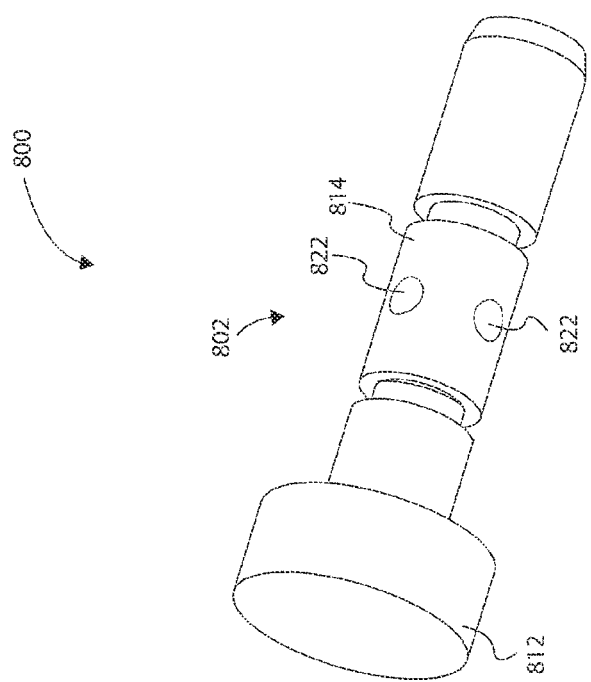
FIG. 20A is an isometric view of a valve assembly usable with a first vane device.
Figure 20B:
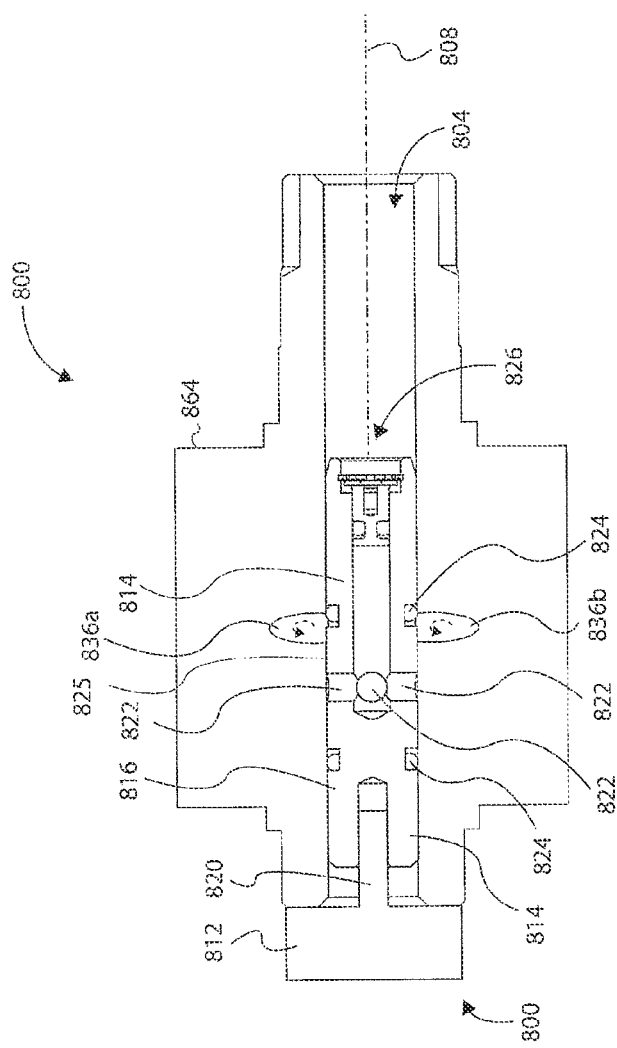
FIG. 20B is a cross sectional view of the valve assembly, in a closed position, of FIG. 20A.
Figure 20C:
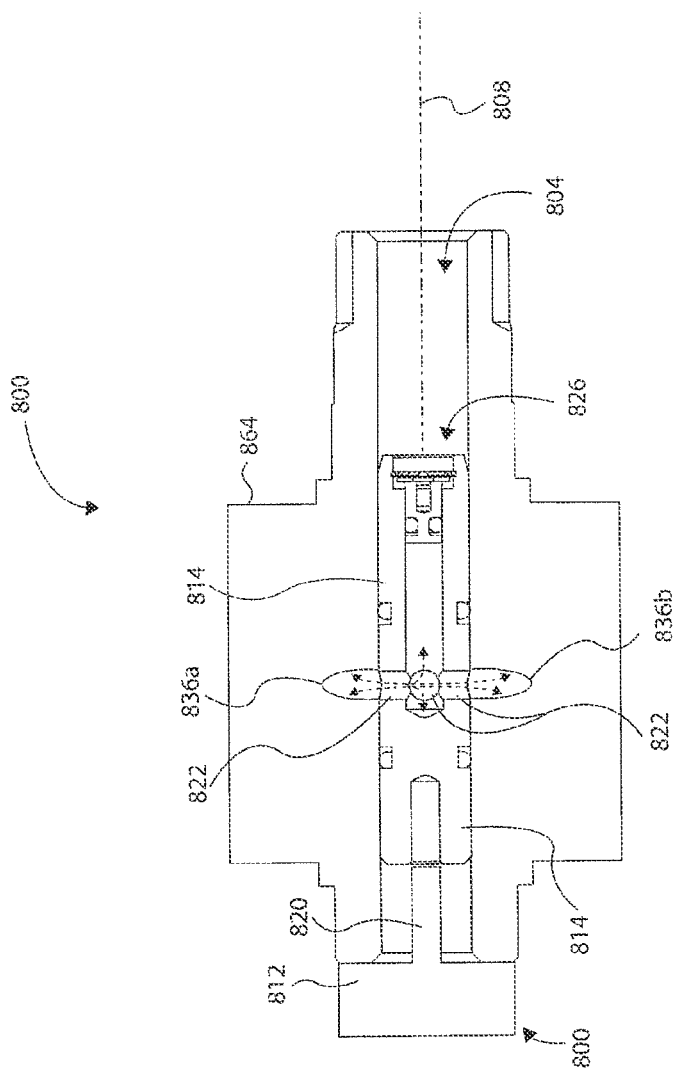
FIG. 20C is the cross sectional view of the valve assembly, in an open position, of FIG. 20B.

FIGS. 20A-20C illustrate a valve assembly operable with a first vane device in accordance with another example. In this example, a valve assembly 800 can comprise a valve device 802 disposed and operably situated within an opening or bore 804 of a first vane device 864 (FIGS. 20B and 20C), which can be configured to be similar to the first vane device described above. In one example, the valve device 802 can be situated about an axis of rotation 808 of the first vane device 864, such that the axis of rotation 808 extends through at least some of the structural elements making up the valve assembly 800. Said another way, the valve device 802 can have at least a portion of its structural elements that intersect, or operate about, the axis of rotation 808. The first vane device 864 can comprise a portion of the valve assembly 800.

The valve assembly 800 can comprise a valve actuator 812, such as an electric actuator, operatively coupled to the valve device 802 to facilitate selective actuation of the valve device 802 (upon receiving a valve control signal). The valve device 802 can comprise a movable valve component 814 that can be translated axially along the axis of rotation 808. The valve actuator 812 can comprise an electric motor coupled to a shaft 820 configured to axially move (i.e., push or pull) the movable valve component 814 within the opening 804. The valve actuator 812 can be a voice coil or other device configured to axially move the movable valve component 814 about the opening 804.

The movable valve component 814 can comprise an elongated cylindrical body having a plurality of through holes 822 formed through the body. In the example shown, there are two through holes 822 formed offset from one another vertically through the movable valve component 814, thereby providing four radially formed openings spaced around the movable valve component 814. In one aspect, the openings can be equally spaced apart from one another. Annular seals 824 (FIG. 20B) can be disposed on either side of the through holes 822 and around the movable valve component 814 in recessed portions to seal gas about the valve device 802 (FIG. 20B). A cap seal 826 can be coupled to an end of the elongated cylindrical body 816 to seal gas within the valve device 802 (FIG. 20B).

With particular reference to FIG. 20B (closed position) and FIG. 20C (open position), the valve assembly 800 can be disposed through the opening 804 of the first vane device 864, such that the valve is located and functions about the rotational joint of the joint module in which it operates. The first vane device 864 can comprise a first conduit 836a in fluid communication with a compression chamber of the first vane device 864 (e.g., 610a of FIG. 15B), and a second conduit 836b in fluid communication with an expansion chamber of the first vane device 864 (e.g., 610b of FIG. 15B). Thus, as shown in FIG. 20B, upon receiving a valve control signal (e.g., from a controller), the valve actuator 812 can actuate the movable valve component 814 to the closed position, whereby an outer cylindrical surface 825 of the elongated cylindrical body 816 blocks or covers the first conduit 836a and the second conduit 836b to close a shunt circuit that restricts airflow between the compression and expansion chambers about the valve assembly 800.

Upon receiving a valve control signal (e.g., from a controller), the valve actuator 812 can actuate/translate the movable valve component 814 to the open position shown in FIG. 20C, or a partially opened position. As a result, the through holes 822 are then caused to be aligned with, and in fluid communication with, the conduits 836a and 836b, which opens or partially opens the shunt circuit that permits fluid flow between the compression and expansion chambers (e.g., 610a and 610b) about the valve assembly 800, as illustrated by the airflow arrows of FIG. 20C. Note that only a section of the conduits 836a and 836b are shown because they traverse at an angle through the first vane device 864, but it will be appreciated that the conduits 836a and 836b can be formed and can function similarly as described above regarding 15A-15C.

Thus, in the closed position of FIG. 20B, a particular quasi-passive elastic actuator (incorporating the first vane device 864 and valve assembly 800) operates in the elastic state because the shunt circuit restricts airflow between compression and expansion chambers about the valve assembly 800, such that the quasi-passive elastic actuator can store energy and release energy, as discussed herein. Conversely, when the valve device 802 is in the open position and the shunt circuit is open, gas pressure is equalized between the compression and expansion chambers so that the quasi-passive elastic actuator cannot store or release energy, rather, it is in free swing mode where the first vane device 864 (e.g., 600 of FIG. 15B) is freely rotatable relative to a second vane device (e.g., 603). In this manner, negligible resistance exists between the first vane device and the second vane device (and consequently first and second robotic support members rotatably coupled about the quasi-passive elastic actuator, as exemplified above). When the valve device 802 is in the partially opened position, with the shunt circuit partially opened, the quasi-passive actuator can operate in the semi-elastic state to generate and apply a braking force.

Notably, the valve device 802 provides radial gas pressure balancing because, when in the closed position for instance, an equal amount of gas pressure is exerted radially to the outer surface 825 of the movable valve component 814 adjacent the conduits 836a and 836b due to the orientation of the holes 822. And when in the open or partially open position, the perpendicularly offset formed through holes 822 facilitate equalized radial gas pressure about the inside of the movable valve component 814 because they are formed in four different, equally separated directions (e.g., 90 degrees relative to each other). This radial gas pressure balancing can reduce generated heat due to friction when the movable valve component 814 is actuated between the open and closed positions at a given speed at which the movable valve component 814 is actuated. This is advantageous when it is desirable to quickly switch a quasi-passive elastic actuator between inelastic and elastic states. This also maximizes or improves the efficiency of the quasi-passive elastic actuator because it reduces the likelihood that the quasi-passive elastic actuator is engaged or disengaged at an improper time that is counterproductive to the actual movement occurring about the joint of the robotic device.

FIGS. 21A-21E illustrate a valve assembly operable with a first vane device in accordance with another example. In this example, a valve assembly 900 can comprise a valve device 902 disposed and operably situated within an opening or bore 904 of a first vane device 864 (FIGS. 21C-21E), which can be configured to be similar to the first vane device described above. In one example, the valve device 902 can be situated about an axis of rotation 908 of the first vane device 964, such that the axis of rotation 908 extends through at least some of the structural elements making up the valve assembly 900. Said another way, the valve device 902 can have at least a portion of its structural elements that intersect, or operate about, the axis of rotation 908. In one example, the first vane device 964 can comprise a portion of the valve assembly 900.

The valve assembly 900 can comprise a valve actuator 912, such as an electric actuator, operatively coupled to the valve device 902 to facilitate selective actuation of the valve device 902. The valve device 902 can comprise a movable valve component 914 rotatable about the axis of rotation 908. The valve actuator 912 is shown generically as a box, but it can be an electric motor actuator operable to rotate the movable valve component 914, as discussed herein, or other types of actuators capable of actuating the valve.

The movable valve component 914 can comprise an elongated cylindrical body having a plurality of first openings 922a and a plurality of second openings 922b, in fluid communication with each other via a central conduit 924 (FIGS. 21B-21E). Each of the first and second openings 922a and 922b can be formed at approximately 90 degrees relative to one another, thereby providing openings radially formed and equally spaced around the movable valve component 914.

A valve body 926, comprising a central opening 928, rotatably receives and supports the movable valve component 914, and comprises a plurality of third openings 922c formed radially around the valve body 926 within an annular recess 923 of the valve body 926. The third openings 922c can be formed at corresponding positions relative to the first openings 922a of the movable valve component 914. A rear bearing seal device 930a rotatably supports the movable valve component 914 via a first pin 932a coupled to the movable valve component 914, and a front bearing seal device 930b rotatably supports a second pin 932b of the movable valve component 914.

Figure 21A:
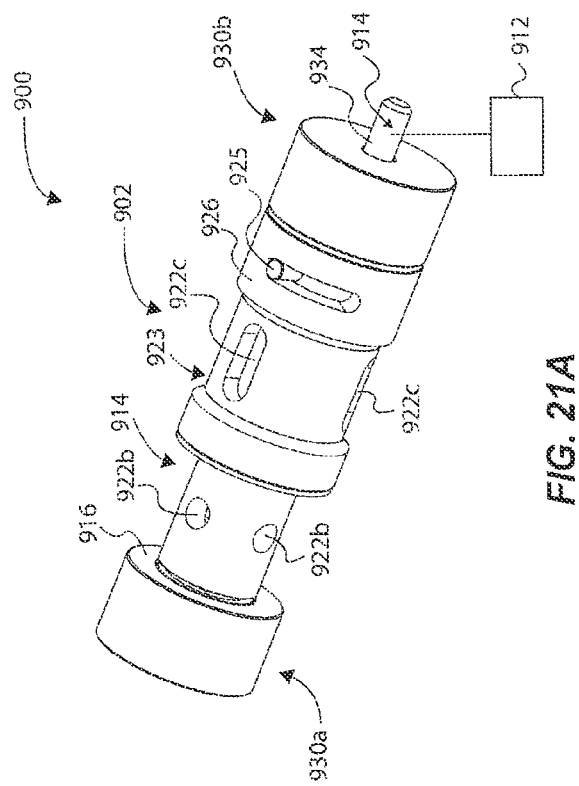
FIG. 21A is an isometric view of a valve assembly usable with a first vane device.
Figure 21B:
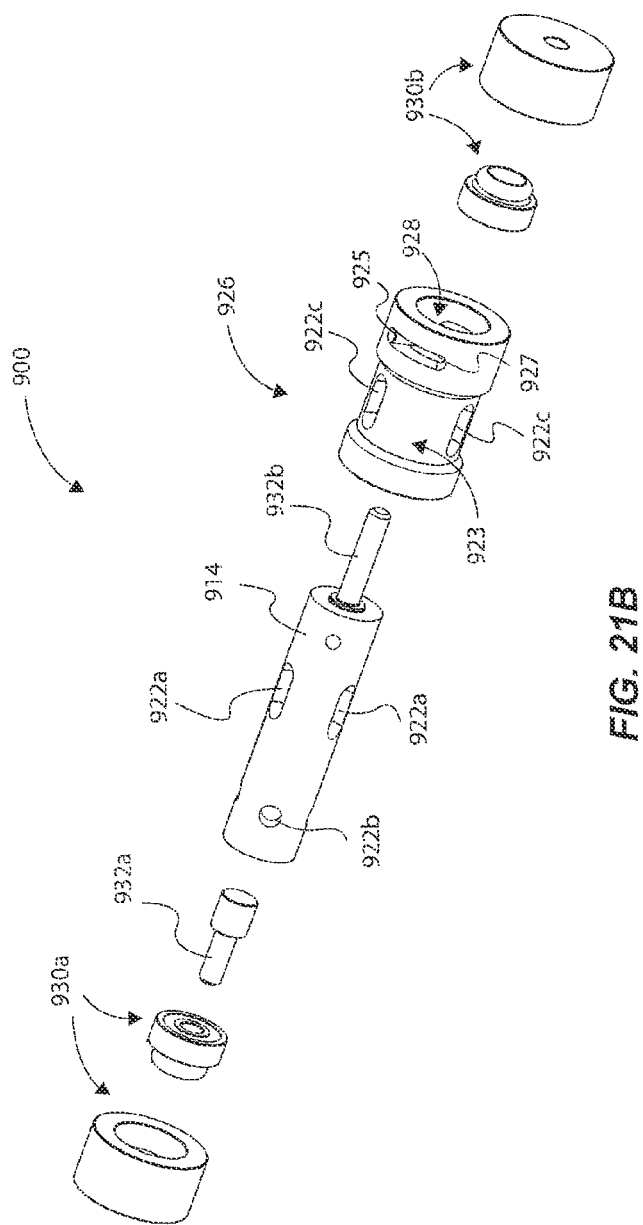
FIG. 21B is an exploded view of the valve assembly of FIG. 21A.
Figure 21C:
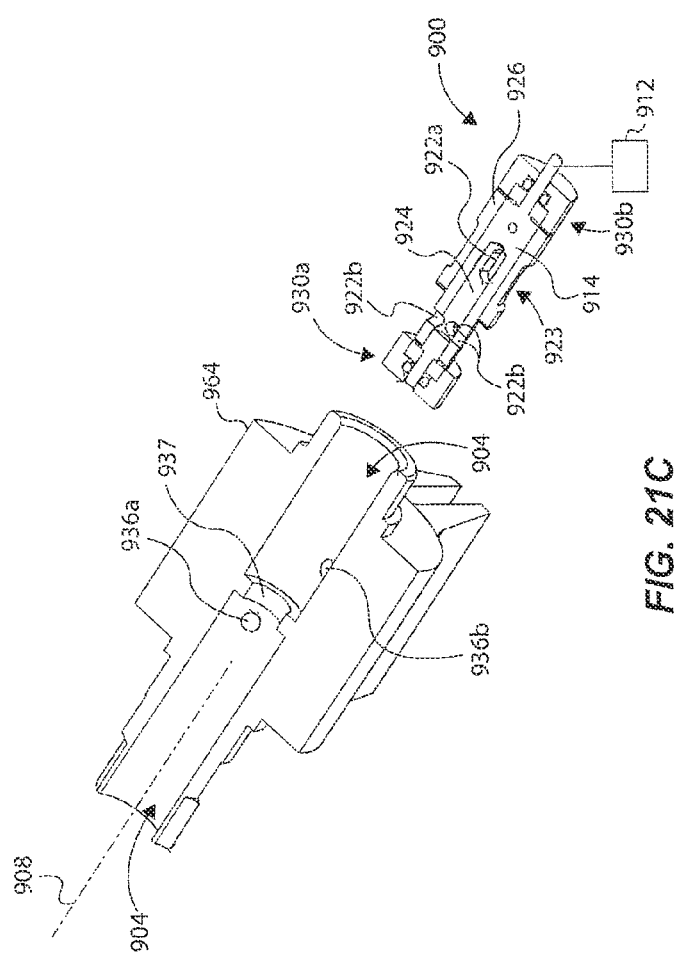
FIG. 21C is a cross sectional view of the valve assembly, in a closed position, of FIG. 21A and a first vane device.

With reference to FIG. 21C, the valve assembly 900 can be disposed through the opening 904 of the first vane device 964. The first vane device 964 can comprise a first conduit 936a in fluid communication with a compression chamber (e.g., 610a of FIG. 15B), and a second conduit 936b in fluid communication with an expansion chamber (e.g., 610b of FIG. 15B). A partition wall 937 can be formed annularly around the inside of the opening 904, which provides a stop for the valve body 926 to abut against, and thereby also functioning as a gas seal between conduits 936a and 936b. Thus, a portion of the movable valve component 914 is rotatably interfaced to the partition wall 937, as further discussed below.

Figure 21D:
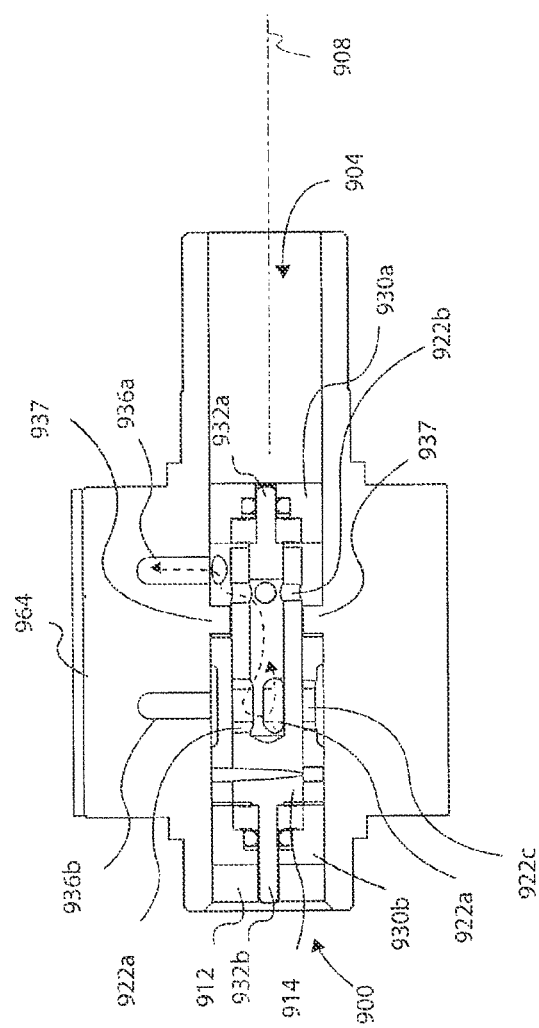
FIG. 21D is a cross sectional view of the valve assembly, in a closed position, of FIG. 21C.
Figure 21E:
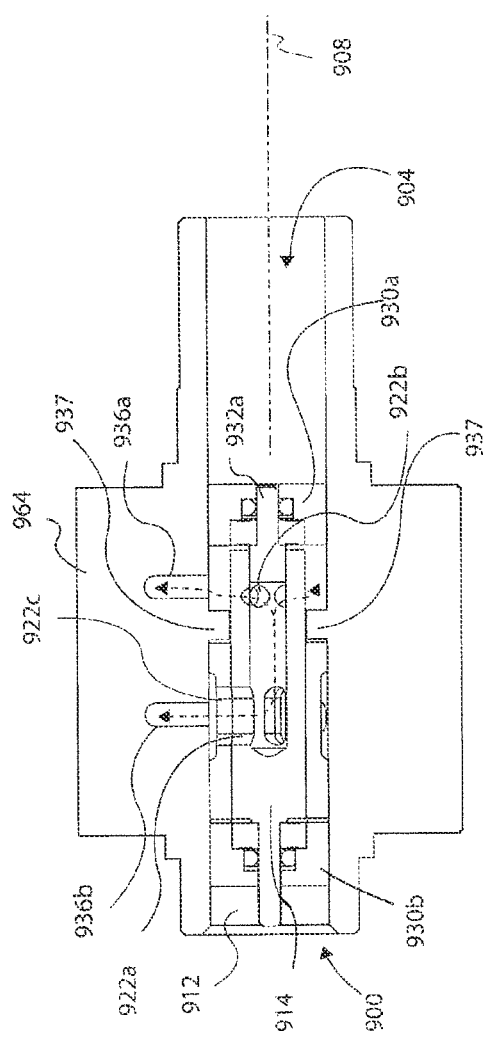
FIG. 21E is a cross sectional view of the valve assembly, in an open position, of FIG. 21D.

With particular reference to FIG. 21D, the valve actuator 912 can be operated to actuate/rotate the movable valve component 914 to the closed position (upon receiving a valve control signal), such that the first openings 922a are not aligned with the third openings 922c, thereby closing a shunt circuit that restricts airflow between the conduits 936a and 936b about the valve assembly 900. Upon receiving a valve control signal, the valve actuator 912 can actuate/rotate the movable valve component 914 to the open position of FIG. 20E, or a partially open position. As a result, the first openings 922a are aligned with the third openings 922c, which thereby opens the shunt circuit that allows airflow about the central conduit 924, and among all of the first, second, and third openings 922a-c. Opening the shunt circuit in this manner places conduits 936a and 936b in fluid communication with each other, which permits fluid flow between the compression and expansion chambers (e.g., 610a and 610b) about the valve assembly 900, as illustrated by the airflow arrows in FIG. 20E. Note that only a section of the conduits 936a and 936b are shown because they traverse at an angle through the first vane device 964, but it will be appreciated that the conduits 936a and 936b can be formed and function similarly as described regarding 15A-15C. A stop pin 925 (FIGS. 21A and 21B) can be coupled to the movable valve component 914 and slidably interfaced to a slot 927 of the valve body 926 to restrict rotational movement of the movable valve component 914 between the open and closed positions.

Thus, in the closed position of FIG. 20D, the quasi-passive elastic actuator (incorporating the first vane device 964 and the valve assembly 900) operates in the elastic state when the shunt circuit is closed because airflow is restricted between compression and expansion chambers, such that the quasi-passive elastic actuator can either store or release energy, as discussed herein. Conversely, when the valve device 902 is in the open position and the shunt circuit is opened, gas pressure is equalized between compression and expansion chambers, such that the quasi-passive elastic actuator cannot store or release energy; rather, it is in free swing mode where the first vane device 964 (e.g., 600 of FIG. 15B) is freely rotatable relative to the second vane device (e.g., 603). In this manner, negligible resistance exists between the first vane device and the second vane device (and consequently first and second robotic support members rotatably coupled about the quasi-passive elastic actuator, as exemplified above). When the valve device 902 is in the partially opened position, with the shunt circuit partially opened, the quasi-passive actuator can operate in the semi-elastic state to generate and apply a braking force.

Notably, the valve device 902 provides radial gas pressure balancing because, when in the closed position for instance, an equal amount of gas pressure is radially exerted against outer surfaces of the movable valve component 914 adjacent the second conduit 936b. And when in the open or partially open position, the equally spaced apart first, second, and third openings 922a-c (individual sets of openings) facilitate equal radial pressure about the inside and/or outside of the movable valve component 914 in four different, equally spaced directions due to the orientation of the each set of openings 922a-c having respective openings that are equally spaced from each other approximately 90 degrees relative to adjacent openings.

The valve device 902 is also axially gas pressure balanced when in the open or partially open position because gas is permitted to flow axially along the central conduit 924 between the set of first and second openings 922a and 922b. This radial and axial gas pressure balancing can reduce generated heat due to friction when the movable valve component 914 is actuated between the open and closed positions. This is advantageous when it is desirable to quickly switch a quasi-passive elastic actuator between inelastic and elastic states, such as when a user is running while wearing an exoskeleton. This also maximizes or improves the efficiency of the quasi-passive elastic actuator because it reduces the likelihood that the quasi-passive elastic actuator is engaged or disengaged at an improper time that is counterproductive to the actual movement occurring about the joint of the robotic device.

Figure 22A:
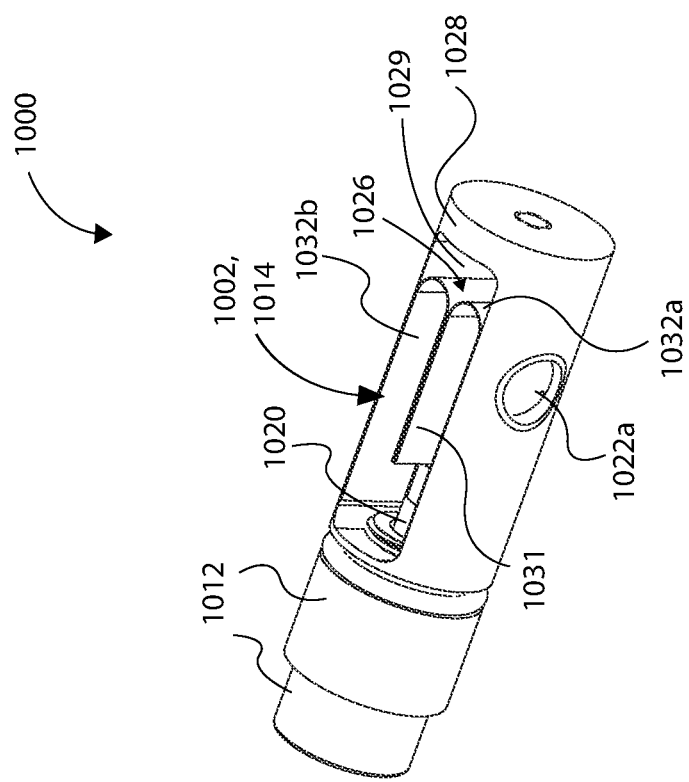
FIG. 22A is an isometric view of a valve assembly usable with a first vane device.
Figure 22B:
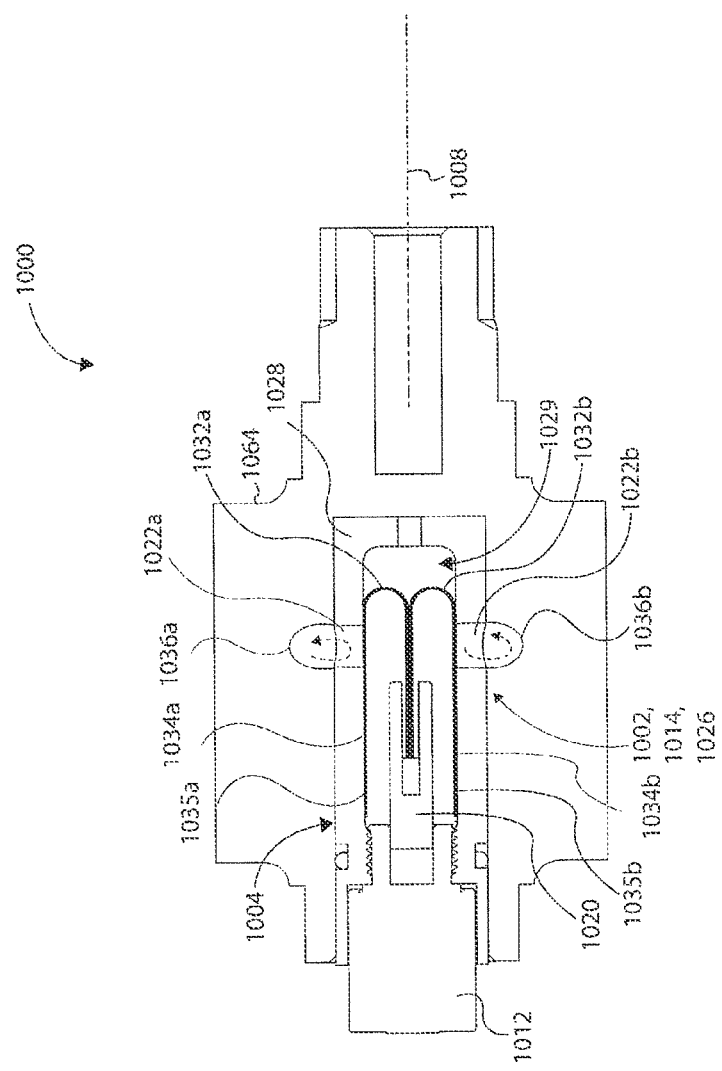
FIG. 22B is a cross sectional view of the valve assembly, in a closed position, of FIG. 22A.
Figure 22C:
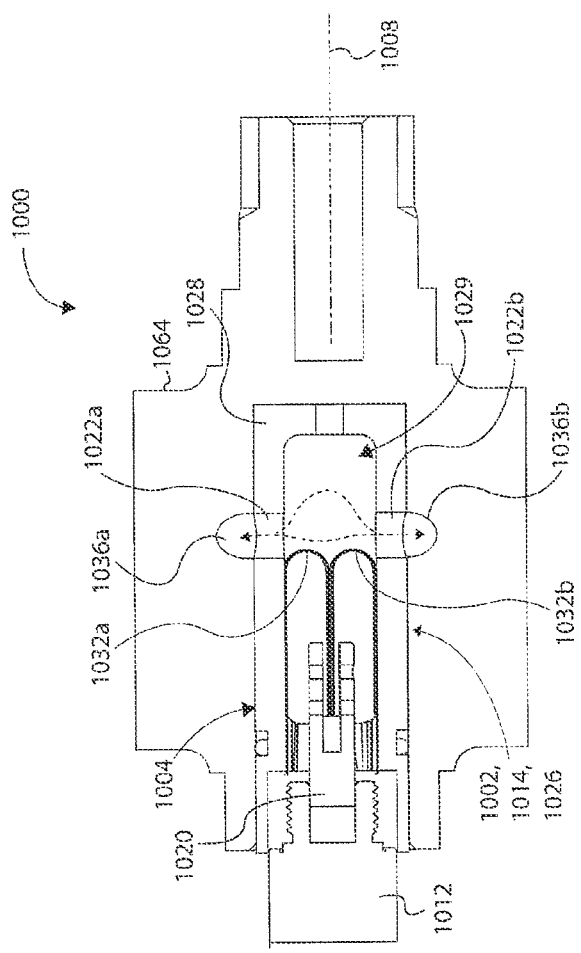
FIG. 22C is the cross sectional view of the valve assembly, in an open position, of FIG. 22B.

FIGS. 22A-22C illustrate a valve assembly operable with a first vane device in accordance with another example. In this example, a valve assembly 1000 can comprise a valve device 1002 disposed and operably situated within an opening 1004 of a first vane device 1064 (FIG. 22B), which can be configured to be similar to the first vane device described above. In one example, the valve assembly 1000 can be situated about an axis of rotation 1008 of the first vane device 1064, such that the axis of rotation 1008 extends through at least some of the structural elements making up the valve assembly 1000. Said another way, the valve assembly 1000 can have at least a portion of its structural elements that intersect, or operate about, the axis of rotation

1008. In one example, the first vane device 1064 can comprise a portion of the valve assembly 1000, namely the first vane device 1064 can comprise a housing for the valve device 1002.

The valve assembly 1000 can comprise a valve actuator 1012, such as an electric actuator, operatively coupled to the valve device 1002 to facilitate selective actuation of the valve device 1002. The valve device 1002 can comprise a movable valve component 1014. A translatable shaft 1020 of the valve actuator 1012 can be coupled to the movable valve component 1014 for translational movement of the movable valve component 1014 axially along the axis of rotation 1008. The movable valve component 1014 can comprise a band device 1026 coupled to the movable shaft 1020. The band device 1026 can have first and second band sections 1032a and 1032b, which can be comprised of a thin material (e.g., a thin metal sheet) each formed into a U-shape. Ends 1031 of respective band sections 1032a and 1032b can be biased together and coupled to the movable shaft 1020, thus forming respective moveable sections of the band device 1026. The other opposite ends of the respective band sections 1032a and 1032b can comprise first and second stop portions 1034a and 1034b formed as planar sheet portions. The first and second stop portions 1034a and 1034b can extend along and be slidably interfaced to corresponding surfaces 1035a and 1035b of a valve cartridge 1028.

The valve cartridge 1028 can also define a portion of the valve device 1002, and can have a generally cylindrical shape about its outer surface area that interfaces with the inner surface of the opening 1004 of the first vane device 1064 (FIG. 22B). The valve cartridge 1028 can have a slot 1029 that slidably supports and receives the band device 1026, and that seals gas within the valve device 1000.

With particular reference to FIG. 22B (closed position) and FIG. 22C (open position), the first vane device 1064 can comprise a first conduit 1036a in fluid communication with a compression chamber (e.g., 610a of FIG. 15B), and a second conduit 1036b in fluid communication with an expansion chamber (e.g., 610b of FIG. 15B). The valve cartridge 1028 can be positioned in the opening 1004 of the first vane device 1064 such that a first opening 1022a of the valve cartridge 1028 is aligned and in fluid communication with the first conduit 1036a, and such that a second opening 1022b of the valve cartridge 1028 is aligned and in fluid communication with the second conduit 1036b. Thus, when in the closed position of FIG. 22B, the first and second stop portions 1034a and 1034b of the respective band sections 1032a and 1032b cover the respective first and second openings 1022a and 1022b, thereby restricting airflow between the first and second conduits 1036a and 1036b. This position closes a shunt circuit that restricts airflow between the compression and expansion chambers of the first vane device 1064 about the valve device 1000.

As shown in FIG. 22C, the valve actuator 1012 can actuate/translate the movable valve component 1014 to the open position, upon receiving a valve control signal, by translating the movable valve component 1014 along the axis of rotation 1008, thereby moving the band sections 1032a and 1032b. This uncovers or exposes the respective openings 1022a and 1022b, such that the shunt circuit is open that permits airflow between the first and second conduits 1036a and 1036b, and therefore between the compression and expansion chambers (e.g., 610a and 610b), as illustrated by the airflow arrows of FIG. 22C. Each opening 1022a and 1022b can have a screen device operable therewith to equalize gas pressure on the band device 1026.

Thus, in the closed position of FIG. 22B, the particular quasi-passive elastic actuator (incorporating the rotary band device 1064 and the valve assembly 1000) operates in the elastic state when the shunt circuit is closed because airflow is restricted between compression and expansion chambers, such that the quasi-passive elastic actuator can either store energy or release energy, as discussed herein. Conversely, when the valve device 1014 is in the open position and the shunt circuit is open, gas pressure is equalized between compression and expansion chambers such that the quasi-passive elastic actuator cannot store or release energy; rather, it is in free swing mode where the first vane device 1064 (e.g., 600 of FIG. 15B) is freely rotatable relative to the second vane device (e.g., 603). In this manner, negligible resistance exists between the first vane device and the second vane device (and consequently first and second support members rotatably coupled about the quasi-passive elastic actuator, as exemplified above). When the valve device 1014 is in the partially opened position, with the shunt circuit partially opened, the quasi-passive actuator can operate in the semi-elastic state to generate and apply a braking force.

Notably, the valve device 1002 is radially gas pressure balanced because, when in the closed position for instance, and equal amount of radial gas pressure is exerted to the outer side of each of the first and second planar stop portions 1034a and 1034b of respective first and second band sections 1032a and 1032b because they are disposed opposite one another. Providing radial gas pressure balancing provides similar benefits discussed herein regarding the other valve assemblies.

Figure 23:
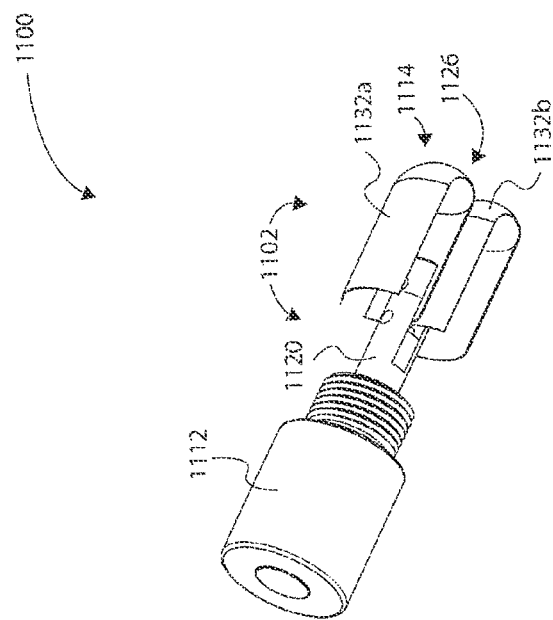
FIG. 23 is an isometric view of a valve assembly usable with a first vane device.

FIG. 23 shows a valve assembly 1100 operable with a first vane device in accordance with another example of the present disclosure. The valve assembly 1100 is a variation of the valve assembly 1000 discussed above, so it will not be discussed or shown in great detail. However, in this example the valve assembly 1100 can comprise a valve device 1102 disposed and operably situated within an opening (e.g., 1004, FIG. 22B) of a first vane device (e.g., 1064, FIG. 22B), and can be situated about an axis of rotation (e.g., 1008) of the first vane device, similarly as discussed with reference to FIG. 22A-C, but without the valve cartridge 1028.

The valve assembly 1100 can comprise a valve actuator 1112, such as an electric actuator, operatively coupled to the valve device 1102 to facilitate selective actuation of the valve device 1102. The valve device 1102 can comprise a movable valve component 1114, such as the combination of a movable shaft 1120 and a band device 1126. The band device 1126 can be coupled to the movable shaft 1120 such that rotation of the movable shaft 1120 causes rotation of the band device 1126. The band device 1126 can comprise first and second radial band sections 1132a and 1132b, which can be comprised of a thin flexible material (e.g., metal sheet) each formed in a U-shape and having curved surfaces formed inwardly (as opposed to the planar surfaces of radial band device 1026 discussed above). Outer ends of the respective radial band section 1132a and 1132b are each configured to slidably/rotatably interface to corresponding inner curved surfaces of a first vane device (e.g., 1064). Thus, upon receiving a valve control signal, the actuator 1112 rotates the movable valve component 1120, which rotates the band device 1126 from a closed position to an open position, for instance, which exposes or uncovers conduits (e.g., 1036a and 1036b) of the first vane device (e.g., 1064). The open position opens a shunt circuit that permits airflow between expansion and compression chambers about the valve assembly 1100 of a quasi-passive elastic actuator. And the closed position closes a shunt circuit that restricts airflow between expansion and compression chambers about the valve assembly 1100. It should be appreciated that the valve assembly 1100 can have similar advantages and functionality as described regarding the valve assembly of FIGS. 22A-22C. When the band device 1126 is in the partially opened position, with the shunt circuit partially opened, the quasi-passive actuator can operate in the semi-elastic state to generate and apply a braking force.

Figure 24:
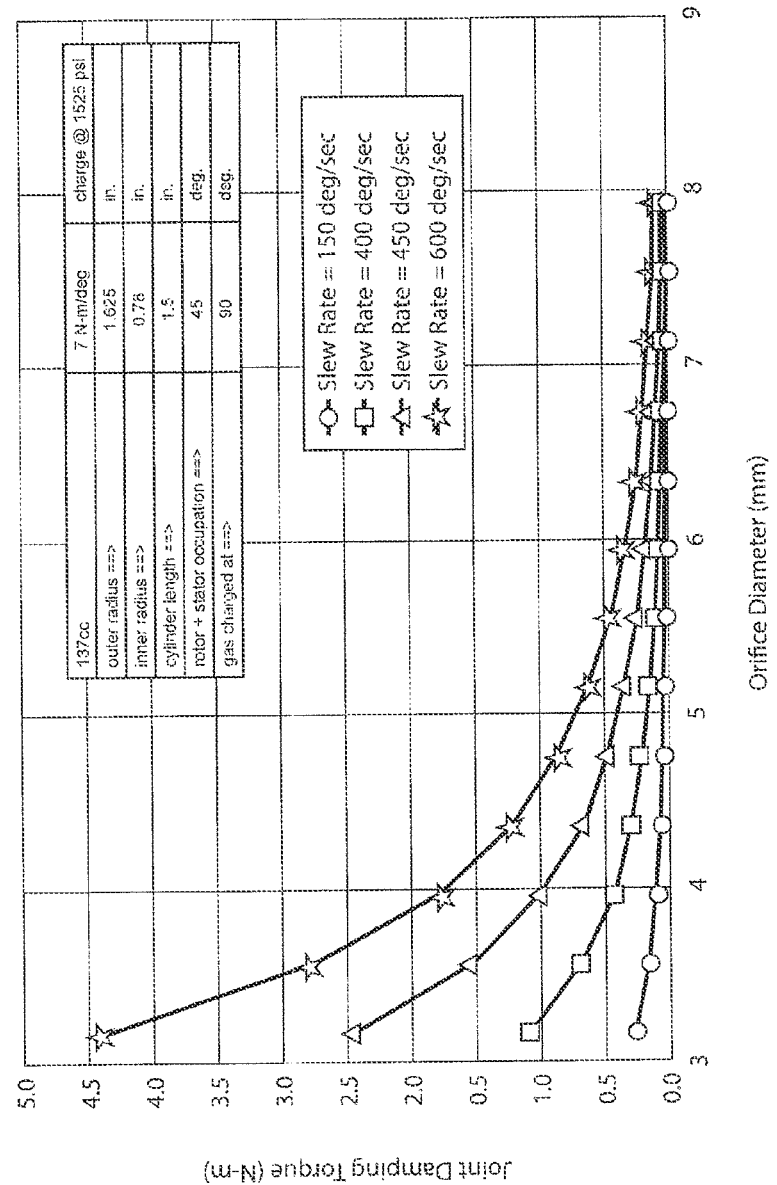
FIG. 24 is a graph illustrating performance values for joint damping torque vs. various rotary vane conduit sizes.

FIG. 24 is a graph illustrating performance values for joint damping torque vs. various rotary conduit sizes for a quasi-passive elastic actuator corresponding to a knee joint in accordance with an example of the present disclosure. More specifically, in some examples the opening of conduits (e.g., 290a and 290b) of a particular first vane device (e.g., 164) can be selected to comprise a particular size to facilitate a damping of a quasi-passive elastic actuator, as exemplified above. That is, by selecting a diameter of the conduits to be in the range of 5-6 mm, for instance, the gas pressure difference between the expansion and compression chambers will result in a joint damping torque of less than approximately 1 N-m, as illustrated, even at the maximum estimated joint speed. This graph pertains to a nominal charge pressure of 1,525 psi in the compression and expansion chambers of the quasi-passive elastic actuator (e.g., having 137 cc), and for a tunable actuator joint module having a torque of 7 N-m/deg. In this example, the outer radius of the quasi-passive elastic actuator is 1.625 in., and the inner radius (defined by the compression and expansion chambers) is 0.78 in., and the cylinder length is 1.5 in. (as defined by the compression and expansion chambers). The first vane device and the second vane device have a volume occupation of 45 deg., and the gas in the compression and expansion chambers is charged at a 90 deg. position of the first vane device relative to the second vane device Various slew rates are represented on the graph of FIG. 19 as corresponding to the rotational movement (deg.) of the joint per second. As can be appreciated by the graph, depending on the slew rate, as the conduit diameter increases, the joint damping torque (N-m) decreases. Therefore, a conduit diameter of about 3 mm will provide a greater joint damping torque than one that is 6 mm, for instance. This can be advantageous when designing differing joints, such as a knee joint module as compared to a hip joint module, because inherently lower or higher damping toques would be generated by the selection of the size of the conduit diameter.

Note that spring stiffness is a function of piston/vane and chamber geometries, as well as gas pressure charge. Thus, the magnitude of stiffness for a given joint module is adjustable for mission-specific payloads and terrain-specific gaits while the active valve controls exactly when that stiffness is engaged for energy recovery during the support phase (elastic state) and when it is disengaged during the free swinging state (inelastic state). For instance, the compression and expansion chambers can be selected to comprise a particular volume along with the density of the gas, while the conduits through the first vane device can be selected to corresponding sizes that do not unduly restrict gas flow when in the inelastic state. Also, the particular joint location is determinative of the magnitude of the selected stiffness value. For instance, the charge pressure for a knee joint and the joint speed would both be significantly larger than required from a hip joint.

The tunable actuator joint modules discussed herein can be controlled by a controller of a computer system, whether located on-board of the robot or robotic device or remotely located such that the robot or robotic device is in communication with the computer system using known communication techniques and methods. In addition, the controller can be used to control each of the tunable joint actuator modules in a robot or robotic device, and to operate these in a coordinated manner (e.g., within a robotic exoskeleton, operate a tunable actuator knee joint module with that of a tunable actuator hip module or tunable actuator ankle module, such that each of these functions with the other to provide human kinematic equivalent motions, such as during walking, running, squatting, or other movements). For example, assume a lower body exoskeleton is worn by a human operator during a running gait cycle, and assume left/right ankle joints each include the tunable actuator joint module 800, and left/right knee and hip joints each include a tunable actuator joint module (109a, 130, or 500), discussed in detail above. The computer system can receive position and force data from position or force sensors, or both, associated with each of said tunable actuator joint modules. The position and force data can be processed to generate information that determines the particular respective positions of each of said tunable actuator joint modules, or the forces acting thereon, and one or more gait recognition algorithms can process such information to determine which (if any) of said tunable actuator joint modules are to switch between elastic and inelastic states. Accordingly, the computer system can generate and transmit command signals to respective tunable actuator joint module(s) to actuate the respective valve assemblies to the appropriate open or closed positions, and/or to actuate respective electric motors to apply a primary torque. Such processing can be performed in milliseconds and on a continuous basis during the gait cycle, for instance, for every tunable actuator joint module. The same holds true for task-specific movements, such as walking, jumping, squatting, climbing or other movements.

It is further noted that rotation of the joints (i.e., relative rotation between the input and output members) defined by the various tunable actuator joint modules discussed herein can be in any direction (e.g., the same direction, different directions) during the storing and releasing of the energy, during the generation and application of a braking force, as well as the opening of the valve assemblies and the shunt circuits to facilitate free swing of the joints. In other words, the valve assemblies can be operated to engage to store energy, to release energy, or to disengage to facilitate free swing of the joint upon rotation of an associated joint in the same direction or in various different directions. This is the case for all of the examples set forth in the present disclosure.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

Although the disclosure may not expressly disclose that some embodiments or features described herein may be combined with other embodiments or features described herein, this disclosure should be read to describe any such combinations that would be practicable by one of ordinary skill in the art. The user of "or" in this disclosure should be understood to mean non-exclusive or, i.e., "and/or," unless otherwise indicated herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the foregoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A robotic system for a robotic limb configured to recover energy for minimizing power consumption of the robotic system, comprising:
   a first support member;
   a second support member; and
   a quasi-passive elastic actuator rotatably coupling the first and second support members to define a joint of the robotic system rotatable about an axis of rotation defining a degree of freedom, the quasi-passive elastic actuator comprising:
      a housing coupled to the first support member;
      a first vane device supported by the housing and coupled to the second support member;
      a second vane device coupled to the housing and interfaced with the first vane device, the first vane device and second vane device being rotatable relative to each other within the housing and defining, at least in part, a compression chamber and an expansion chamber;
      a valve assembly located and operable at the joint of the robotic system, the valve assembly comprising a valve device disposed through an opening of the first vane device along the axis of rotation; and
      a shunt circuit facilitating fluid flow between the compression and expansion chambers through the valve assembly,
   wherein the valve assembly is operable to position the valve device in an open position to open the shunt circuit to permit fluid flow between the compression and expansion chambers, thereby placing the quasi-passive elastic actuator in an inelastic state, and
   wherein the valve assembly is operable to position the valve device in a closed position to close the shunt circuit to restrict fluid flow between the compression and expansion chambers, thereby placing the quasi-passive elastic actuator in an elastic state, the quasi-passive elastic actuator being operable in the elastic state to store and release energy and to apply an augmented torque to rotate the first support member relative to the second support member.

2. The robotic system of claim 1, wherein the valve assembly further comprises a valve housing at least partially supported by the first vane device.

3. The robotic system of claim 1, wherein the valve device comprises a movable valve component and an actuator operable to actuate the movable valve component.

4. The robotic system of claim 1, wherein the first vane device defines, at least in part, a valve housing of the valve assembly.

5. The robotic system of claim 4, wherein the first vane device comprises a rotor vane shaft defining the opening of the valve housing, the first vane device further comprising:
   a first conduit in fluid communication with the opening of the valve housing and the compression chamber;
   a second conduit in fluid communication with the opening of the valve housing and the expansion chamber.

6. The robotic system of claim 1, wherein the valve device has at least one opening through which fluid flows when in an open position to equalize gas pressure between the compression and expansion chambers, wherein the valve device is variably controllable to provide a controlled damping mode of the quasi-passive elastic actuator.

7. The robotic system of claim 1, wherein the valve device comprises one of an axis of rotation or an axis of translation collinear with the axis of rotation of the quasi-passive actuator.

8. The robotic system of claim 1, wherein the valve assembly is configured to be at least one of radially or axially gas pressure balanced to maximize switching time between the open and closed positions.

9. The robotic system of claim 1, wherein the valve device comprises:
   a movable valve component coupled to a valve actuator, the valve actuator configured to axially move the movable valve component between the open and closed positions;
   a first valve body adjacent the first movable member and having at least one fluid opening in fluid communication with an expansion chamber conduit of the first vane device; and
   a second valve body adjacent the first valve body and having at least one fluid opening in fluid communication with a compression chamber conduit of the first vane device;
   wherein, upon actuating the movable valve component from the open position to the closed position, the movable valve component covers the at least one fluid opening of the first valve body to close the shunt circuit, thereby restricting fluid flow between the compression and expansion chambers through the valve assembly.

10. The robotic system of claim 9, wherein the first and second valve bodies each comprise an outer annular channel and a plurality of fluid openings disposed around the outer annular channel to facilitate radial gas pressure balancing of the valve assembly.

11. The robotic system of claim 10, wherein the movable valve component comprises a cylindrical tube body slidably interfaced to an interior surface of the first valve body, the cylindrical tube body comprising at least one fluid opening proximate the valve actuator and in fluid communication with the fluid openings of the first and second valve bodies to facilitate axial gas pressure balancing of the valve assembly.

12. The robotic system of claim 1, wherein the valve device comprises:
a movable valve component coupled to a valve actuator;
a first valve body coupled to the movable valve component and comprising an annular recess, the movable valve component and the first valve body configured to axially move between the open and closed positions; and
a second valve body comprising a central opening that slidably receives the movable valve component and the first valve body, the second valve body comprising a first fluid opening in selective fluid communication with an expansion chamber conduit of the first vane device, and a second fluid opening in fluid communication with a compression chamber conduit of the first vane device;
wherein, upon actuating the movable valve component and first valve body from the closed position to the open position, the annular recess of the first valve body facilitates fluid communication between the first and second fluid openings to open the shunt circuit that permits fluid flow between the compression and expansion chambers through the valve assembly.

13. The robotic system of claim 12, wherein the first valve body comprises a first annular stop portion and a second annular stop portion formed on either side of the annular recess, wherein the first annular stop portion is configured to restrict fluid flow about the first fluid opening of the second valve body when in the closed position.

14. The robotic system of claim 12, wherein the second valve body comprises a first outer annular channel comprising a first plurality of fluid openings, and a second outer annular channel comprising a second plurality of fluid openings, such that the valve assembly is radially pressure balanced when in the closed and open positions.

15. The robotic system of claim 12, wherein the movable valve component comprises a cylindrically shaped tube body attached to an inner opening of the first valve body, the tube body comprising at least one fluid opening in fluid communication with chambers on either end of the cylindrical tube body such that the valve assembly is axially pressure balanced when in the closed and open positions.

16. The robotic system of claim 1, wherein the valve device comprises:
a movable valve component coupled to a valve actuator, the valve actuator configured to rotatably move the movable valve component between the open and closed positions;
a radial band device coupled to the movable valve component and comprising a first curved stop surface and a second curved stop surface; and
wherein, upon actuating the movable valve component from the open position to the closed position, the first and second curved stop surfaces close the shunt circuit that restricts fluid flow between the compression and expansion chambers through the valve assembly.

17. The robotic system of claim 1, wherein the valve device comprises:
a movable valve component coupled to a valve actuator, the valve actuator configured to axially move the movable valve component between the open and closed positions, the movable valve component comprising a plurality of through holes disposed around the movable valve component;
wherein, upon actuating the movable valve component from the open position to the closed position, the plurality of through holes are positioned to close the shunt circuit that restricts fluid flow between the compression and expansion chambers through the valve assembly.

18. The robotic system of claim 17, wherein the movable valve component comprises a central chamber in fluid communication with the plurality of through holes, such that the valve assembly is axially gas pressure balanced when in the closed and open positions.

19. The robotic system of claim 1, wherein the valve device comprises:
a movable valve component coupled to a valve actuator and configured to rotatably move between the open and closed positions, the movable valve component comprising a first fluid opening and a second fluid opening spatially separated along the movable valve component, and a central conduit in fluid communication with the first and second fluid openings;
a valve body comprising a central opening that rotatably receives the movable valve component, the valve body comprising a plurality of fluid openings disposed annularly around the valve body; and
wherein, upon actuating the movable valve component from the closed position to the open position, the plurality of openings of the valve body are in fluid communication with the second fluid opening of the movable valve component to open the shunt circuit that permits fluid flow between the compression and expansion chambers through the valve assembly.

20. The robotic system of claim 19, wherein the movable valve component comprises a plurality of through holes disposed annularly around the movable valve component such that the valve assembly is radially pressure balanced when in the closed and open positions.

21. The robotic system of claim 1, wherein the valve device comprises:
a movable valve component coupled to a valve actuator, the valve actuator configured to axially move the movable valve component between the open and closed positions;
a band device coupled to the movable valve component and comprising a first linear band portion and an opposing second linear band portion; and
a valve cartridge comprising a slot that slidably supports the band device, the valve cartridge comprising a first opening and an opposing second opening;
wherein, upon actuating the movable valve component from the open position to the closed position, the first and second linear band portions cover respective first and second openings to close the shunt circuit that restricts fluid flow between the compression and expansion chambers through the valve assembly.

22. The robotic system of claim 1, wherein the valve device comprises:
- a movable valve component coupled to a valve actuator, the valve actuator configured to rotatably move the movable valve component between the open and closed positions; and
- a band device coupled to the movable valve component and comprising a first radial band portion and an opposing second radial band portion;
- wherein, upon actuating the movable valve component from the open position to the closed position, the first and second radial band portions close the shunt circuit that restricts fluid flow between the compression and expansion chambers through the valve assembly.

* * * * *